(12) United States Patent
Blake et al.

(10) Patent No.: US 9,187,462 B2
(45) Date of Patent: Nov. 17, 2015

(54) SUBSTITUTED QUINAZOLINES AS SERINE/THREONINE KINASE INHIBITORS

(75) Inventors: James F. Blake, Boulder, CO (US); Huifen Chen, South San Francisco, CA (US); Mark Joseph Chicarelli, Boulder, CO (US); Jason Demeese, Boulder, CO (US); Rustam Ferdinand Garrey, Boulder, CO (US); John Gaudino, Boulder, CO (US); Lewis Gazzard, South San Francisco, CA (US); Robert J. Kaus, Boulder, CO (US); Samuel Kintz, South San Francisco, CA (US); Peter J. Mohr, Boulder, CO (US); David A. Moreno, Boulder, CO (US); Jacob Schwarz, South San Francisco, CA (US); Christopher S. Siedem, Boulder, CO (US); Eli M. Wallace, Boulder, CO (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/237,143

(22) PCT Filed: Aug. 3, 2012

(86) PCT No.: PCT/US2012/049551
§ 371 (c)(1),
(2), (4) Date: Feb. 4, 2014

(87) PCT Pub. No.: WO2013/020062
PCT Pub. Date: Feb. 7, 2013

(65) Prior Publication Data
US 2015/0087664 A1    Mar. 26, 2015

Related U.S. Application Data

(60) Provisional application No. 61/515,165, filed on Aug. 4, 2011.

(51) Int. Cl.
| A61K 31/517 | (2006.01) |
| C07D 239/84 | (2006.01) |
| C07D 405/14 | (2006.01) |
| C07D 403/12 | (2006.01) |

(52) U.S. Cl.
CPC ............ *C07D 405/14* (2013.01); *C07D 403/12* (2013.01)

(58) Field of Classification Search
CPC ............................ A61K 31/517; C07D 239/84
USPC ................ 514/266.4; 544/116, 292; 546/210, 546/268.1; 548/131, 235, 255, 335.1, 548/364.7, 518; 549/88, 356, 510
See application file for complete search history.

(56) References Cited

U.S. PATENT DOCUMENTS

| 8,697,715 B2 | 4/2014 | Blake et al. |
| 2003/0171383 A1 | 9/2003 | Yasuda et al. |
| 2009/0246198 A1 | 10/2009 | Dong et al. |
| 2013/0252934 A1 | 9/2013 | Blake et al. |
| 2013/0338140 A1 | 12/2013 | Blake et al. |
| 2014/0066453 A1 | 3/2014 | Blake et al. |

FOREIGN PATENT DOCUMENTS

| WO | WO 95/09847 A1 | 4/1995 |
| WO | WO 95/09851 A1 | 4/1995 |
| WO | WO 98/24780 A2 | 6/1998 |
| WO | WO 01/42241 A1 | 6/2001 |
| WO | WO 01/62233 A2 | 8/2001 |
| WO | WO 02/087513 A2 | 11/2002 |
| WO | WO 03/030909 A1 | 4/2003 |
| WO | WO 03/099808 A1 | 12/2003 |
| WO | WO 2004/007468 A1 | 1/2004 |
| WO | WO 2005/066139 A2 | 7/2005 |
| WO | WO 2005/099711 A1 | 10/2005 |
| WO | WO 2005/123680 A1 | 12/2005 |
| WO | WO 2006/021458 A2 | 3/2006 |
| WO | WO 2006/030032 A1 | 3/2006 |
| WO | WO 2006/070208 A1 | 7/2006 |
| WO | WO 2006/113704 A2 | 10/2006 |

(Continued)

OTHER PUBLICATIONS

Ashton et al., "Design and synthesis of novel amide AKT1 inhibitors with selectivity over CDK2", *Bioorganic & Medicinal Chemistry Letters*, vol. 21 (18), 5191-5196 (2011).

(Continued)

*Primary Examiner* — Douglas M Willis
(74) *Attorney, Agent, or Firm* — Viksnins Harris & Padys PLLP

(57) ABSTRACT

Compounds having the formula (I) wherein $R^1$, $R^2$, $R^3$ and Ar as defined herein are inhibitors of ERK kinase. Also disclosed are compositions and methods for treating hyperproliferative disorders.

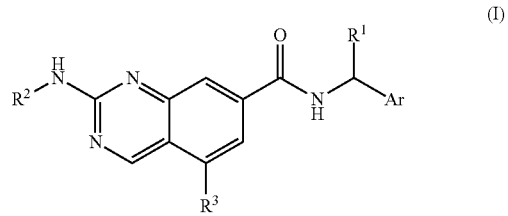

21 Claims, No Drawings

(56) References Cited

FOREIGN PATENT DOCUMENTS

| | | |
|---|---|---|
| WO | WO 2007/071348 A1 | 6/2007 |
| WO | WO 2007/097937 A1 | 8/2007 |
| WO | WO 2007/125405 A2 | 11/2007 |
| WO | WO 2008/023239 A1 | 2/2008 |
| WO | WO 2008/039882 A1 | 4/2008 |
| WO | WO 2008/079933 A1 | 7/2008 |
| WO | WO 2008/014889 A1 | 12/2008 |
| WO | WO 2009/032861 A1 | 3/2009 |
| WO | WO 2009/061761 A2 | 5/2009 |
| WO | WO 2009/156484 A2 | 12/2009 |
| WO | WO 2009/158571 A1 | 12/2009 |
| WO | WO 2010/077275 A1 | 7/2010 |
| WO | WO 2012/118850 A1 | 9/2012 |
| WO | WO 2013/020062 A1 | 2/2013 |

OTHER PUBLICATIONS

Burkhard et al., "Development of Extracellular Signal-Regulated Kinase Inhibitors", *Curr Top Med Chem* 9(8), 678-689 (2009).

Kohno et al., "Pharmacological inhibitors of the ERK signaling pathway: application as anticancer drugs", *Prog. Cell Cycle Res.*, vol. 5, 219-224 (2003).

Ma et al., "The ERK/MAPK pathway, as a target for the treatment of neuropathic pain", *Expert Opin. Ther. Targets*, 9(4), 699-713 (2005).

McIntyre et al., "Pyridazine Based Inhibitors of p38 MAPK", *Bioorganic & Medicinal Chemistry Letters 12*, 689-692 (2002).

Patent Cooperation Treaty, International Searching Authority, Search Report and Written Opinion for PCT/US2012/049551, 12 pages, Nov. 12, 2012.

Sommer et al., "Resolvins and inflammatory pain", *F1000 Medicine Reports*, 3, 19, 6 pages (2011).

Stanetty et al., "Novel and Efficient Access to Phenylaminopyrimidine Type Protein Kinase C Inhibitors Utilizing a Negishi Cross-Coupling Strategy", *Journal of Organic Chemistry 70*, 5215-5220 (2005).

Traynor et al., *Drugs of Today*, 40(8), 697-710, 698 (2004).

Yap et al., "Small Molecule Inhibitors of the ERK Signalling Pathway: Towards Novel Anti-cancer Therapeutics", *ChemMedChem*, 6(1), 38-48 (2011).

SUBSTITUTED QUINAZOLINES AS SERINE/THREONINE KINASE INHIBITORS

RELATED APPLICATIONS

This is a national stage application under 35 U.S.C. §371 of PCT/US2012/049551 filed on Aug. 3, 2012 which claims priority to U.S. provisional application No. 61/515,165 filed on Aug. 4, 2011. The entire content of the foregoing are herby incorporated herein by reference.

CROSS-REFERENCE TO PRIOR APPLICATIONS

This application claims the benefit of priority to U.S. Ser. No. 61/515,165, filed Aug. 4, 2011, which is hereby incorporated by reference in its entirety.

FIELD OF THE INVENTION

The present invention relates to compounds which inhibit serine/threonine kinases and which are useful for treating hyperproliferative and neoplastic diseases by inhibiting signal transduction pathways which commonly are overactive or overexpressed in cancerous tissue. The present compounds are selective inhibitors of ERK (extracellular-signal regulated kinase). The present invention further relates to methods for treating cancer or hyperproliferative diseases with compounds within the scope of the present invention.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase (RTK's) such as ErbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors. (M. Holum and J. Pouyssegur, *Prog. in Cell Cycle Res.* 2003 5:219).

The ERK pathway has also been cited as a promising therapeutic target for the treatment of pain and inflammation (Ma, Weiya and Remi Quirion. "The ERK/MAPK pathway, as a target for the treatment of neuropathic pain." *Expert Opin. Ther. Targets.* 9(4) (2005): pp. 699-713, and Sommer, Claudia and Frank Birklein. "Resolvins and inflammatory pain." *F1000 Medicine Reports.* 3:19 (2011)).

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

There is a continuing need for new and novel therapeutic agents which can be used for cancer and hyperproliferative conditions. The Raf/MEK/ERK pathway is an important signaling pathway which is frequently overexpressed and/or overactive in many cancerous tissues. Design and development of new pharmaceutical compounds is essential. In one aspect of the present invention there is provided a compound according to formula I wherein:

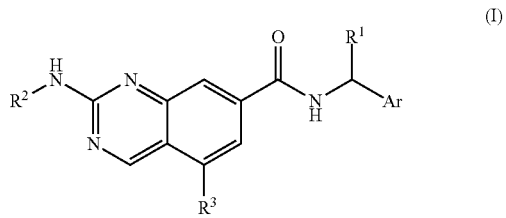

(I)

$R^1$ is heterocyclyl or heteroaryl optionally substituted with one to three substituents independently selected from the group consisting of $C_{1-6}$ alkyl, $C_{1-6}$ hydroxyalkyl, halogen, hydroxyl and oxo;

Ar is phenyl or pyridinyl optionally substituted by 1 to 5 groups independently selected from the group consisting of $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro;

$R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, 2-oxabicyclo[2.2.1]heptan-5-yl, oxetanyl, piperidinyl, N—$C_{1-6}$ alkyl-piperidinyl, 1,1-dioxothietan-3-yl, thietan-3-yl, and N—$C_{1-6}$ alkyl-2-oxo-pyrrolidinyl and wherein said heterocyclyl or heterocyclyl-$C_{1-6}$ alkyl is optionally substituted by 1 to 3 groups independently selected from $C_{1-6}$ alkyl, $C_{1-6}$ haloalkyl, $C_{1-4}$ acyloxy-$C_{1-2}$ alkyl, halogen, hydroxyl, phenyl, $C_{1-3}$ hydroxyalkyl and oxo, (d) $C_{3-7}$ cycloalkyl or $C_{3-7}$ cycloalkyl-$C_{1-6}$ alkyl wherein said cycloalkyl or $C_{3-7}$ cycloalkyl-$C_{1-6}$ alkyl are optionally substituted by one to three hydroxyl, $C_{1-3}$ alkoxy or halo, (e) $C_{1-6}$ heteroalkyl wherein the heteroalkyl moiety at least includes $C_{1-6}$ hydroxyalkyl or $C_{1-3}$ alkoxy-$C_{1-6}$ alkoxy, (f) heteroaryl wherein said heteroaryl is selected from the group consisting of pyrazolyl and pyridinyl wherein said heteroaryl is optionally independently substituted with one to three groups selected from the group consisting of $C_{1-6}$ alkyl groups, $C_{1-6}$ haloalkyl and halogen. and (g) $C_{1-3}$ cyanoalkyl;

optionally substituted with one to three $C_{1-6}$ alkyl groups and (g) $C_{1-3}$ cyanoalkyl;

$R^3$ is hydrogen or halogen; or, a stereoisomer, tautomer or pharmaceutically acceptable salt thereof.

In another aspect of the present invention there is provided a compound according to formula I wherein $R^1$ is heterocyclyl or heteroaryl optionally substituted with one to three substituents independently selected from the group consisting of $C_{1-6}$ alkyl, $C_{1-6}$ hydroxyalkyl, halogen, hydroxyl and oxo; Ar is phenyl optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-6}$ haloalkyl, $C_{1-4}$ acyloxy-$C_{1-2}$ alkyl, halogen, hydroxyl, phenyl, $C_{1-3}$ hydroxyalkyl and oxo, (d) $C_{3-7}$ cycloalkyl or $C_{3-7}$ cycloalkyl-$C_{1-6}$ alkyl wherein said cycloalkyl or $C_{3-7}$ cycloalkyl-$C_{1-6}$ alkyl are optionally substituted by hydroxyl or halo, and (e) $C_{1-6}$ heteroalkyl; $R^3$ is hydrogen or halogen, and stereoisomers, tautomers or pharmaceutically acceptable salts thereof.

The present invention also relates to a method for treating a hyperproliferative disorder by administering a therapeutically effective quantity of a compound according to formula I to a patient in need thereof. The compound can be administered alone or co-administered with at least one other anti-hyperproliferative or chemotherapeutic compound.

The present invention also relates to a method for inhibiting ERK protein kinase activity in a cell comprising treating a cell with a compound according to formula I in an amount effective to attenuate or eliminate ERK kinase activity.

The present invention also relates to a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined above" and "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " - - - " drawn through a bond each refer to the point of attachment of a functional group or other chemical moiety to the rest of the molecule of which it is a part. Thus, for example:

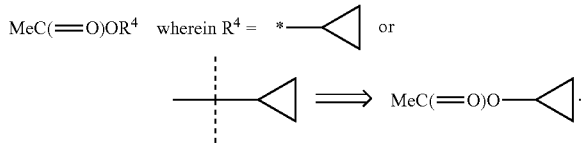

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—$CH_2$—$\leftrightarrows$—C(—OH)=CH—), amide/imidic acid (—C(=O)—NH—$\leftrightarrows$—C(—OH)=N—)

and amidine (—C(=NR)—NH— ⇌ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of formula I and, where appropriate, the individual tautomeric forms thereof.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatises such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40; and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with at least one substituent selected from the other specifically-named group. Thus, for example, "phenylalkyl" refers to an alkyl group having at least one phenyl substituent, and thus includes benzyl and phenylethyl. An "alkylaminoalkyl" is an alkyl group having at least one alkylamino substituent. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term—(ar)alkyl refers to either an unsubstituted alkyl or an aralkyl group. The term (hetero)aryl or (het)aryl refers to a moiety that is either an aryl or a heteroaryl group.

The term "alkyl" as used herein alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, methyl, ethyl, propyl, i-propyl, n-butyl, i-butyl, t-butyl, neopentyl, hexyl, and octyl.

The term "haloalkyl" as used herein denotes an unbranched or branched chain alkyl group as defined above, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The term "$C_{1-6}$ fluoroalkyl" as used herein denotes an unbranched or branched chain alkyl group as defined above, wherein 1, 2, 3 or more hydrogen atoms are substituted by a fluorine.

The term "cyano-$C_{1-3}$ alkyl" refers to a $C_{1-3}$ alkyl moiety in which a hydrogen atom is replaced by cyano.

The term "haloalkoxy" as used herein refers to a group —OR, wherein R is haloalkyl as defined herein. The term "haloalkylthio" as used herein refers to a group —SR, wherein R is haloalkyl as defined herein.

The term "alkoxycarbonyl" as used herein denotes a group of formula —C(=O)OR, wherein R is alkyl as defined herein.

The term "$C_{1-4}$ acyloxy-$C_{1-2}$ alkyl" as used herein denotes a group of formula —$(CH_2)_{1-2}OC(O)(CH_2)_{0-3}H$. The term "$C_{1-4}$ acyloxy" as used herein denotes the radical —OC(O)R, wherein the radical contains 1 to 4 carbon atoms and $C_1$ is formyl.

The term "halogen" or "halo" as used herein means fluorine, chlorine, bromine, or iodine.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or S(=O)$_{0-2}$) with the remaining ring atoms being carbon. The heterocyclyl moiety can optionally be independently substituted with one or more, preferably one or two substituents selected from hydroxy, oxo, cyano, lower alkyl, lower alkoxy, lower haloalkoxy, $C_{1-6}$ alkylthio, halo, $C_{1-6}$ haloalkyl, $C_{1-6}$ hydroxyalkyl, nitro, $C_{1-6}$ alkoxycarbonyl, $C_{1-4}$ acyloxy-$C_{1-2}$ alkyl, $C_{1-6}$ acyl, amino, $C_{1-6}$ alkylamino, $C_{1-6}$ alkylsulfonyl, arylsulfonyl, $C_{1-6}$ alkylaminosulfonyl, arylaminosulfonyl, $C_{1-6}$ alkylsulfonylamido, arylsulfonylamido, $C_{1-6}$ alkylaminocarbonyl, arylaminocarbonyl, $C_{1-6}$ alkylcarbonylamino, or arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl, unless specifically limited. Heterocycles include a 3 to 7 membered ring containing 1 to 3 heteroatoms selected from N, O or S.

The term "heteroaryl" or "heteroaromatic" as used herein means a monocyclic or bicyclic radical of 5 to 12 ring atoms having at least one aromatic ring containing five to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 4 heteroatoms selected from N, O or S, include, unless specifically limited, pyridinyl, pyrimidinyl, pyrazinyl, pyrrolyl, pyrazolyl, imidazolyl, oxazolyl, isoxazolyl, thiazolyl, isothiazolyl, tetrazole, triazolinyl, thiadiazolyl and oxadiaxolinyl, which can optionally be substituted with one or more, preferably one or two substituents selected from hydroxy, cyano, $C_{1-6}$ alkyl, aryl, $C_{1-3}$ aralkyl, $C_{1-6}$ alkoxy, thio, lower haloalkoxy, $C_{1-6}$ alkylthio, halo, $C_{1-6}$haloalkyl, $C_{1-6}$ alkylsulfinyl, $C_{1-6}$ alkylsulfonyl, halogen, amino, $C_{1-6}$ alkylamino, $C_{1-6}$ dialkylamino, amino-$C_{1-3}$ alkyl, $C_{1-3}$ alkylaminoalkyl, $C_{1-3}$ dialkylamino-$C_{1-3}$ alkyl, nitro, $C_{1-6}$ alkoxycarbonyl, $C_{1-4}$ acyloxy-$C_{1-2}$ alkyl, carbamoyl, $C_{1-3}$ alkylcarbamoyl, $C_{1-3}$ dialkylcarbamoyl, arylcarbamoyl, $C_{1-6}$ alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring.

The terms "hydroxyalkyl" and "alkoxyalkyl" as used herein denotes alkyl radical as herein defined, wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The term "alkylthio" or "alkylsulfanyl" means an —S-alkyl group, wherein alkyl is as herein defined, such as methylthio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an —S-alkyl, wherein alkyl is $C_{1-10}$. "Arylthio" means an —S-aryl group, wherein aryl is as defined herein. "Phenylthio" is an "arylthio" moiety, wherein aryl is phenyl.

The term "cycloalkyl" as used herein denotes a saturated carbocyclic ring containing 3 to 8 carbon atoms, i.e., cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "acylamino" as used herein denotes a group of formula —NHC(=O)R, wherein R is hydrogen or lower alkyl as defined herein. $C_{1-6}$ acylamino refers to an acylamino group, wherein the C(=O)R moiety contains 1 to 6 carbon atoms. The $C_1$ acyl or "alkanoyl" group is a formyl group wherein R=H and a $C_6$ acyl group refers to hexanoyl when the alkyl chain is unbranched.

The term "heteroalkyl" as used herein means an alkyl radical as defined herein, wherein one or two hydrogen atoms have been replaced with a substituent independently selected from the group consisting of —$OR^a$ and —$NR^bR^c$, with the understanding that the point of attachment of the heteroalkyl radical is through a carbon atom. $R^a$ is hydrogen or alkyl and $R^b$ and $R^c$ are independently of each other hydrogen, acyl, alkyl, or $R^b$ and $R^c$ together with the nitrogen to which they are attached form a cyclic amine. Hydroxyalkyl, alkoxyalkyl, aminoalkyl, alkylaminoalkyl and dialkylaminoalkyl moieties are subgenera encompassed by the term "heteroalkyl". Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-methylaminopropyl, and the like.

The term "oxo" as used herein refers to "=O" (i.e., a doubly bonded oxygen affording a carbonyl group when attached to a carbon atom), wherein it is further understood that this is equivalent to two hydroxyl groups attached to the same carbon are equivalent.

The terms "treat" and "treatment" refer to therapeutic treatment, wherein the object is to slow down (lessen) an undesired physiological change or disorder, such as the spread of cancer. For purposes of this invention, beneficial or desired clinical results include, but are not limited to, alleviation of symptoms, limiting the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin 107 1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®), Genentech); and (x) pharmaceutically acceptable salts, acids and derivatives of any of the above.

In one embodiment there is provided a compound according to formula I wherein $R^1$, $R^2$, $R^3$ and Ar are as described herein above.

In another embodiment there is provided a compound according to formula I wherein $R^1$ is optionally substituted pyrazolyl, triazolyl oxadiazolyl, oxazolyl, imidazolinyl or isoxazolyl.

In another embodiment there is provided a compound according to formula I wherein $R^1$ is optionally substituted pyrazolyl, triazolyl oxadiazolyl, oxazolyl or isoxazolyl.

In another embodiment there is provided a compound according to formula I wherein $R^1$ is oxadiazolyl.

In another embodiment there is provided a compound according to formula I wherein $R^1$ is triazolyl. In another embodiment there is provided a compound according to formula I wherein $R^1$ is optionally substituted triazolyl.

In another embodiment there is provided a compound according to formula I wherein $R^1$ is optionally substituted imidazolinyl. In another embodiment there is provided a compound according to formula I wherein $R^1$ is optionally substituted oxazolinyl.

In another embodiment there is provided a compound according to formula I wherein $R^1$ is optionally substituted isoxazolinyl.

In another embodiment there is provided a compound according to formula I wherein $R^1$ is 2-alkyl-2H-1,2,3-triazol-4-yl. In another embodiment there is provided a compound according to formula I wherein $R^1$ is 2-($C_{1-6}$ alkyl)-2H-1,2,3-triazol-4-yl. In yet another embodiment there is provided a compound according to formula I wherein $R^1$ is 2-methyl-2H-1,2,3-triazol-4-yl.

In another embodiment there is provided a compound according to formula I wherein $R^1$ is optionally substituted pyrazolyl. In another embodiment there is provided a compound according to formula I wherein $R^1$ is substituted pyrazolyl. In another embodiment there is provided a compound according to formula I wherein $R^1$ is optionally substituted 1H-pyrazol-3-yl or 1H-pyrazol-4-yl. In another embodiment there is provided a compound according to formula I wherein $R^1$ is 1-alkyl-1H-pyrazol-3-yl or 1-alkyl-1H-pyrazol-4-yl. In another embodiment there is provided a compound according to formula I wherein $R^1$ is 1-($C_{1-6}$ alkyl)-1H-pyrazol-3-yl, 1-($C_{1-6}$ alkyl)-1H-pyrazol-4-yl or 1-($C_{1-6}$ hydroxyalkyl)-1H-pyrazol-4-yl. In another embodiment there is provided a compound according to formula I wherein $R^1$ is 1-methyl-1H-pyrazol-3-yl, 1-methyl-1H-pyrazol-4-yl or 1-(2-hydroxyethyl)-1H-pyrazol-4-yl.

In another embodiment, $R^1$ is heterocyclyl or heteroaryl, wherein the heterocyclyl and heteroaryl are optionally substituted with one to three substituents independently selected from $C_{1-6}$ alkyl, $C_{1-6}$ hydroxyalkyl, halogen, hydroxyl and oxo. In another embodiment, $R^1$ is heterocyclyl or heteroaryl, wherein the heterocyclyl and heteroaryl are optionally substituted with $C_{1-6}$ alkyl, $C_{1-6}$ hydroxyalkyl or halogen.

In certain embodiments, $R^1$ is heterocyclyl, wherein the heterocyclyl is optionally substituted with one to three substituents independently selected from $C_{1-6}$ alkyl, $C_{1-6}$ hydroxyalkyl, halogen, hydroxyl and oxo, and wherein the heterocyclyl is a 3 to 7 membered ring containing 1 to 3 heteroatoms selected from N, O and S. In certain embodiments, $R^1$ is heterocyclyl, wherein the heterocyclyl is optionally substituted with $C_{1-6}$ alkyl or halogen, and wherein the heterocyclyl is a 3 to 7 membered ring containing 1 to 3 heteroatoms selected from N, O and S. In certain embodiments, $R^1$ is pyrrolidinyl, wherein the pyrrolidinyl is optionally substituted with one to three substituents independently selected from $C_{1-6}$ alkyl, $C_{1-6}$ hydroxyalkyl, halogen, hydroxyl and oxo. In certain embodiments, $R^1$ is pyrrolidinyl, wherein the pyrrolidinyl is optionally substituted with $C_{1-6}$ alkyl or halogen. In certain embodiments, $R^1$ is pyrrolidin-2-yl, pyrrolidin-3-yl, 3-fluoro-pyrrolidin-3-yl, 1-methyl-pyrrolidin-2-yl, 4-fluoro-pyrrolidin-2-yl or 5-methyl-pyrrolidin-2-yl.

In certain embodiments, $R^1$ is heteroaryl, wherein the heteroaryl is optionally substituted with one to three substituents independently selected from $C_{1-6}$ alkyl, $C_{1-6}$ hydroxyalkyl, halogen, hydroxyl and oxo, and wherein the heteroaryl is a 5 to 6 membered ring containing 1 to 4 heteroatoms selected from N, O and S. In certain embodiments, $R^1$ is heteroaryl, wherein the heteroaryl is optionally substituted with $C_{1-6}$ alkyl or $C_{1-6}$ hydroxyalkyl, and wherein the heteroaryl is a 5 to 6 membered ring containing 1 to 4 heteroatoms selected from N, O and S. In certain embodiments, $R^1$ is heteroaryl, wherein the heteroaryl is optionally substituted with one to three substituents independently selected from the group consisting of $C_{1-6}$ alkyl, $C_{1-6}$ hydroxyalkyl, halogen, hydroxyl and oxo, and wherein the heteroaryl is selected from pyrazolyl, oxadiazolyl, triazolyl oxazolyl, imidazolinyl and isoxazolyl. In certain embodiments, $R^1$ is heteroaryl, wherein the heteroaryl is optionally substituted with one to three substituents independently selected from $C_{1-6}$ alkyl, $C_{1-6}$ hydroxyalkyl, halogen, hydroxyl and oxo, and wherein the heteroaryl is selected from pyrazolyl, oxadiazolyl and triazolyl. In certain embodiments, $R^1$ is heteroaryl, wherein the heteroaryl is optionally substituted with $C_{1-6}$ alkyl or $C_{1-6}$ hydroxyalkyl, and wherein the heteroaryl is selected from pyrazolyl, oxadiazolyl and triazolyl. In certain embodiments, $R^1$ is 1-methyl-1H-pyrazol-4-yl, 1-methyl-1H-pyrazol-3-yl, 1-ethyl-1H-pyrazol-3-yl, 1,2,4-oxadiazol-5-yl, 2-methyl-2H-1,2,3-triazol-4-yl or 1-(2-hydroxyethyl)-1H-pyrazol-4-yl.

In certain embodiments, $R^1$ is selected from the group consisting of 1-methyl-1H-pyrazol-4-yl, 1-methyl-1H-pyrazol-3-yl, 1-ethyl-1H-pyrazol-3-yl, 1,2,4-oxadiazol-5-yl, 2-methyl-2H-1,2,3-triazol-4-yl, 1-(2-hydroxyethyl)-1H-pyrazol-4-yl, pyrrolidin-2-yl, pyrrolidin-3-yl, 3-fluoro-pyrrolidin-3-yl, 1-methyl-pyrrolidin-2-yl, 4-fluoro-pyrrolidin-2-yl and 5-methyl-pyrrolidin-2-yl.

In another embodiment there is provided a compound according to formula I wherein $R^1$ is an optionally substituted pyrazolyl, triazolyl, oxadiazolyl, oxazolyl or isoxazolyl moiety, and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, or halogen, (d) 2-hydroxy-1-methyl-ethan-1-yl, (e) 2,2,2-trifluoro-1-methyl-ethan-1-yl, (f) (1) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In another embodiment there is provided a compound according to formula I wherein $R^1$ is an optionally substituted pyrazolyl, triazolyl or oxadiazolyl moiety and $R^2$ is selected from the group conciting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, or halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In yet another embodiment of the present invention there is provided a compound according to formula I wherein $R^1$ is an optionally substituted pyrazolyl, triazolyl or oxadiazolyl moiety and, $R^2$ is tetrahydropyranyl or tetrahydrofuranyl optionally substituted with $C_{1-3}$ hydroxyalkyl or halogen. In yet another embodiment of the present invention there is provided a compound according to formula I wherein $R^1$ is an optionally substituted pyrazolyl, triazolyl or oxadiazolyl moiety, and $R^2$ is tetrahydropyranyl or tetrahydrofuranyl. In yet another embodiment of the present invention there is provided a compound according to formula I wherein $R^1$ is an optionally substituted pyrazolyl, triazolyl or oxadiazolyl moiety, and $R^2$ is tetrahydropyranyl or tetrahydrofuranyl substituted by one or two fluorine atoms. In yet another embodiment of the present invention there is provided a compound according to formula I wherein $R^1$ is an optionally substituted pyrazolyl, triazolyl or oxadiazolyl moiety, and $R^2$ is tetrahydropyranyl or tetrahydrofuranyl substituted by hydroxymethyl.

In another embodiment, there is provided a compound according to formula I wherein $R^1$ is an optionally substituted pyrazolyl, triazolyl, oxadiazolyl, oxazolyl or isoxazolyl moiety, and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl. In another embodiment, there is provided a compound according to formula I wherein $R^1$ is an optionally substituted pyrazolyl, triazolyl or oxadiazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In yet another embodiment of the present invention there is provided a compound according to formula I wherein $R^1$ is an optionally substituted pyrazolyl, triazolyl or oxadiazolyl moiety, and $R^2$ is pyrazolyl wherein said pyrazolyl moiety is optionally substituted with one to three groups independently selected from the group consisting of $C_{1-6}$ alkyl, $C_{1-6}$ haloalkyl and halogen. In yet another embodiment of the present invention there is provided a compound according to formula I wherein $R^1$ is an optionally substituted pyrazolyl, triazolyl or oxadiazolyl moiety, and $R^2$ is pyrazolyl substituted with one to three $C_{1-6}$ alkyl groups. In another embodiment there is provided a compound according to formula I wherein $R^1$ is an optionally substituted pyrazolyl, triazolyl or oxadiazolyl moiety, and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted pyrazolyl, triazolyl, oxadiazolyl, oxazolyl or isoxazolyl moiety, and $R^2$ is tetrahydropyran-4-yl or 3-fluoro-tetrahydropyran-4-yl. In another embodiment there is provided a compound according to formula I wherein $R^1$ is an optionally substituted pyrazolyl, triazolyl or oxadiazolyl moiety, and $R^2$ is tetrahydropyran-4-yl or 3-fluoro-tetrahydropyran-4-yl.

In another embodiment there is provided a compound according to formula I wherein $R^1$ is an optionally substituted pyrazolyl, triazolyl, oxadiazolyl, oxazolyl or isoxazolyl moiety, and $R^2$ is 2-hydroxymethyl-tetrahydropyran-4-yl. In another embodiment there is provided a compound according to formula I wherein $R^1$ is an optionally substituted pyrazolyl, triazolyl, or oxadiazolyl moiety, and $R^2$ is 2-hydroxymethyl-tetrahydropyran-4-yl.

In another embodiment there is provided a compound according to formula I wherein $R^1$ is an optionally substituted triazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from the group consisting of $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from the group consisting of $C_{1-6}$ alkyl, $C_{1-6}$ haloalkyl and halogen. In yet another embodiment of the present invention there is provided a compound according to formula I wherein $R^1$ is an optionally substituted triazolyl moiety and $R^2$ is tetrahydropyranyl or tetrahydrofuranyl optionally substituted with $C_{1-3}$ hydroxyalkyl or halogen. In yet another embodiment of the present invention there is provided a compound according to formula I wherein $R^1$ is an optionally substituted triazolyl moiety and $R^2$ is tetrahydropyranyl or tetrahydrofuranyl. In yet another embodiment of the present invention there is provided a compound according to formula I wherein $R^1$ is an optionally substituted triazolyl moiety and $R^2$ is tetrahydropyranyl or tetrahydrofuranyl substituted by one or two fluorine atoms. In another embodiment there is provided a compound according to formula I wherein $R^1$ is an optionally substituted triazolyl moiety and $R^2$ is tetrahydropyran-4-yl or 3-fluoro-tetrahydropyran-4-yl. In yet another embodiment of the present invention there is provided a compound according to formula I wherein $R^1$ is an optionally substituted triazolyl moiety and $R^2$ is tetrahydropyranyl or tetrahydrofuranyl substituted by hydroxymethyl.

In another embodiment there is provided a compound according to formula I wherein $R^1$ is an optionally substituted triazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is an optionally substituted triazolyl moiety and $R^2$ is 2-hydroxymethyl-tetrahydropyran-4-yl.

In another embodiment there is provided a compound according to formula I wherein $R^1$ is an optionally substituted triazolyl moiety and $R^2$ is pyrazolyl optionally substituted with one to three $C_{1-3}$ alkyl groups. In another embodiment there is provided a compound according to formula I wherein $R^1$ is an optionally substituted triazolyl moiety and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted oxadiazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from the group consisting of $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In another embodiment there is provided a compound according to formula I wherein $R^1$ is an optionally substituted oxadiazolyl moiety and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl. In yet another embodiment of the present invention there is provided a compound according to formula I wherein $R^1$ is an optionally substituted oxadiazolyl moiety and $R^2$ is tetrahydropyranyl or tetrahydrofuranyl. In yet another embodiment of the present invention there is provided a compound according to formula I wherein $R^1$ is an optionally substituted oxadiazolyl moiety and $R^2$ is tetrahydropyranyl or tetrahydrofuranyl optionally substituted with $C_{1-3}$ hydroxyalkyl or halogen. In yet another embodiment of the present invention there is provided a compound according to formula I wherein $R^1$ is an optionally substituted oxadiazolyl moiety and $R^2$ is tetrahydropyranyl or tetrahydrofuranyl substituted by one or two fluorine atoms. In another embodiment there is provided a compound according to formula I wherein $R^1$ is an optionally substituted oxadiazolyl moiety and $R^2$ is tetrahydropyran-4-yl or 3-fluoro-tetrahydropyran-4-yl. In yet another embodiment of the present invention there is provided a compound according to formula I wherein $R^1$ is an optionally substituted oxadiazolyl moiety and $R^2$ is tetrahydropyranyl or tetrahydrofuranyl substituted by hydroxymethyl. In another embodiment there is provided a compound according to formula I wherein $R^1$ is an optionally substituted oxadiazolyl moiety and $R^2$ is 2-hydroxymethyl-tetrahydropyran-4-yl.

In another embodiment there is provided a compound according to formula I wherein $R^1$ is an optionally substituted oxadiazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is an optionally substituted oxadiazolyl moiety and $R^2$ is pyrazolyl wherein said pyrazolyl moiety is optionally independently substituted with one to three $C_{1-6}$ alkyl groups. In another embodiment there is provided a compound according to formula I wherein $R^1$ is an optionally substituted oxadiazolyl moiety and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted pyrazolyl moiety and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In another embodiment there is provided a compound according to formula I wherein $R^1$ is a 1-alkyl-1H-pyrazol-3-yl or 1-alkyl-1H-pyrazol-4-yl moiety and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In yet another embodiment of the present invention there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is tetrahydropyranyl or tetrahydrofuranyl. In yet another embodiment of the present invention there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is tetrahydropyranyl or tetrahydrofuranyl optionally substituted with $C_{1-3}$ hydroxyalkyl or halogen. In yet another embodiment of the present invention there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is tetrahydropyranyl or tetrahydrofuranyl substituted by one or two fluorine atoms. In yet another embodiment of the present invention there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is tetrahydropyranyl or tetrahydrofuranyl substituted by hydroxymethyl.

In another embodiment there is provided a compound according to formula I wherein $R^1$ is an optionally substituted pyrazolyl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl. In another embodiment there is provided a compound according to formula I wherein $R^1$ is a 1-alkyl-1H-pyrazol-3-yl or 1-alkyl-1H-pyrazol-4-yl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is an optionally substituted pyrazolyl moiety and $R^2$ is pyrazolyl optionally substituted with one to three $C_{1-3}$ alkyl groups. In another embodiment there is provided a compound according to formula I wherein $R^1$ is an optionally substituted pyrazolyl moiety and $R^2$ is 2-methylpyrazol-3-yl, 2,5-dimethylpyrazol-3-yl or 1,3-dimethylpyrazol-4-yl.

In yet another embodiment of the present invention there is provided a compound according to formula I wherein $R^1$ is an 1-alkyl-1H-pyrazol-3-yl, 1-alkyl-1H-pyrazol-4-yl or 1-hydroxyalkyl-1H-pyrazol-4-yl moiety and $R^2$ is tetrahydropyran-4-yl or 3-fluoro-tetrahydropyranyl.

In yet another embodiment of the present invention there is provided a compound according to formula I wherein $R^1$ is an 1-alkyl-1H-pyrazol-3-yl, 1-alkyl-1H-pyrazol-4-yl or 1-hydroxyalkyl-1H-pyrazol-4-yl moiety and $R^2$ is 2-(hydroxymethyl)tetrahydropyran-4-yl.

In another embodiment there is provided a compound according to formula I wherein $R^1$ is an 1-alkyl-1H-pyrazol-3-yl, 1-alkyl-1H-pyrazol-4-yl or 1-hydroxyalkyl-1H-pyrazol-4-yl moiety and $R^2$ is pyrazolyl substituted with one to three $C_{1-6}$ alkyl groups. In another embodiment there is provided a compound according to formula I wherein $R^1$ is an 1-alkyl-1H-pyrazol-3-yl, 1-alkyl-1H-pyrazol-4-yl or 1-hydroxyalkyl-1H-pyrazol-4-yl moiety and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is a 1-methyl-1H-pyrazol-3-yl or 1-methyl-1H-pyrazol-4-yl moiety and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is tetrahydropyranyl or tetrahydrofuranyl. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is tetrahydropyranyl or tetrahydrofuranyl optionally substituted with $C_{1-3}$ hydroxyalkyl or halogen. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is tetrahydropyranyl or tetrahydrofuranyl substituted by one or two fluorine atoms. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is tetrahydropyran-4-yl or 3-fluorotetrahydropyran-4-yl. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is tetrahydropyranyl or tetrahydrofuranyl substituted by hydroxymethyl. In yet another embodiment of the present invention there is provided a compound according to formula I wherein $R^1$ is a 1-methyl-1H-pyrazol-3-yl or 1-methyl-1H-pyrazol-4-yl moiety, and $R^2$ is 2-(hydroxymethyl)tetrahydropyran-4-yl.

In another embodiment there is provided a compound according to formula I wherein $R^1$ is a 1-methyl-1H-pyrazol-3-yl or 1-methyl-1H-pyrazol-4-yl moiety and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is a 1-methyl-1H-pyrazol-3-yl or 1-methyl-1H-pyrazol-4-yl moiety, and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted pyrazolyl moiety and $R^2$ is tetrahydropyran-4-yl, 3-fluorotetrahydropyran-4-yl or 2-(hydroxymethyl)tetrahydropyran-4-yl. In another embodiment there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is tetrahydropyran-4-yl, 3-fluoro-tetrahydropyran-4-yl or 2-(hydroxymethyl)tetrahydropyran-4-yl. In another embodiment there is provided a compound according to formula I wherein $R^1$ is a 1-methyl-1H-pyrazol-3-yl, 1-methyl-1H-pyrazol-4-yl or 1-(2-hydroxyethyl)-1H-pyrazol-4-yl moiety and $R^2$ is tetrahydropyran-4-yl, 3-fluoro-tetrahydropyran-4-yl or 2-(hydroxymethyl)tetrahydropyran-4-yl.

In another embodiment there is provided a compound according to formula I wherein $R^{1'}$ is an pyrazolyl moiety optionally substituted with one to three groups independently selected from the group consisting of $C_{1-6}$ alkyl and halogen and $R^2$ is pyrazolyl substituted with one to three $C_{1-6}$ alkyl groups. In another embodiment there is provided a compound according to formula I wherein $R^1$ is a 1-alkyl-1H-pyrazol-3-yl, 1-alkyl-1H-pyrazol-4-yl or 1-hydroxyalkyl-1H-pyrazol-4-yl moiety and $R^2$ is pyrazolyl substituted with one to three $C_{1-6}$ alkyl groups. In another embodiment there is provided a compound according to formula I wherein $R^1$ is a 1-methyl-1H-pyrazol-3-yl, 1-methyl-1H-pyrazol-4-yl or 1-(2-hydroxyethyl)-1H-pyrazol-4-yl moiety and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted pyrrolidinyl, piperdinyl or morpholinyl. In another embodiment there is provided a compound according to formula I wherein $R^1$ is an optionally substituted pyrrolidinyl. In another embodiment there is provided a compound according to formula I wherein $R^1$ is 1-methyl-pyrrolidin-2-yl or 1-methyl-pyrrolindin-3-yl. In another embodiment there is provided a compound according to formula I wherein $R^1$ is pyrrolidin-2-yl or pyrrolindin-3-yl.

In another embodiment there is provided a compound according to formula I wherein $R^1$ is an optionally substituted pyrrolidinyl, and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In yet another embodiment of the present invention there is provided a compound according to formula I wherein $R^1$ is an optionally substituted pyrrolidinyl and $R^2$ is tetrahydropyran-4-yl or tetrahydrofuran-3-yl. In yet another embodiment of the present invention there is provided a compound according to formula I wherein $R^1$ is an optionally substituted pyrrolidinyl and $R^2$ is 3-fluoro-tetrahydropyran-4-yl. In yet another embodiment of the present invention there is provided a compound according to formula I wherein $R^1$ is an optionally substituted pyrrolidinyl and $R^2$ is 2-(hydroxymethyl)tetrahydropyran-4-yl. In yet another embodiment of the present invention there is provided a compound according to formula I wherein $R^1$ is an optionally substituted pyrrolidinyl and $R^2$ is 2-methylpyrazol-3-yl, 2,5-dimethylpyrazol-3-yl or 1,3-dimethylpyrazol-4-yl.

In another embodiment there is provided a compound according to formula I wherein $R^1$ is an optionally substituted pyrrolidinyl, and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is pyrrolidin-2-yl or pyrrolidin-3-yl, and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen.

In another embodiment there is provided a compound according to formula I wherein $R^1$ is pyrrolidin-2-yl or pyrrolidin-3-yl, and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is 1-alkyl-pyrrolidin-2-yl or 1-alkyl-pyrrolidin-3-yl, and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen.

In another embodiment there is provided a compound according to formula I wherein $R^1$ is 1-alkyl-pyrrolidin-2-yl or 1-alkyl-pyrrolidin-3-yl, and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is 1-methyl-pyrrolidin-2-yl or 1-methyl-pyrrolidin-3-yl and $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen.

In another embodiment there is provided a compound according to formula I wherein $R^1$ is 1-methyl-pyrrolidin-2-yl or 1-methyl-pyrrolidin-3-yl and $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl and (k) 4-hydroxycyclohexyl.

In another embodiment there is provided a compound according to formula I wherein $R^1$ is an optionally substituted pyrrolidinyl and $R^2$ is tetrahydropyran-4-yl, 3-fluoro-tetrahydropyran-4-yl or 2-(hydroxymethyl)tetrahydropyran-4-yl.

In another embodiment there is provided a compound according to formula I wherein $R^1$ is pyrrolidin-2-yl or pyrrolidin-3-yl, and $R^2$ is tetrahydropyran-4-yl, 3-fluoro-tetrahydropyran-4-yl or 2-(hydroxymethyl)tetrahydropyran-4-yl. In another embodiment there is provided a compound according to formula I wherein $R^1$ is pyrrolidin-2-yl or pyrrolidin-3-yl, and $R^2$ is pyrazolyl wherein said pyrazolyl moiety is optionally substituted with one to three groups independently selected from the group consisting of $C_{1-6}$ alkyl, $C_{1-6}$ haloalkyl and halogen.

In certain embodiments, Ar is phenyl optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro. In certain embodiments, Ar is phenyl optionally substituted by 1 or 2 groups independently selected from $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro. In certain embodiments, Ar is phenyl substituted by 1 or 2 groups independently selected from $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro. In certain embodiments, Ar is phenyl optionally substituted by 1 or 2 groups independently selected from $C_{1-6}$ haloalkyl, $C_{1-6}$ alkoxy, halogen, $C_{1-6}$ haloalkoxy and cyano. In certain embodiments, Ar is phenyl substituted by 1 or 2 groups independently selected from $C_{1-6}$ haloalkyl, $C_{1-6}$ alkoxy, halogen, $C_{1-6}$ haloalkoxy and cyano. In certain embodiments, Ar is 4-chloro-3-fluorophenyl, 3-chloro-4-fluorophenyl, 3-fluoro-4-trifluoromethylphenyl, 3-fluoro-4-methoxyphenyl, 4-difluoromethoxyphenyl, 3-chloro-4-methoxyphenyl, 4-cyano-3-fluorophenyl, 3-chloro-4-cyanophenyl, 3-cyano-4-methoxyphenyl or 3-fluorophenyl.

In certain embodiments, Ar is pyridinyl optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro. In certain embodiments, Ar is pyridinyl optionally substituted by one to three groups independently selected from $C_{1-6}$ alkyl and $C_{1-6}$ alkoxy, In certain embodiments, $R^2$ is selected from the group consisting of (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from $C_{1-6}$ alkyl, $C_{1-6}$ haloalkyl, $C_{1-4}$ acyloxy-$C_{1-2}$ alkyl, $C_{1-3}$ hydroxyalkyl and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen. In certain embodiments, $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-6}$ haloalkyl, $C_{1-4}$ acyloxy-$C_{1-2}$ alkyl, halogen, hydroxyl, phenyl, $C_{1-3}$ hydroxyalkyl and oxo, (d) $C_{3-7}$ cycloalkyl or $C_{3-7}$ cycloalkyl-$C_{1-6}$ alkyl wherein said cycloalkyl is optionally substituted by hydroxyl or halo, and (e) $C_{1-6}$ heteroalkyl. In certain embodiments, $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-4}$ acyloxy-$C_{1-2}$ alkyl, halogen, and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl or halo, and (e) $C_{1-6}$ heteroalkyl. In certain embodiments, $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle is optionally substituted by 1 to 3 groups independently selected from the group consisting of $C_{1-6}$ alkyl, halogen, $C_{1-3}$ hydroxyalkyl and $C_{1-4}$ acyloxy-$C_{1-2}$ alkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl. In certain embodiments, $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl and oxetanyl and wherein said heterocycle is optionally substituted by $C_{1-6}$ alkyl, halogen, $C_{1-3}$ hydroxyalkyl or $C_{1-4}$ acyloxy-$C_{1-2}$ alkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl. In certain embodiments, $R^2$ is 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydropyran-4-yl, 3-fluorotetrahydropyran-4-yl, 2-(hydroxymethyl)tetrahydropyran-4-yl, (4-tetrahydro-2H-pyran-2-yl)methyl acetate, tetrahydrofuran-3-yl, 3-methyloxetan-3-yl, oxetanyl-3-ylmethyl or 2-methoxyethyl. In certain embodiments, $R^2$ is 1-hydroxypropan-2-yl, isopropyl, 1-cyclopropylethyl, cyclopropylmethyl, 4-hydroxycyclohexyl, 1,1,1-trifluoropropan-2-yl or 3-fluoropropyl. In certain embodiments, $R^2$ is tetrahydropyran-4-yl, 3-fluorotetrahydropyran-4-yl, 2-(hydroxymethyl)tetrahydropyran-4-yl, (4-tetrahydro-2H-pyran-2-yl)methyl acetate, tetrahydrofuran-3-yl, 3-methyloxetan-3-yl or oxetany-3-ylmethyl. In certain embodiments, $R^2$ is tetrahydropyran-4-yl, 3-fluorotetrahydropyran-4-yl, 2-(hydroxymethyl)tetrahydropyran-4-yl, (4-tetrahydro-2H-pyran-2-yl)methyl acetate, tetrahydrofuran-3-yl or 3-methyloxetan-3-yl. In certain embodiments, $R^2$ is 2-methoxyethyl. In certain embodiments, $R^2$ is pyrazolyl wherein said pyrazolyl moiety is optionally substituted with one to three groups independently selected from the group consisting of $C_{1-6}$ alkyl, $C_{1-6}$ haloalkyl and halogen. In certain embodiments, $R^2$ is pyrazolyl wherein said pyrazolyl moiety is optionally independently substituted with one to three $C_{1-6}$ alkyl groups. In certain embodiments, $R^2$ is 2-methylpyrazol-3-yl, 2,5-dimethylpyrazol-3-yl or 1,3-dimethylpyrazol-4-yl.

In certain embodiments, $R^3$ is hydrogen or halogen. In certain embodiments, $R^3$ is hydrogen or F. In certain embodiments, $R^3$ is hydrogen. In certain embodiments, $R^3$ is halogen. In certain embodiments, $R^3$ is F.

In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl or pyridinyl optionally substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-4}$ acyloxy-$C_{1-2}$ alkyl, halogen and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl optionally substituted by 1 or 2 groups independently selected from the group consisting of $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-4}$ acyloxy-$C_{1-2}$ alkyl, halogen and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl optionally substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, and oxetanyl and wherein said heterocycle is optionally substituted by $C_{1-6}$ alkyl, $C_{1-4}$ acyloxy-$C_{1-2}$ alkyl, halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) tetrahydropyranyl, tetrahydrofuranyl or oxetanyl optionally substituted with halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (f) $C_{1-6}$ hydroxyalkyl; and $R^3$ is hydrogen or F In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is pyrazolyl wherein said pyrazolyl moiety is optionally substituted with one to three groups independently selected the group consisting of rom $C_{1-6}$ alkyl, $C_{1-6}$ haloalkyl and halogen. In certain embodiments, $R^2$ is 2-methylpyrazol-3-yl, 2,5-dimethylpyrazol-3-yl or 1,3-dimethylpyrazol-4-yl; and $R^3$ is hydrogen or F.

In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl optionally substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-4}$ acyloxy-$C_{1-2}$ alkyl, halogen and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, and oxetanyl and wherein said heterocycle is optionally substituted by $C_{1-6}$ alkyl, $C_{1-4}$ acyloxy-$C_{1-2}$ alkyl, halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 3-7 membered heterocyclyl or 5-6 membered heteroaryl, wherein the heterocyclyl and heteroaryl are optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) tetrahydropyranyl, tetrahydrofuranyl or oxetanyl optionally substituted with halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (f) $C_{1-6}$ hydroxyalkyl; and $R^3$ is hydrogen or F.

In certain embodiments, $R^1$ is 3-7 membered heterocyclyl optionally substituted with $C_{1-6}$ alkyl or halogen, or heteroaryl optionally substituted with $C_{1-6}$ alkyl or $C_{1-6}$ hydroxyalkyl; Ar is phenyl optionally substituted by 1 or 2 groups independently selected from the group consisting of $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl and oxetanyl and wherein said heterocycle is optionally substituted by 1 to 3 groups independently selected from $C_{1-6}$ alkyl, $C_{1-4}$ acyloxy-$C_{1-2}$ alkyl, halogen and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, (e) $C_{1-6}$ heteroalkyl; and $R^3$ is hydrogen or F. In certain embodiments, $R^1$ is 3-7 membered heterocyclyl optionally substituted with $C_{1-6}$ alkyl or halogen, or heteroaryl optionally substituted with $C_{1-6}$ alkyl or $C_{1-6}$ hydroxyalkyl; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) tetrahydropyranyl, tetrahydrofuranyl or oxetanyl optionally substituted with $C_{1-6}$ alkyl, $C_{1-4}$ acyloxy-$C_{1-2}$ alkyl, halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F.

In certain embodiments, $R^1$ is 5-6 membered heteroaryl optionally substituted with $C_{1-6}$ alkyl, $C_{1-6}$ hydroxyalkyl or halogen; Ar is phenyl optionally substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocycle or heterocyclyl-$C_{1-6}$ alkyl is selected from the group consisting of tetrahydropyranyl, tetrahydrofuranyl, oxetanyl, piperidinyl, N—$C_{1-6}$ alkyl-piperidinyl and N—$C_{1-6}$ alkyl-2-oxo-pyrrolidinyl and wherein said heterocycle or heterocyclyl-$C_{1-6}$ alkyl is optionally substituted by 1 to 3 groups independently selected from $C_{1-6}$ alkyl, $C_{1-4}$ acyloxy-$C_{1-2}$ alkyl, halogen and $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 5-6 membered heteroaryl optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is selected from the group consisting of (a) $C_{1-10}$ alkyl, (b) $C_{1-6}$ haloalkyl, (c) tetrahydropyranyl, tetrahydrofuranyl or oxetanyl optionally substituted with halogen or $C_{1-3}$ hydroxyalkyl, (d) $C_{3-7}$ cycloalkyl or $C_{3-7}$ cycloalkyl-$C_{1-6}$ alkyl wherein said cycloalkyl is optionally substituted by hydroxyl, and (e) $C_{1-6}$ heteroalkyl; and $R^3$ is hydrogen or F. In certain embodiments, $R^1$ is 5-6 membered heteroaryl optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is pyrazolyl wherein said pyrazolyl moiety is optionally substituted with one to three groups independently selected from the group consisting of $C_{1-6}$ alkyl, $C_{1-6}$ haloalkyl and halogen. In certain embodiments, $R^1$ is 5-6 membered heteroaryl optionally substituted with $C_{1-6}$ alkyl, $C_{1-6}$ hydroxyalkyl or halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is 2-methylpyrazol-3-yl, 2,5-dimethylpyrazol-3-yl or 1,3-dimethylpyrazol-4-yl; and $R^3$ is hydrogen or F.

In certain embodiment, $R^1$ is pyrazolyl optionally independently substituted with one to three groups selected from $C_{1-6}$ alkyl, $C_{1-6}$ hydroxyalkyl and halogen; Ar is phenyl substituted by 1 or 2 groups independently selected from $C_{1-6}$ haloalkyl, $C_{1-6}$ alkoxy, halogen, $C_{1-6}$ haloalkoxy and cyano; $R^2$ is pyrazolyl wherein said pyrazolyl moiety is optionally substituted with one to three groups independently selected from $C_{1-6}$ alkyl, $C_{1-6}$ haloalkyl and halogen. In a subembodiment $R^2$ is pyrazolyl that is optionally substituted with one to three $C_{1-6}$ alkyl groups. In another subembodiment, $R^2$ is 2-methylpyrazol-3-yl, 2,5-dimethylpyrazol-3-yl or 1,3-dimethylpyrazol-4-yl; and $R^3$ is hydrogen or F.

In another embodiment there is provided a compound according to formula I which compound is selected from the group consisting of compounds I-1 to I-70 in TABLE I and compounds II-1 to II-54 in TABLE II, or a stereoisomer, tautomer or a pharmaceutically acceptable salt thereof. In another embodiment there is provided a compound according to formula I which compound is selected from the group consisting of compounds I-1 to I-70 in TABLE I or a stereoisomer, tautomer or a pharmaceutically acceptable salt thereof. In another embodiment there is provided a compound according to formula I which compound is selected from the group consisting of compounds II-1 to II-54 in TABLE II or a stereoisomer, tautomer or a pharmaceutically acceptable salt thereof.

In another embodiment there is provided a compound according to formula I or a stereoisomer, tautomer or a pharmaceutically acceptable salt thereof which compound is selected from the group consisting of:
((2S,4S)-2-hydroxymethyl-tetrahydro-pyran-4-ylamino)-quinazoline-7-carboxylic acid [(S)-(3-fluoro-4-methoxy-phenyl)-(1-methyl-1H-pyrazol-4-yl)-methyl]-amide;
2-((2S,4R)-2-hydroxymethyl-tetrahydro-pyran-4-ylamino)-quinazoline-7-carboxylic acid [(S)-(4-chloro-3-fluoro-phenyl)-(1-methyl-1H-pyrazol-4-yl)-methyl]-amide;
2-(tetrahydro-pyran-4-ylamino)-quinazoline-7-carboxylic acid [(R)-(3-chloro-4-cyano-phenyl)-(1-methyl-1H-pyrazol-4-yl)-methyl]-amide;
2-(tetrahydro-pyran-4-ylamino)-quinazoline-7-carboxylic acid [(R)-(3-cyano-4-methoxy-phenyl)-(1-methyl-1H-pyrazol-4-yl)-methyl]-amide; and,
2-(tetrahydro-pyran-4-ylamino)-quinazoline-7-carboxylic acid [(S)-(3-chloro-4-cyano-phenyl)-(1-methyl-1H-pyrazol-4-yl)-methyl]-amide.

In another embodiment there is provided a method of inhibiting ERK protein kinase activity in a cell comprising treating the cell with a compound according to formula I.

In another embodiment of the present invention there is provided a method of inhibiting ERK protein kinase activity in a patient in need thereof comprising the step of administering to said patient a compound according to formula I.

In another embodiment there is provided a method of treating or ameliorating the severity of a hyperproliferative disorder in a patient in need thereof comprising administering to said patient a compound according to formula I.

In another embodiment there is provided a method of treating or ameliorating the severity of a hyperproliferative disorder in a patient in need thereof wherein said hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma comprising administering to said patient a compound according to formula I.

In another embodiment there is provided a method of treating or ameliorating the severity of a hyperproliferative disorder in a patient in need thereof comprising co-administering to said patient a compound according to formula I with at least one other chemotherapeutic agent used to treat or ameliorate a hyperproliferative disorder.

In another embodiment there is provided a use of a compound of formula I in the manufacture of a medicament for the treatment of a hyperproliferative disease.

In another embodiment there is provided a compound of formula I for the treatment of a hyperproliferative disease.

In another embodiment the hyperproliferative disorder is cancer.

In another embodiment the hyperproliferative disorder is melanoma.

In another embodiment the hyperproliferative disorder is pancreatic cancer.

In another embodiment the hyperproliferative disorder is thyroid cancer.

In another embodiment the hyperproliferative disorder is colorectal cancer.

In another embodiment the hyperproliferative disorder is lung cancer.

In another embodiment the hyperproliferative disorder is breast cancer.

In another embodiment the hyperproliferative disorder is ovarian cancer.

In another embodiment the hyperproliferative disorder is acute myelogenous leukemia.

In another embodiment the hyperproliferative disorder is chronic myelomonocytic leukemia.

In another embodiment the hyperproliferative disorder is chronic myelogenous leukemia.

In another embodiment the hyperproliferative disorder is multiple myeloma.

In another embodiment the hyperproliferative disorder is myeloid leukemia.

In another embodiment there is provided a composition containing a compound according to formula I with at least one carrier, diluent or excipient.

In another embodiment of the present invention there is provided a compound of formula I for use as a medicament. In another embodiment of the present invention there is provided a compound selected from TABLE 1 for use as a medicament.

In another embodiment of the present invention there is provided the use of a compound of formula I for the manufacture of a medicament. In another embodiment of the present invention there is provided the use of a compound selected from TABLE 1 for the manufacture of a medicament.

In another embodiment of the present invention there is provided a compound of formula I for use in therapy.

In another embodiment of the present invention there is provided a compound of formula I for use in the treatment of a hyperproliferative disease.

In another embodiment of the present invention there is provided a pharmaceutical composition comprising a compound of formula I for use in the treatment of a hyperproliferative disease.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), days (d), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), diphenylphosphoryl azide (DPPA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N, hours (h), N,N'N'-tetramethyluronium hexafluorophosphate acetic acid (HATU), acetic acid (HOAc), 1-hydroxy-7-aza-benzotriazole (HOAt), 1-N-hydroxybenzotriazole (HOBt), high pressure liquid chromatography (HPLC), iso-propanol (IPA), lithium diisopropylamide (LDA), methanol (MeOH), melting point (mp), $MeSO_2$— (mesyl or Ms), methyl (Me), acetonitrile (MeCN), m-chloroperbenzoic acid (MCPBA), minutes (min), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), saturated (satd.), tert-butyldimethylsilyl or t-BuMe$_2$Si (TBDMS), tetrabutyl ammonium fluoride (TBAF), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo-have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

TABLE I

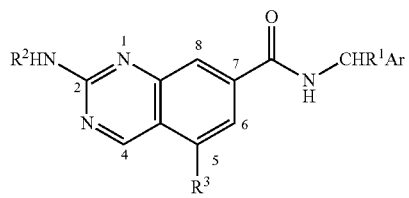

| Cpd No. | Structure | IC50[1] (μM) | MS[2] | $^1$H-NMR |
|---|---|---|---|---|
| I-1 | (structure shown) | 0.0025 | 469.2 | (CDCl$_3$) δ 9.02 (s, 1H), 7.82 (s, 1H), 7.73 (m, 2H), 7.40 (m, 1H), 7.18 (m, 3H), 6.71 (m, 1H), 6.33 (d, 1H), 5.46 (m, 1H), 4.27 (m, 1H), 3.89 (s, 3H), 3.85 (m, 1H), 3.72 (m, 1H), 1.34 (d, 3H), 1.25 (m, 1H). |

TABLE I-continued

| Cpd No. | Structure | IC50¹ (μM) | MS² | ¹H-NMR |
|---|---|---|---|---|
| I-2 | 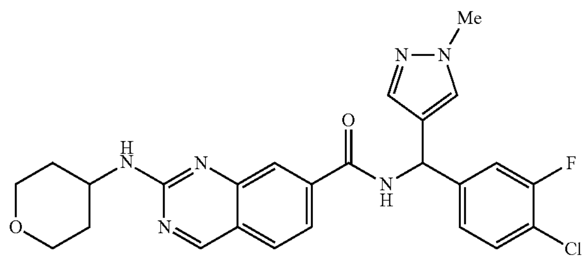 [SMILES: Cn1cc(C(NC(=O)c2ccc3cnc(NC4CCOCC4)nc3c2)c2ccc(Cl)c(F)c2)cn1] | 0.0008 | 495.0 | (CDCl₃) δ 9.02 (s, 1H), 7.85 (s, 1H), 7.75 (d, 1H), 7.67 (d, 1H). 7.40 (t, 2H), 7.20 (m, 2H), 7.15 (d, 1H), 6.70 (d, 1H), 6.33 (d, 1H), 5.30 (m, 1H), 4.20 (m, 1H), 4.03 (m, 2H), 3.89 (s, 3H), 3.60 (t, 2H), 2.12 (d, 2H), 1.62 (m, 2H). |
| I-3 | 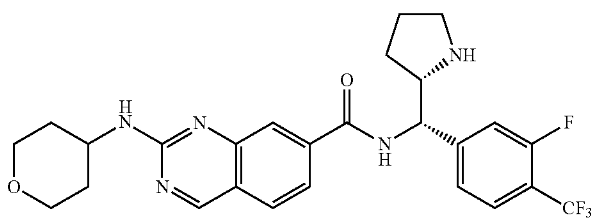 [SMILES: O=C(N[C@@H](c1ccc(C(F)(F)F)c(F)c1)[C@@H]1CCCN1)c1ccc2cnc(NC3CCOCC3)nc2c1] | 0.0021 | 518.2 | (CDCl₃) δ 9.02 (s, 1H), 7.97 (s, 1H), 7.72 (m, 2H), 7.58 (m, 1H). 7.23 (m, 2H), 5.35 (d, 1H), 5.15 (dd, 1H), 4.26 (m, 1H), 4.04 (m, 2H), 3.62 (m, 2H), 3.55 (br m, 1H), 3.05 (m, 1H), 2.94 (m, 1H), 2.14 (m, 2H), 2.02 (m, 1H), 1.74 (m, 6H). |
| I-4 | 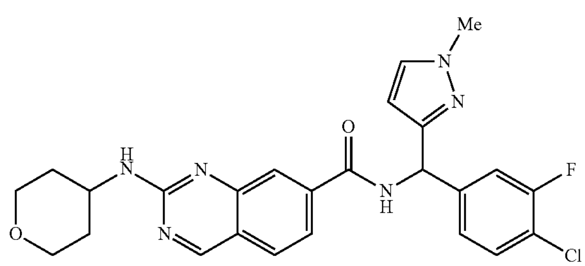 [SMILES: Cn1ccc(C(NC(=O)c2ccc3cnc(NC4CCOCC4)nc3c2)c2ccc(Cl)c(F)c2)n1] | 0.0050 | 495.0 | (CDCl₃) δ 9.01 (s, 1H), 7.96 (s, 1H), 7.72 (dd, 2H), 7.65 (d, 1H), 7.34 (m, 2H), 7.22 (m, 2H), 6.28 (d, 1H), 6.07 (d, 1H), 5.26 (d, 1H), 4.24 (m, 1H), 4.03 (m, 2H), 3.92 (s, 3H), 3.61 (m, 2H), 2.12 (d, 2H), 1.62 (m, 2H) |
| I-5 | 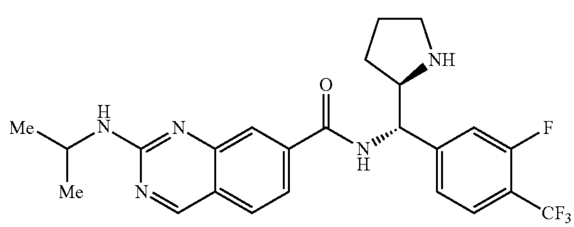 [SMILES: CC(C)Nc1ncc2ccc(C(=O)N[C@@H](c3ccc(C(F)(F)F)c(F)c3)[C@H]3CCCN3)cc2n1] | 0.0023 | 476.0 | |
| I-6 | 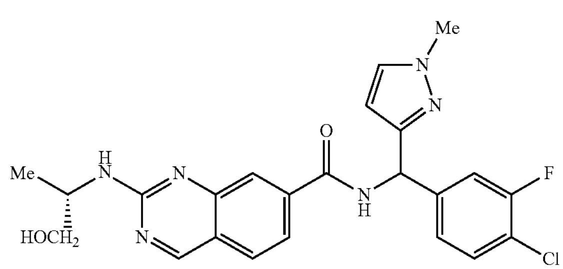 | 0.0050 | 469.0 | |

TABLE I-continued

| Cpd No. | Structure | IC50 (μM) | MS | ¹H-NMR |
|---|---|---|---|---|
| I-7 | 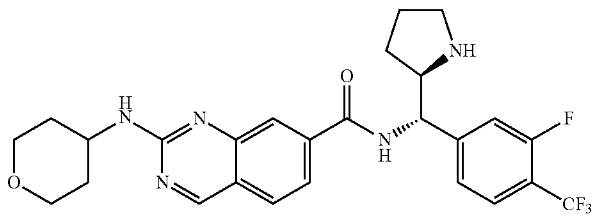 [SMILES: O=C(N[C@@H](c1ccc(C(F)(F)F)c(F)c1)[C@H]1CCCN1)c1ccc2cnc(NC3CCOCC3)nc2c1] | 0.0018 | 518.1 | (CDCl₃) δ 9.01 (s, 1H), 7.89 (s, 1H), 7.73 (d, 1H), 7.66 (dd, 1H), 7.57 (m, 1H), 7.32 (br s, 1H), 7.29 (d, 1H), 7.18 (d, 1H), 5.30 (d, 1H), 5.05 (m, 1H), 4.24 (m, 1H), 4.04 (m, 2H), 3.62 (m, 3H), 2.90 (m, 2H), 2.14 (d, 2H), 1.86 (m, 1H), 1.62 (m, 6H). |
| I-8 | 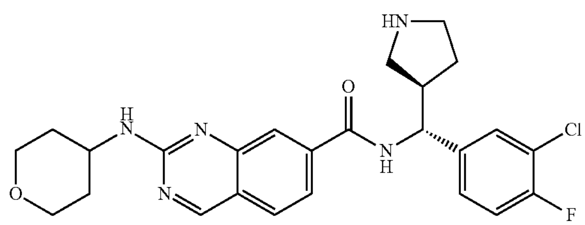 [SMILES: O=C(N[C@@H](c1ccc(F)c(Cl)c1)[C@@H]1CCNC1)c1ccc2cnc(NC3CCOCC3)nc2c1] | 0.0067 | 485.2 | |
| I-9 | 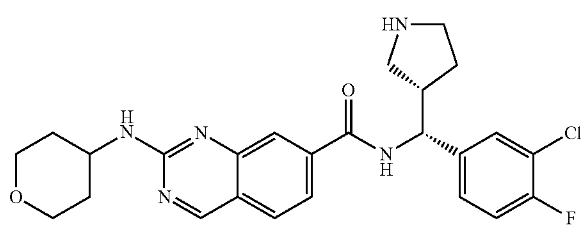 [SMILES: O=C(N[C@@H](c1ccc(F)c(Cl)c1)[C@H]1CCNC1)c1ccc2cnc(NC3CCOCC3)nc2c1] | 0.0067 | 485.2 | |
| I-10 | 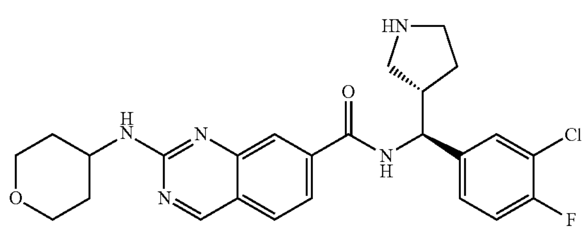 [SMILES: O=C(N[C@H](c1ccc(F)c(Cl)c1)[C@H]1CCNC1)c1ccc2cnc(NC3CCOCC3)nc2c1] | 0.0054 | 485.1 | |
| I-11 | 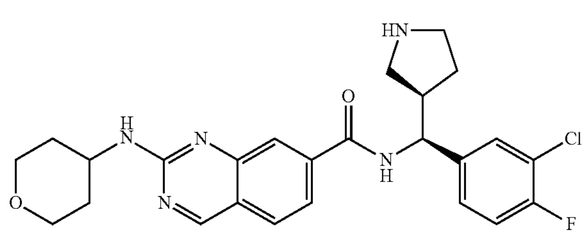 [SMILES: O=C(N[C@H](c1ccc(F)c(Cl)c1)[C@@H]1CCNC1)c1ccc2cnc(NC3CCOCC3)nc2c1] | 0.0064 | 485.1 | (CDCl₃) δ 8.94 (s, 1H), 7.87 (s, 1H), 7.60 (m, 2H), 7.53 (d, 1H), 7.32 (m, 1H), 7.07 (m, 1H), 5.41 (br s, 1H), 5.19 (m, 1H), 4.17 (br s, 1H), 4.00 (d, 2H), 3.56 (m, 2H), 3.44 (br s, 1H), 3.32 (m, 1H), 3.17 (m, 1H), 3.05 (m, 1H), 2.95 (m, 1H), 2.27 (m, 1H), 2.06 (m, 3H), 1.60 (m, 3H). |

TABLE I-continued

[Structure: R²HN-quinazoline core with positions labeled 1,2,4,5,6,7,8, substituent R³ at position 5, and C(O)NH-CHR¹Ar at position 7]

| Cpd No. | Structure | IC50 (μM) | MS | ¹H-NMR |
|---|---|---|---|---|
| I-12 | [tetrahydropyran-NH-quinazoline-C(O)NH-CH(1-methylpyrazol-4-yl)(3-fluoro-4-chlorophenyl)] | 0.0014 | 495.1 | (CDCl₃) δ 9.01 (s, 1H), 7.85 (s, 1H), 7.71 (dd, 2H), 7.40 (m, 2H), 7.19 (m, 2H), 7.15 (d, 1H), 6.72 (d, 1H), 6.33 (d, 1H), 5.30 (d, 1H), 4.20 (m, 1H), 4.02 (m, 2H), 3.89 (s, 3H), 3.59 (m, 2H), 2.12 (d, 2H), 1.61 (m, 2H). |
| I-13 | [tetrahydropyran-NH-quinazoline-C(O)NH-CH(1-methylpyrazol-4-yl)(3-fluoro-4-chlorophenyl)] | 0.0388 | 495.1 | (CDCl₃) δ 9.01 (s, 1H), 7.85 (s, 1H), 7.71 (dd, 2H), 7.40 (m, 2H), 7.19 (m, 2H), 7.15 (d, 1H), 6.72 (d, 1H), 6.33 (d, 1H), 5.30 (d, 1H), 4.20 (m, 1H), 4.02 (m, 2H), 3.89 (s, 3H), 3.59 (m, 2H), 2.12 (d, 2H), 1.61 (m, 2H). |
| I-14 | [Me-CH(CH₂OH)-NH-quinazoline-C(O)NH-CH(1-methylpyrazol-4-yl)(3-fluoro-4-chlorophenyl)] | 0.0568 | 469.2 | |
| I-15 | [Me-CH(CH₂OH)-NH-quinazoline-C(O)NH-CH(1-methylpyrazol-4-yl)(3-fluoro-4-chlorophenyl)] | 0.0012 | 469.2 | |
| I-16 | [tetrahydropyran-NH-quinazoline-C(O)NH-CH(3-fluoropyrrolidin-3-yl)(3-chloro-4-fluorophenyl)] | | 503.1 | |

TABLE I-continued

| Cpd No. | Structure | IC50[1] (μM) | MS[2] | $^1$H-NMR |
|---|---|---|---|---|
| I-17 | 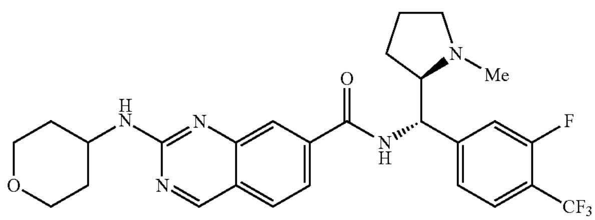 [SMILES: CN1CCC[C@@H]1[C@@H](NC(=O)c1ccc2cnc(NC3CCOCC3)nc2c1)c1ccc(C(F)(F)F)c(F)c1] | 0.0028 | 532.1 | (CDCl$_3$) δ 9.04 (s, 1H), 7.96 (s, 1H), 7.73 (dd, 2H), 7.56 (m, 1H), 7.20 (d, 1H), 7.15 (d, 1H), 5.30 (d, 1H), 5.07 (m, 1H), 4.26 (m, 1H), 4.04 (m, 2H), 3.62 (m, 2H), 3.19 (m, 1H), 2.59 (m, 1H), 2.36 (s, 3H), 2.34 (m, 1H), 2.14 (d, 2H), 1.78 (m, 1H), 1.65 (m, 2H), 1.40 (m, 1H). |
| I-18 | 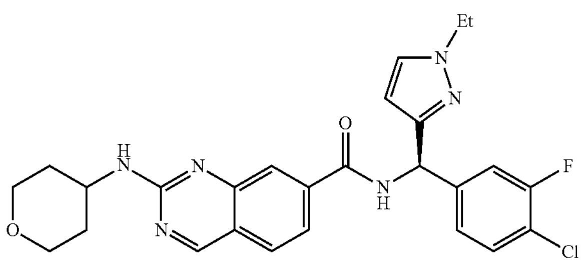 [SMILES: CCn1ccc([C@H](NC(=O)c2ccc3cnc(NC4CCOCC4)nc3c2)c2ccc(Cl)c(F)c2)n1] | 0.0128 | 509.0 | (CDCl$_3$) δ 9.02 (s, 1H), 7.86 (s, 1H), 7.72 (dd, 2H), 7.41 (m, 2H), 7.21 (s, 1H), 7.18 (m, 2H), 6.72 (d, 1H), 6.33 (d, 1H), 5.30 (d, 1H), 4.20 (m, 1H), 4.15 (q, 2H), 4.02 (m, 2H), 3.60 (m, 2H), 2.12 (d, 2H), 1.62 (m, 2H), 1.49 (t, 3H). |
| I-19 | 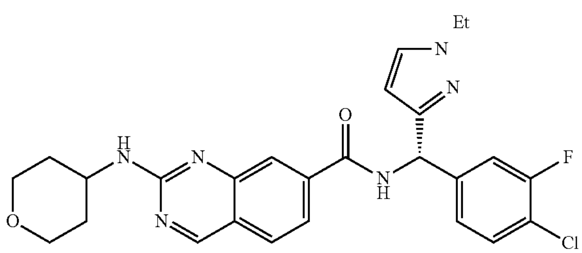 [SMILES: N=C(/C=C\N)[C@@H](NC(=O)c1ccc2cnc(NC3CCOCC3)nc2c1)c1ccc(Cl)c(F)c1 ; "Et"] | 0.0024 | 509.1 | (CDCl$_3$) δ 9.02 (s, 1H), 7.86 (s, 1H), 7.72 (dd, 2H), 7.41 (m, 2H), 7.21 (s, 1H), 7.18 (m, 2H), 6.72 (d, 1H), 6.33 (d, 1H), 5.30 (d, 1H), 4.20 (m, 1H), 4.15 (q, 2H), 4.02 (m, 2H), 3.60 (m, 2H), 2.12 (d, 2H), 1.62 (m, 2H), 1.49 (t, 3H). |
| I-20 | 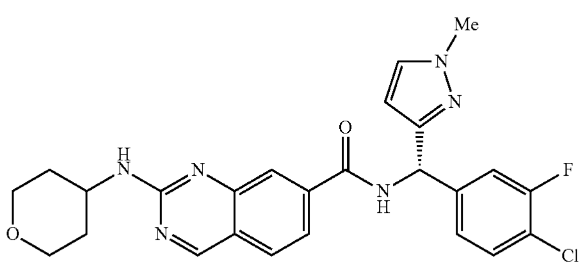 | 0.0020 | 495.0 | |
| I-21 | 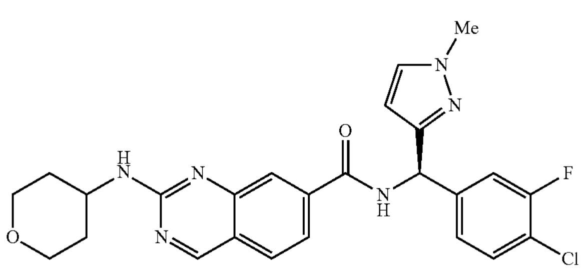 [SMILES: Cn1ccc([C@H](NC(=O)c2ccc3cnc(NC4CCOCC4)nc3c2)c2ccc(Cl)c(F)c2)n1] | 0.069 | 495.0 | |

TABLE I-continued
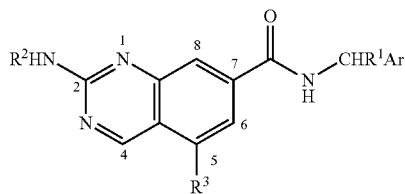
| Cpd No. | Structure | IC50[1] (μM) | MS[2] | $^1$H-NMR |
|---|---|---|---|---|
| I-22 | 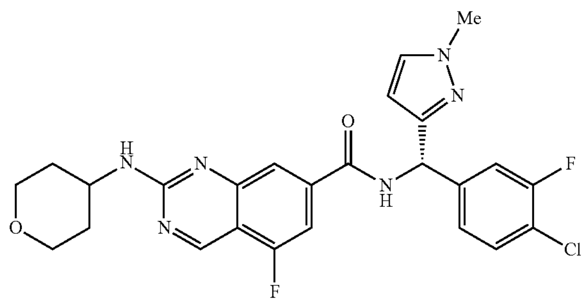 [SMILES: Cn1ccc([C@@H](NC(=O)c2cc(F)c3cnc(NC4CCOCC4)nc3c2)c2ccc(Cl)c(F)c2)n1] | 0.0014 | 513.0 | (CDCl$_3$) δ 9.26 (s, 1H), 7.62 (s, 1H), 7.38-7.43 (m, 2H), 7.29-7.34 (m, 1H), 7.19 (m, 1H), 7.15 (m, 1H), 6.67 (m, 1H), 6.31 (m, 1H), 5.40 (m, 1H), 4.20 (s, 1H), 4.00-4.06 (m, 2H), 3.89 (s, 3H), 3.59 (m, 2H), 2.11 (m, 2H), 1.59-1.68 (m, 2H). |
| I-23 | 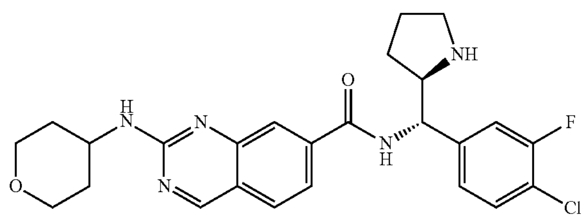 [SMILES: O=C(N[C@@H](c1ccc(Cl)c(F)c1)[C@H]1CCCN1)c1ccc2cnc(NC3CCOCC3)nc2c1] | 0.0023 | 484.0 | (CDCl$_3$) δ 9.01 (s, 1H), 7.88 (s, 1H), 7.70 (dd, 2H), 7.36 (m, 1H), 7.21 (dd, 2H), 7.12 (d, 1H), 5.29 (d, 1H), 5.01 (m, 1H), 4.24 (m, 1H), 4.04 (m, 2H), 3.60 (m, 2H), 3.56 (m, 1H), 2.87 (m, 2H), 2.13 (d, 2H), 1.87 (m, 1H), 1.60 (m, 4H). |
| I-24 | 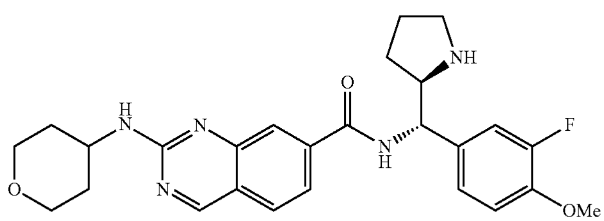 [SMILES: COc1ccc([C@H](NC(=O)c2ccc3cnc(NC4CCOCC4)nc3c2)[C@H]2CCCN2)cc1F] | 0.0082 | 480 | |
| I-25 | 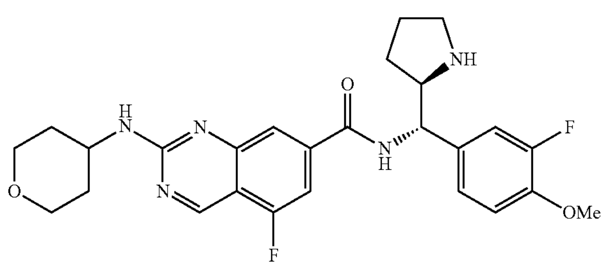 [SMILES: COc1ccc([C@H](NC(=O)c2cc(F)c3cnc(NC4CCOCC4)nc3c2)[C@H]2CCCN2)cc1F] | 0.0090 | 498.0 | (d$_6$-DMSO) δ 9.29 (s, 1H), 9.03 (m, 1H), 7.87 (m, 1H), 7.30 (m, 2H), 7.18 (m, 1H), 7.09 (m, 1H), 4.75 (m, 1H), 4.10 (m, 1H), 3.91 (m, 2H), 3.81 (s, 3H), 3.74 (s, 1H), 3.39-3.49 (m, 4H), 2.71-2.83 (m, 2H), 1.89 (m, 4H), 1.52-1.71 (m, 4H). |
| I-26 | 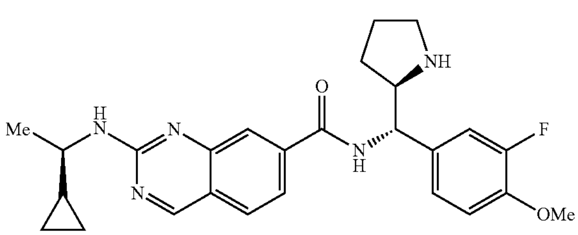 [SMILES: COc1ccc([C@H](NC(=O)c2ccc3cnc(N[C@H](C)C4CC4)nc3c2)[C@H]2CCCN2)cc1F] | 0.002 | 464 | (d$_6$-DMSO) δ 9.13 (s, 1H), 8.97 (d, 1H), 7.90 (s, 1H), 7.82 (d, 1H), 7.54 (m, 1H), 7.48 (br s, 1H), 7.32 (m, 1H), 7.20 (m, 1H), 7.10 (m, 1H), 5.76 (m, 1H), 4.82 (m, 1H), 3.80 (s, 3H), 3.67 (m, 1H), 3.50 (m, 1H), 2.81 (m, 2H), 1.92 (m, 1H), 1.67 (m, 2H), 1.51 (m, 1H), 1.25 (d, 3H), 1.02 (m, 1H), 0.45 (m, 1H), 0.36 (m, 2H), 0.20 (m, 1H). |

TABLE I-continued

| Cpd No. | Structure | IC50¹ (µM) | MS² | ¹H-NMR |
|---|---|---|---|---|
| I-27 | 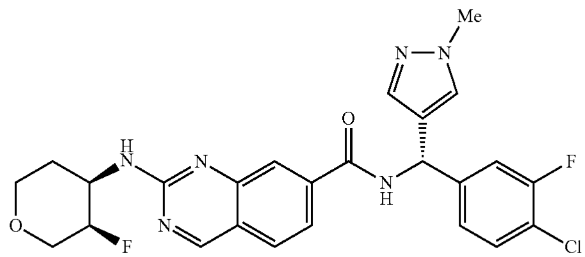 [SMILES: Cn1cc([C@@H](NC(=O)c2ccc3cnc(N[C@@H]4CCOC[C@@H]4F)nc3c2)c2ccc(Cl)c(F)c2)cn1] | 0.0158 | 513 | |
| I-28 | 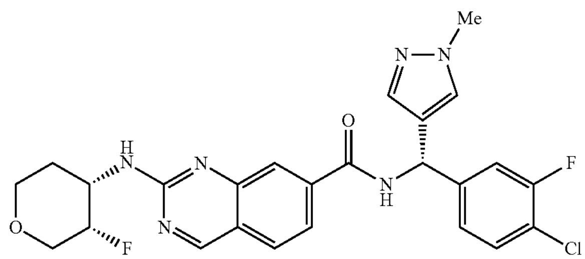 [SMILES: Cn1cc([C@@H](NC(=O)c2ccc3cnc(N[C@H]4CCOC[C@H]4F)nc3c2)c2ccc(Cl)c(F)c2)cn1] | 0.0025 | 513 | (d₆-DMSO) δ 9.44 (d, 1H), 9.22 (s, 1H), 8.04 (br s, 1H), 7.90 (d, 1H), 7.67 (d, 1H), 7.58 (m, 2H), 7.49 (d, 1H), 7.38 (s, 1H), 7.32 (d, 1H), 6.32 (d, 1H), 4.88 (br d, 1H), 4.26 (br d, 1H), 4.03 (m, 1H), 3.93 (d, 1H), 3.79 (s, 3H), 3.56 (m, 2H), 2.00 (m, 1H), 1.70 (d, 1H). |
| I-29 | 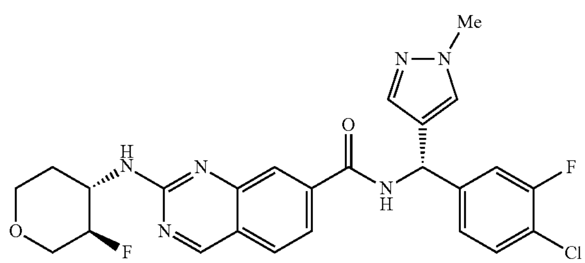 [SMILES: Cn1cc([C@@H](NC(=O)c2ccc3cnc(N[C@H]4CCOC[C@@H]4F)nc3c2)c2ccc(Cl)c(F)c2)cn1] | 0.0038 | 513 | (d₆-DMSO) δ 9.46 (d, 1H), 9.22 (s, 1H), 8.06 (br s, 1H), 7.88 (d, 1H), 7.82 (br s, 1H), 7.66 (d, 1H), 7.58 (m, 1H), 7.58 (s, 1H), 7.49 (d, 1H), 7.38 (s, 1H), 7.32 (d, 1H), 6.33 (d, 1H), 4.61 (br d, 1H), 4.38 (br s, 1H), 4.04 (m, 1H), 3.86 (d, 1H), 3.80 (s, 3H), 3.50 (m, 2H), 2.06 (m, 1H), 1.65 (d, 1H). |
| I-30 | 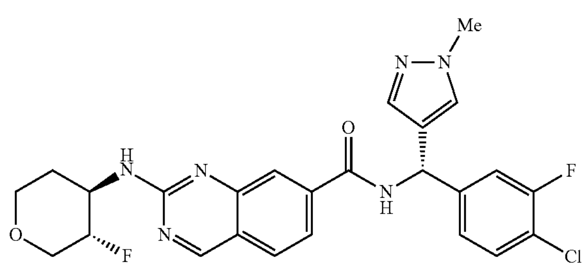 [SMILES: Cn1cc([C@@H](NC(=O)c2ccc3cnc(N[C@@H]4CCOC[C@H]4F)nc3c2)c2ccc(Cl)c(F)c2)cn1] | 0.0021 | 513 | (d₆-DMSO) δ 9.46 (d, 1H), 9.22 (s, 1H), 8.07 (br s, 1H), 7.88 (d, 1H), 7.66 (m, 1H), 7.58 (m, 2H), 7.49 (m, 1H), 7.38 (s, 1H), 7.32 (d, 1H), 6.32 (d, 1H), 4.61 (br d, 1H), 4.38 (br s, 1H), 4.04 (m, 1H), 3.86 (m, 1H), 3.80 (s, 3H), 3.45 (m, 2H), 2.06 (br d, 1H), 1.65 (m, 1H). |
| I-31 | 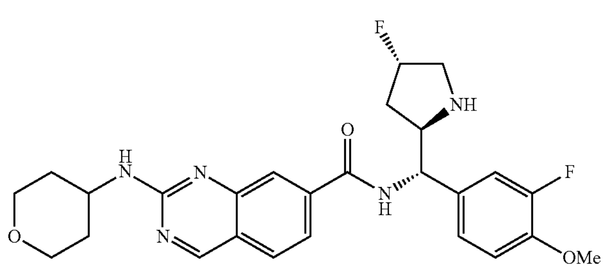 [SMILES: COc1ccc([C@H](NC(=O)c2ccc3cnc(NC4CCOCC4)nc3c2)[C@H]2C[C@H](F)CN2)cc1F] | 0.0017 | 498.5 | (CDCl₃) δ 9.01 (s, 1H), 7.94 (s, 1H), 7.70 (m, 2H), 7.11 (m, 1H), 7.09 (m, 2H), 6.95 (m, 1H), 5.25 (m, 2H), 5.22 (m, 1H), 4.23 (m, 1H), 4.03 (m, 2H), 3.88 (s, 3H), 3.68 (m, 1H), 3.61 (m, 2H), 3.39 (m, 1H), 2.93 (m, 1H), 2.13 (d, 2H), 2.00 (m, 1H), 1.62 (m, 2H) |

TABLE I-continued

| Cpd No. | Structure | IC50¹ (μM) | MS² | ¹H-NMR |
|---|---|---|---|---|
| I-32 | 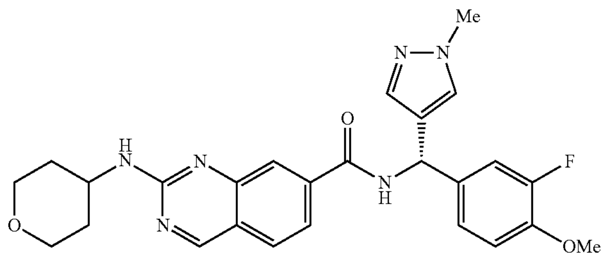 [SMILES: COc1ccc([C@H](NC(=O)c2ccc3cnc(NC4CCOCC4)nc3c2)c2cnn(C)c2)cc1F] | 0.0011 | 491 | (d₆-DMSO) δ 9.37 (d, 1H), 9.17 (s, 1H), 8.02 (s, 1H), 7.84 (m, 1H), 7.62 (m, 1H), 7.54 (m, 2H), 7.30 (m, 2H), 7.16 (m, 2H), 6.26 (m, 1H), 5.75 (m, 1H), 4.08 (br s, 1H), 3.90, (m, 2H), 3.82 (s, 3H), 3.79 (s, 3H), 3.42 (m, 2H), 1.90 (m, 2H), 1.58 (m, 2H). |
| I-33 | 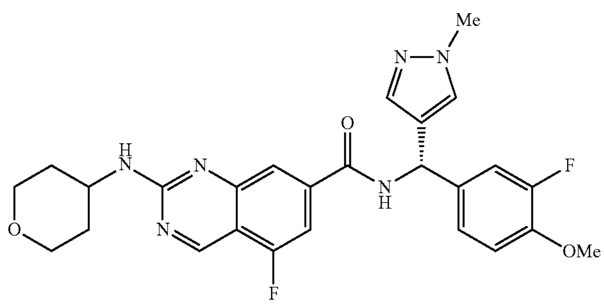 | 0.0015 | 509 | (d₆-DMSO) δ 9.41 (d, 1H), 9.30 (s, 1H), 7.93-7.85 (m, 2H), 7.54 (s, 1H), 7.38-7.25 (m, 3H), 7.22-7.11 (m, 2H), 6.25 (d, 1H), 4.15-4.05 (m, 1H), 3.93-3.85 (m, 2H), 3.72 (s, 3H), 3.69 (s, 3H), 3.47-3.38 (m, 2H), 1.93-1.85 (m, 2H), 1.64-1.53 (m, 2H). |
| I-34 | 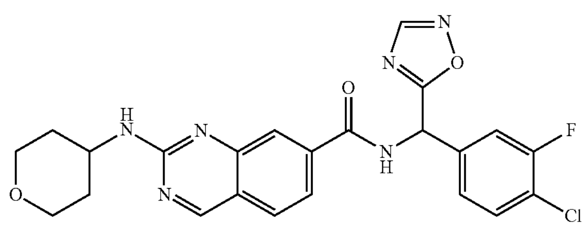 [SMILES: O=C(NC(c1ccc(Cl)c(F)c1)c1ncno1)c1ccc2cnc(NC3CCOCC3)nc2c1] | 0.0036 | 482.7 | (d₆-DMSO) δ 9.99 (d, 1H), 9.20 (s, 1H), 9.04 (s, 1H), 8.06 (s, 1H), 7.89 (d, 1H), 7.67 (m, 4H), 7.45 (d, 1H), 6.79 (d, 1H), 4.07 (br s, 1H), 3.90 (d, 2H), 3.42 (m, 2H), 1.89 (d, 2H), 1.57 (m, 2H). |
| I-35 | 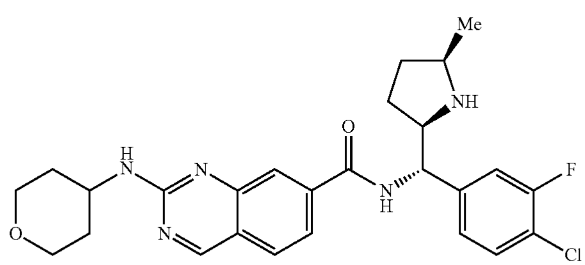 [SMILES: C[C@@H]1CC[C@H]([C@@H](NC(=O)c2ccc3cnc(NC4CCOCC4)nc3c2)c2ccc(Cl)c(F)c2)N1] | 0.0020 | 498.0 | (CDCl₃) δ 9.01 (s, 1H), 7.88 (s, 1H), 7.69 (m, 2H), 7.37 (m, 1H), 7.16 (d, 1H), 7.01 (d, 1H), 5.28 (d, 1H), 5.01 (m, 1H), 4.24 (m, 1H), 4.04 (m, 2H), 3.61 (m, 2H), 3.58 (m, 1H), 3.22 (m, 1H), 2.13 (d, 2H), 1.80 (m, 2H), 1.62 (m, 2H), 1.57 (m, 4H), 1.11 (d, 3H). |
| I-36 | 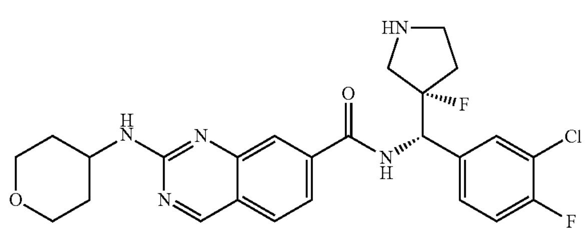 [SMILES: O=C(N[C@@H](c1ccc(F)c(Cl)c1)[C@]1(F)CCNC1)c1ccc2cnc(NC3CCOCC3)nc2c1] | 0.0016 | 502.2 | |

TABLE I-continued

| Cpd No. | Structure | IC50¹ (μM) | MS² | ¹H-NMR |
|---|---|---|---|---|
| I-37 | 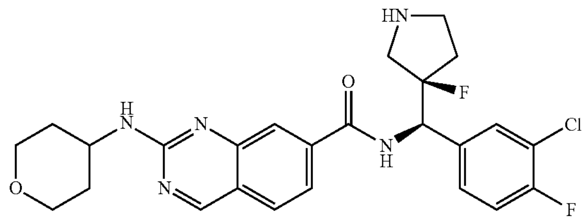 [SMILES: O=C(N[C@H](c1ccc(F)c(Cl)c1)[C@@]1(F)CCNC1)c1ccc2cnc(NC3CCOCC3)nc2c1] | 0.0736 | 502.1, 504.1³ | |
| I-38 | 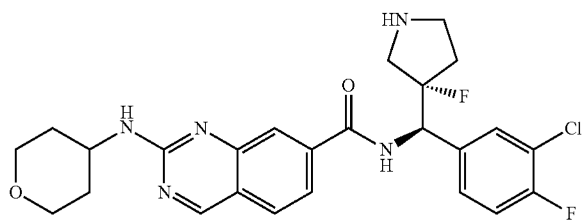 [SMILES: O=C(N[C@H](c1ccc(F)c(Cl)c1)[C@]1(F)CCNC1)c1ccc2cnc(NC3CCOCC3)nc2c1] | 0.0654 | 502.2 | |
| I-39 | 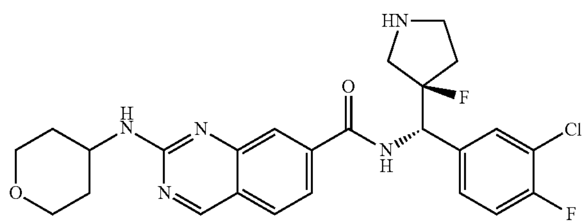 [SMILES: O=C(N[C@@H](c1ccc(F)c(Cl)c1)[C@@]1(F)CCNC1)c1ccc2cnc(NC3CCOCC3)nc2c1] | 0.0012 | 502.2 | |
| I-40 | 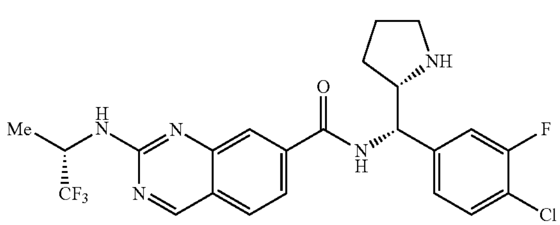 [SMILES: C[C@H](Nc1ncc2ccc(C(=O)N[C@@H](c3ccc(Cl)c(F)c3)[C@@H]3CCCN3)cc2n1)C(F)(F)F] | 0.0073 | 497.0 | |
| I-41 | 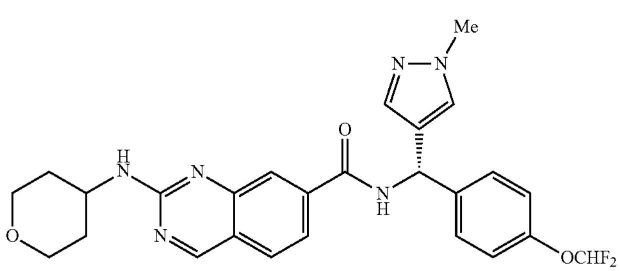 [SMILES: Cn1cc([C@@H](NC(=O)c2ccc3cnc(NC4CCOCC4)nc3c2)c2ccc(OC(F)F)cc2)cn1] | 0.00055 | 509.0 | (CDCl₃) δ 9.01 (s, 1H), 7.85 (s, 1H), 7.71 (m, 2H), 7.41 (m, 3H), 7.19 (s, 1H), 7.14 (m, 2H), 6.73 (d, 1H), 6.37 (d, 1H), 5.29 (d, 1H), 4.20 (m, 1H), 4.02 (m, 2H), 3.88 (s, 3H), 3.60 (m, 2H), 2.12 (d, 2H), 1.62 (m, 2H). |

TABLE I-continued

| Cpd No. | Structure | IC50 (μM) | MS | 1H-NMR |
|---|---|---|---|---|
| I-42 | 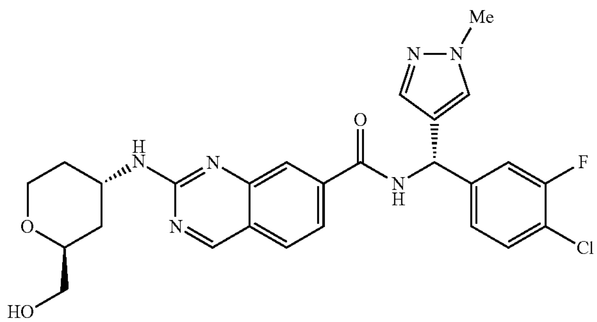 [SMILES: Cn1cc([C@@H](NC(=O)c2ccc3cnc(N[C@H]4CCO[C@H](CO)C4)nc3c2)c2ccc(Cl)c(F)c2)cn1] | 0.0072 | 525.2 | (CDCl₃) δ 9.03 (s, 1H), 7.86 (s, 1H), 7.72 (dd, 2H), 7.40 (m, 1H), 7.39 (s, 1H), 7.20 (s, 1H), 7.17 (m, 2H), 6.72 (d, 1H), 6.33 (d, 1H), 5.63 (d, 1H), 4.48 (m, 1H), 3.97 (m, 1H), 3.89 (s, 3H), 3.79 (m, 2H), 3.59 (m, 2H), 2.02 (m, 2H), 1.88 (m, 2H), 1.78 (m, 1H). |
| I-43 | 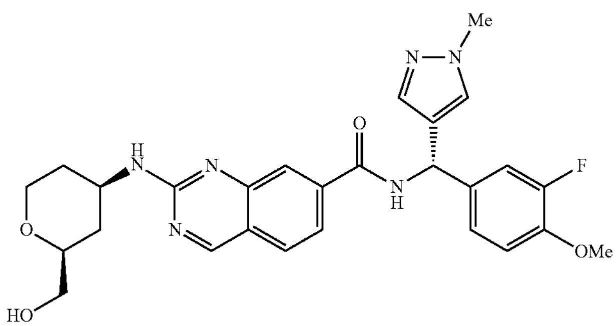 [SMILES: COc1ccc([C@H](NC(=O)c2ccc3cnc(N[C@@H]4CCO[C@H](CO)C4)nc3c2)c2cnn(C)c2)cc1F] | | 521.2 | (DMSO) 9.33 (t, J = 10.4 Hz, 1H), 9.14 (d, J = 15.8 Hz, 1H), 8.01 (s, 1H), 7.89-7.79 (m, 1H), 7.61 (t, J = 9.2 Hz, 1H), 7.56-7.40 (m, 2H), 7.32 (d, J = 9.4 Hz, 1H), 7.26 (t, J = 11.7 Hz, 1H), 7.20 (d, J = 8.8 Hz, 1H), 7.12 (dd, J = 16.9, 8.4 Hz, 1H), 6.25 (t, J = 12.6 Hz, 1H), 4.60 (d, J = 19.4 Hz, 1H), 4.12 (d, J = 7.7 Hz, 1H), 3.95 (dd, J = 11.5, 3.8 Hz, 1H), 3.82 (s, 4H), 3.79 (s, 4H), 3.44 (dd, J = 18.5, 7.7 Hz, 2H), 1.92 (dd, J = 29.5, 12.4 Hz, 2H), 1.51 (qd, J = 12.3, 4.5 Hz, 1H), 1.24 (q, J = 11.6 Hz, 1H). |
| I-44 | 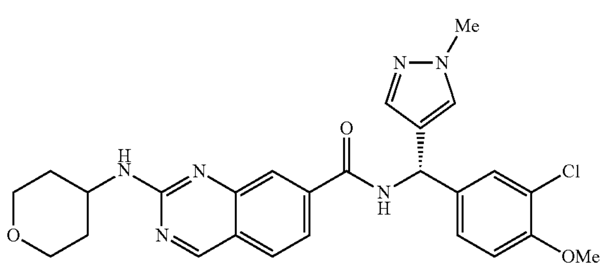 [SMILES: COc1ccc([C@H](NC(=O)c2ccc3cnc(NC4CCOCC4)nc3c2)c2cnn(C)c2)cc1Cl] | 0.001 | 507.2 | (DMSO-d₆) δ 9.40 (d, J = 8.5 Hz, 1H), 9.17 (s, 1H), 8.03 (s, 1H), 7.85 (d, J = 8.0 Hz, 1H), 7.63 (m, 1H), 7.58-7.55 (m, 2H), 7.48 (d, J = 2.0 Hz, 1H), 7.38-7.35 (m, 2H), 7.13 (d, J = 8.5 Hz, 1H), 6.27 (d, J = 8.5 Hz, 1H), 4.09 (m, 1H), 3.91-3.89 (m, 2H), 3.84 (s, 3H), 3.80 (s, 3H), 3.44-3.40 (m, 2H), 1.90-1.88 (m, 2H), 1.61-1.54 (m, 2H). |
| I-45 | 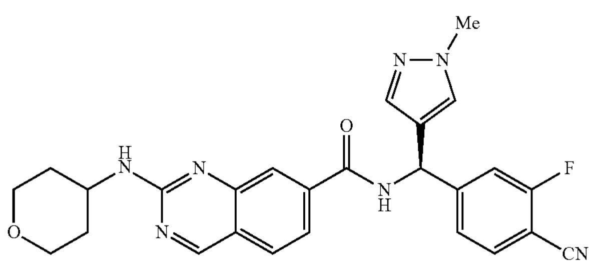 [SMILES: Cn1cc([C@H](NC(=O)c2ccc3cnc(NC4CCOCC4)nc3c2)c2ccc(C#N)c(F)c2)cn1] | 0.022 | 502.1 | (MeOH-d₄) δ 9.11 (s, 1H), 8.00 (s, 1H), 7.87-7.84 (m, 2H), 7.71 (s, 1H), 7.64 (m, 1H), 7.59-7.56 (m, 2H), 7.45 (s, 1H), 6.44 (s, 1H), 4.19 (m, 1H), 4.03-4.01 (m, 2H), 3.89 (s, 3H), 3.62-3.57 (m, 2H), 2.07-2.05 (m, 2H), 1.69-1.65 (m, 2H). |

TABLE I-continued

[Structure diagram: quinazoline core with R²HN at position 2, R³ at position 5, and C(O)NH-CHR¹Ar at position 7, with positions numbered 1, 2, 4, 5, 6, 7, 8]

| Cpd No. | Structure | IC50 (μM) | MS | ¹H-NMR |
|---------|-----------|-----------|-----|--------|
| I-46 | 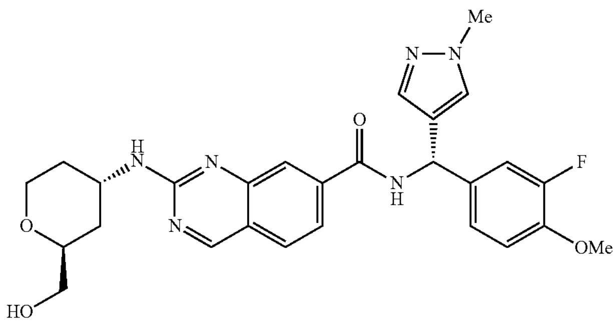 [SMILES: COc1ccc([C@H](NC(=O)c2ccc3cnc(N[C@H]4CCO[C@H](CO)C4)nc3c2)c2cnn(C)c2)cc1F] | 0.0042 | 521.2 | (DMSO) 9.34 (d, J = 8.6 Hz, 1H), 9.19 (s, 1H), 8.01 (s, 1H), 7.86 (d, J = 8.3 Hz, 1H), 7.72 (d, J = 6.4 Hz, 1H), 7.64 (d, J = 8.3 Hz, 1H), 7.55 (d, J = 8.5 Hz, 1H), 7.35-7.25 (m, 2H), 7.16 (dt, J = 17.2, 8.6 Hz, 2H), 6.27 (d, J = 8.5 Hz, 1H), 4.51 (s, 1H), 4.33 (s, 1H), 4.17-3.94 (m, 2H), 3.82 (t, J = 11.8 Hz, 8H), 3.70 (dd, J = 16.9, 10.0 Hz, 2H), 1.83 (t, J = 14.8 Hz, 2H), 1.72 (d, J = 14.2 Hz, 1H), 1.59-1.49 (m, 1H). |
| I-47 | 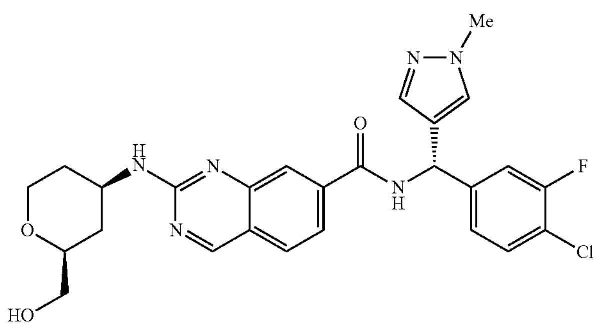 [SMILES: Cn1cc([C@@H](NC(=O)c2ccc3cnc(N[C@@H]4CCO[C@H](CO)C4)nc3c2)c2ccc(Cl)c(F)c2)cn1] | 0.0014 | 525.5 | |
| I-48 | 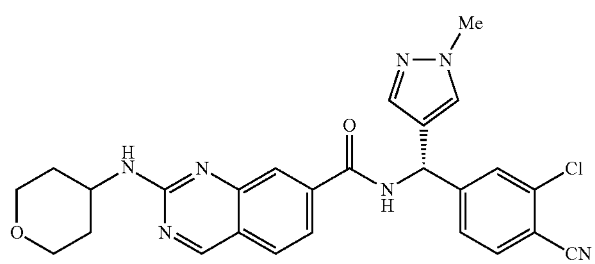 [SMILES: Cn1cc([C@@H](NC(=O)c2ccc3cnc(NC4CCOCC4)nc3c2)c2ccc(C#N)c(Cl)c2)cn1] | 0.0011 | 502.2 | |
| I-49 | 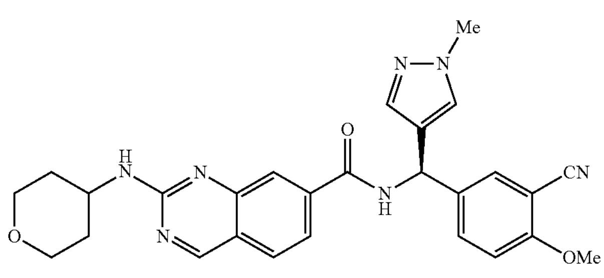 [SMILES: COc1ccc([C@@H](NC(=O)c2ccc3cnc(NC4CCOCC4)nc3c2)c2cnn(C)c2)cc1C#N] | 0.141 | 498.2 | |

TABLE I-continued
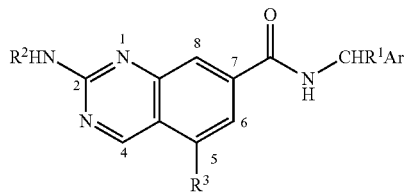
| Cpd No. | Structure | IC50[1] (μM) | MS[2] | $^1$H-NMR |
|---|---|---|---|---|
| I-50 | 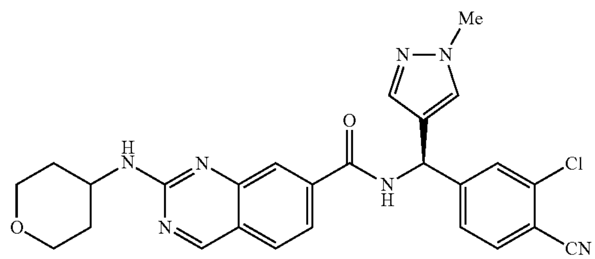 [SMILES: Cn1cc([C@H](NC(=O)c2ccc3cnc(NC4CCOCC4)nc3c2)c2ccc(C#N)c(Cl)c2)cn1] | 0.025 | 502.2 | |
| I-51 | 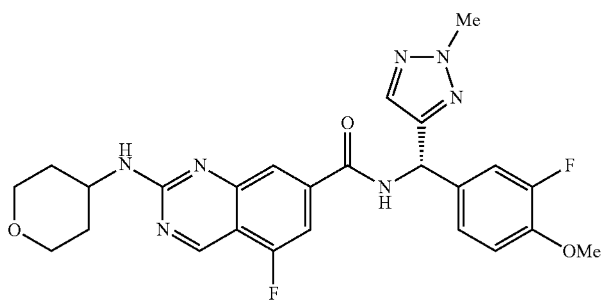 [SMILES: COc1ccc([C@H](NC(=O)c2cc(F)c3cnc(NC4CCOCC4)nc3c2)c2cnn(C)n2)cc1F] | 0.0028 | 510.2 | |
| I-52 | 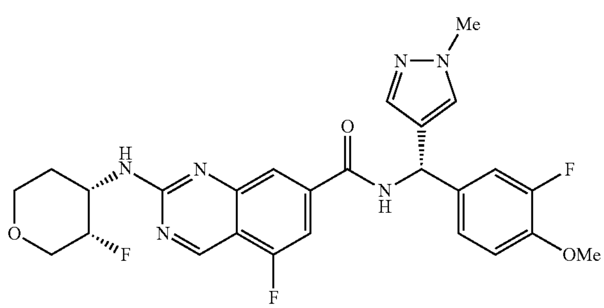 [SMILES: COc1ccc([C@H](NC(=O)c2cc(F)c3cnc(N[C@H]4CCOC[C@H]4F)nc3c2)c2cnn(C)c2)cc1F] | 0.0026 | 527.2 | $^1$H NMR (400 MHz, DMSO) δ 9.60 (d, J = 8.2 Hz, 1H), 9.30 (s, 1H), 7.89 (m, 2H), 7.63 (s, 1H), 7.33 (dd, J = 22.1, 10.8 Hz, 2H), 7.18 (dt, J = 17.2, 8.6 Hz, 2H), 6.44 (d, J = 8.4 Hz, 1H), 4.10 (m, 4H), 3.90 (d, J = 11.4 Hz, 2H), 3.82 (s, 3H), 3.42 (t, J = 11.3 Hz, 2H), 1.89 (m, 2H), 1.59 (qd, J = 12.0, 4.2 Hz, 2H). |
| I-53 | 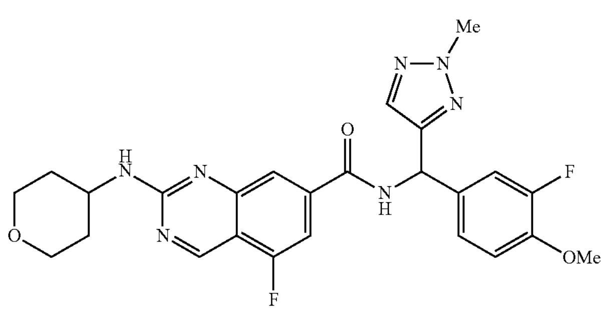 [SMILES: COc1ccc(C(NC(=O)c2cc(F)c3cnc(NC4CCOCC4)nc3c2)c2cnn(C)n2)cc1F] | 0.0068 | 510.2 | |

TABLE I-continued

| Cpd No. | Structure | IC50 (μM) | MS | ¹H-NMR |
|---|---|---|---|---|
| I-54 | 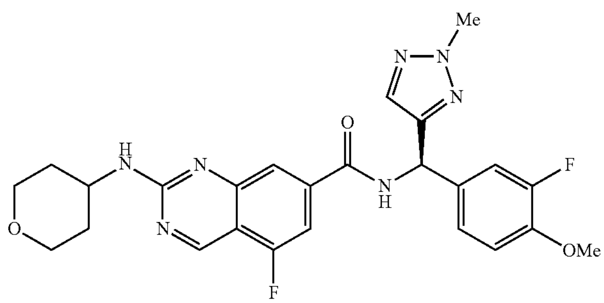 [SMILES: COc1ccc([C@@H](NC(=O)c2cc(F)c3cnc(NC4CCOCC4)nc3c2)c2cnn(C)n2)cc1F] | 0.031 | 510.2 | |
| I-55 | 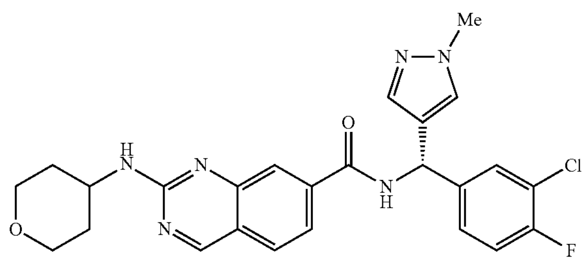 | 0.0027 | 495.2 | |
| I-56 | 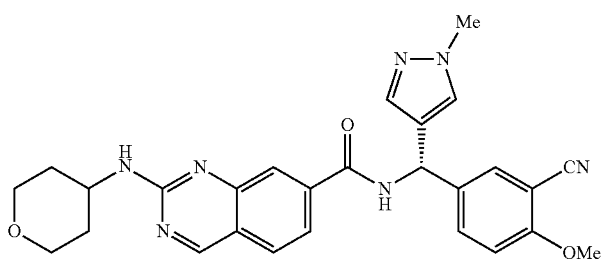 [SMILES: COc1ccc([C@H](NC(=O)c2ccc3cnc(NC4CCOCC4)nc3c2)c2cnn(C)c2)cc1C#N] | 0.0035 | 498.2 | |
| I-57 | 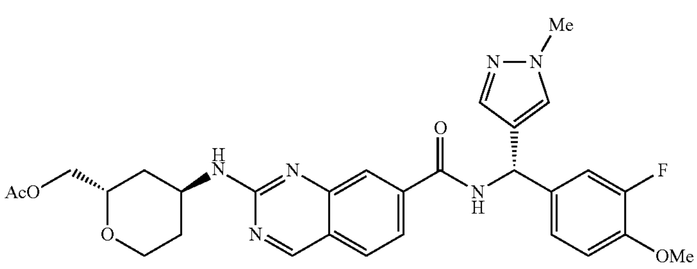 [SMILES: COc1ccc([C@H](NC(=O)c2ccc3cnc(N[C@H]4CCO[C@H](COC(C)=O)C4)nc3c2)c2cnn(C)c2)cc1F] | 0.024 | 563.2 | (DMSO) 9.34 (d, J = 8.6 Hz, 1H), 9.20 (s, 1H), 8.02 (s, 1H), 7.87 (d, J = 8.3 Hz, 1H), 7.78 (d, J = 6.5 Hz, 1H), 7.65 (d, J = 8.3 Hz, 1H), 7.54 (s, 1H), 7.36-7.24 (m, 2H), 7.16 (dt, J = 17.2, 8.6 Hz, 2H), 6.26 (d, J = 8.5 Hz, 1H), 4.34 (s, 1H), 4.01 (ddd, J = 31.9, 17.1, 7.3 Hz, 4H), 3.80 (d, J = 12.8 Hz, 7H), 3.73 (d, J = 11.2 Hz, 1H), 2.02 (s, 3H), 1.82 (d, J = 12.0 Hz, 2H), 1.75 (d, J = 13.5 Hz, 1H), 1.63 (dd, J = 17.0, 7.0 Hz, 1H). |

TABLE I-continued
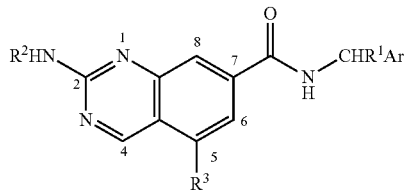
| Cpd No. | Structure | IC50[1] (μM) | MS[2] | $^1$H-NMR |
|---|---|---|---|---|
| I-58 | 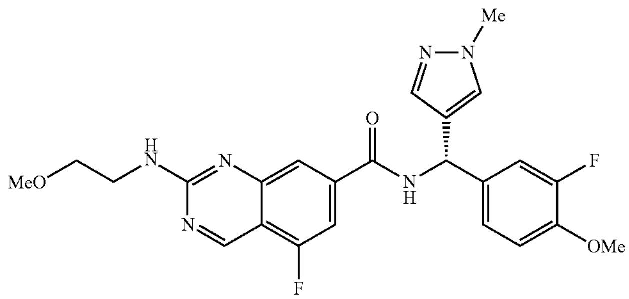 [SMILES: COCCNc1ncc2c(F)cc(C(=O)N[C@@H](c3ccc(OC)c(F)c3)c3cnn(C)c3)cc2n1] | 0.020 | 483.2 | (DMSO) 9.40 (d, J = 8.3 Hz, 1H), 9.29 (s, 1H), 7.91 (s, 1H), 7.82 (s, 1H), 7.54 (s, 1H), 7.36 (d, J = 10.3 Hz, 1H), 7.32 (s, 1H), 7.27 (dd, J = 12.6, 1.9 Hz, 1H), 7.21-7.17 (m, 1H), 7.14 (t, J = 8.6 Hz, 1H), 6.25 (d, J = 8.4 Hz, 1H), 3.82 (s, 3H), 3.79 (s, 3H), 3.57 (m, 4H), 3.28 (s, 3H). |
| I-59 | 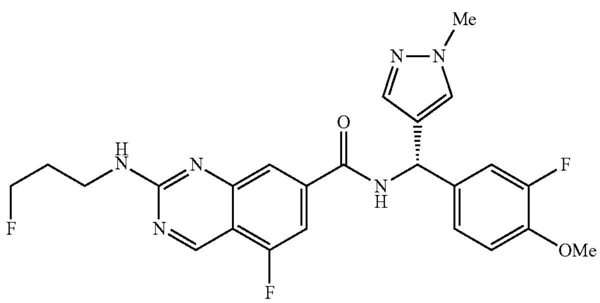 [SMILES: COc1ccc([C@H](NC(=O)c2cc(F)c3cnc(NCCCF)nc3c2)c2cnn(C)c2)cc1F] | 0.015 | 485.2 | (DMSO) 9.40 (d, J = 8.4 Hz, 1H), 9.29 (s, 1H), 7.91 (bs, 2H), 7.54 (s, 1H), 7.36 (d, J = 10.6 Hz, 1H), 7.32 (s, 1H), 7.27 (dd, J = 12.6, 1.9 Hz, 1H), 7.20 (dd, J = 8.6, 1.8 Hz, 1H), 7.14 (t, J = 8.6 Hz, 1H), 6.25 (d, J = 8.4 Hz, 1H), 4.56 (dt, J = 47.4, 5.8 Hz, 2H), 3.82 (s, 3H), 3.79 (s, 3H), 3.49 (m, 2H), 2.10-1.87 (m, 2H). |
| I-60 | 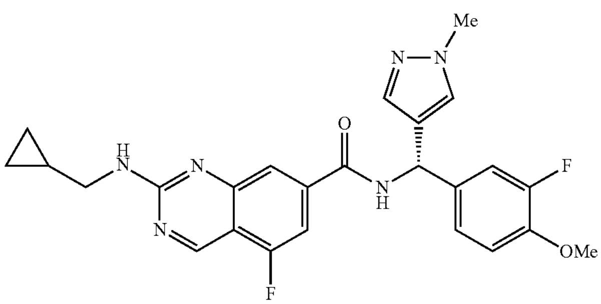 [SMILES: COc1ccc([C@H](NC(=O)c2cc(F)c3cnc(NCC4CC4)nc3c2)c2cnn(C)c2)cc1F] | 0.006 | 479.2 | (DMSO) 9.39 (d, J = 8.5 Hz, 1H), 9.28 (s, 1H), 7.92 (m, 2H), 7.54 (s, 1H), 7.34 (m, 2H), 7.27 (dd, J = 12.6, 1.9 Hz, 1H), 7.22-7.17 (m, 1H), 7.14 (t, J = 8.6 Hz, 1H), 6.24 (d, J = 8.4 Hz, 1H), 3.82 (s, 3H), 3.79 (s, 3H), 3.25 (m, 2H), 1.15 (m, 1H), 0.49-0.40 (m, 2H), 0.26 (m, 2H). |
| I-61 | 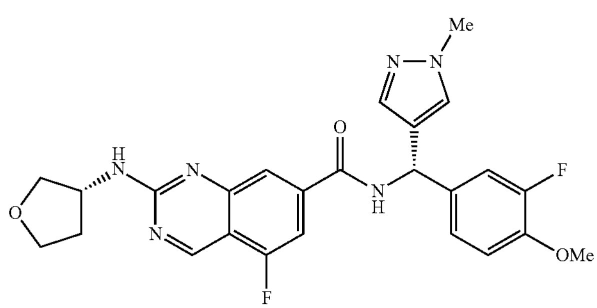 [SMILES: COc1ccc([C@H](NC(=O)c2cc(F)c3cnc(N[C@@H]4CCOC4)nc3c2)c2cnn(C)c2)cc1F] | 0.002 | 495.2 | (DMSO) 9.41 (d, J = 8.5 Hz, 1H), 9.31 (s, 1H), 8.09 (s, 1H), 7.91 (s, 1H), 7.54 (s, 1H), 7.38 (d, J = 10.5 Hz, 1H), 7.33 (s, 1H), 7.27 (dd, J = 12.6, 1.8 Hz, 1H), 7.22-7.17 (m, 1H), 7.14 (t, J = 8.6 Hz, 1H), 6.25 (d, J = 8.4 Hz, 1H), 4.51 (s, 1H), 3.94 (dd, J = 8.8, 6.1 Hz, 1H), 3.87 (dd, J = 15.2, 7.4 Hz, 1H), 3.82 (s, 3H), 3.79 (s, 3H), 3.75 (m, 1H), 3.64 (m, 1H), 2.20 (m, 7.6 Hz, 1H), 1.96 (m, 1H). |

TABLE I-continued

| Cpd No. | Structure | IC50¹ (µM) | MS² | ¹H-NMR |
|---|---|---|---|---|
| I-62 | 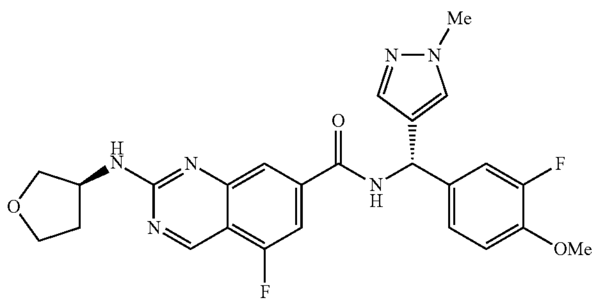 [SMILES: COc1ccc([C@H](NC(=O)c2cc(F)c3cnc(N[C@H]4CCOC4)nc3c2)c2cnn(C)c2)cc1F] | 0.004 | 495.2 | (DMSO) 9.41 (d, J = 8.5 Hz, 1H), 9.31 (s, 1H), 8.09 (s, 1H), 7.91 (s, 1H), 7.54 (s, 1H), 7.38 (d, J = 10.4 Hz, 1H), 7.32 (s, 1H), 7.27 (d, J = 12.7 Hz, 1H), 7.20 (d, J = 10.0 Hz, 1H), 7.14 (t, J = 8.5 Hz, 1H), 6.25 (d, J = 8.4 Hz, 1H), 4.50 (s, 1H), 3.96-3.90 (m, 1H), 3.86 (t, J = 7.5 Hz, 1H), 3.82 (s, 3H), 3.79 (s, 3H), 3.75 (m, 1H), 3.67-3.59 (m, 1H), 2.20 (m, 1H), 1.97 (m, 1H). |
| I-63 | 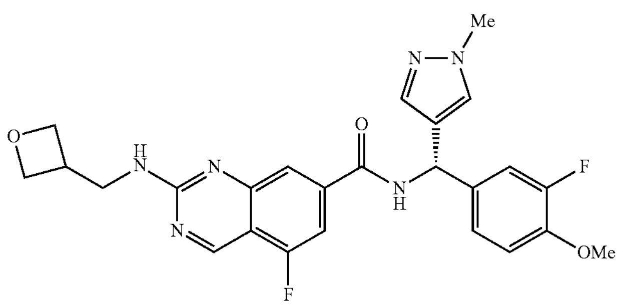 [SMILES: COc1ccc([C@H](NC(=O)c2cc(F)c3cnc(NCC4COC4)nc3c2)c2cnn(C)c2)cc1F] | 0.004 | 495.2 | (DMSO) 9.40 (d, J = 8.5 Hz, 1H), 9.29 (s, 1H), 8.02 (s, 1H), 7.92 (s, 1H), 7.54 (s, 1H), 7.37 (d, J = 10.4 Hz, 1H), 7.32 (s, 1H), 7.27 (dd, J = 12.6, 1.7 Hz, 1H), 7.20 (d, J = 8.6 Hz, 1H), 7.14 (t, J = 8.6 Hz, 1H), 6.25 (d, J = 8.4 Hz, 1H), 4.70-4.62 (m, 2H), 4.37 (t, J = 5.9 Hz, 2H), 3.82 (s, 3H), 3.79 (s, 3H), 3.68 (t, J = 6.2 Hz, 2H), 3.26 (m, 1H). |
| I-64 | 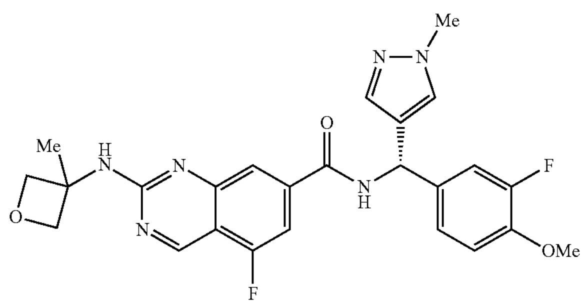 [SMILES: COc1ccc([C@H](NC(=O)c2cc(F)c3cnc(NC4(C)COC4)nc3c2)c2cnn(C)c2)cc1F] | 0.006 | 495.2 | (DMSO) 9.41 (d, J = 8.4 Hz, 1H), 9.33 (s, 1H), 8.30 (s, 1H), 7.81 (s, 1H), 7.53 (s, 1H), 7.41 (d, J = 10.4 Hz, 1H), 7.32 (s, 1H), 7.27 (dd, J = 12.6, 1.8 Hz, 1H), 7.21-7.17 (m, 1H), 7.14 (t, J = 8.5 Hz, 1H), 6.24 (d, J = 8.4 Hz, 1H), 4.74 (d, J = 6.2 Hz, 2H), 4.46 (d, J = 6.2 Hz, 2H), 3.82 (s, 3H), 3.79 (s, 3H), 1.69 (s, 3H). |
| I-65 | 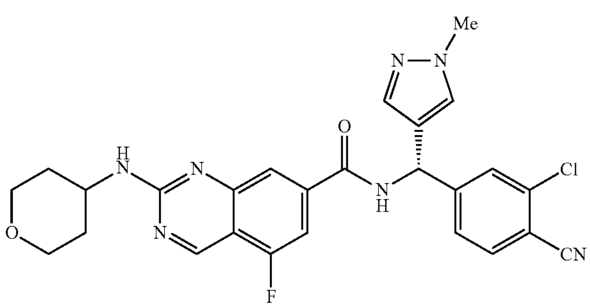 [SMILES: Cn1cc([C@@H](NC(=O)c2cc(F)c3cnc(NC4CCOCC4)nc3c2)c2ccc(C#N)c(Cl)c2)cn1] | 0.0006 | 520.2 | |

TABLE I-continued
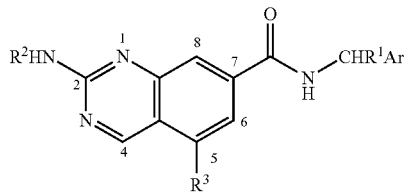
| Cpd No. | Structure | IC50¹ (μM) | MS² | ¹H-NMR |
|---|---|---|---|---|
| I-66 | 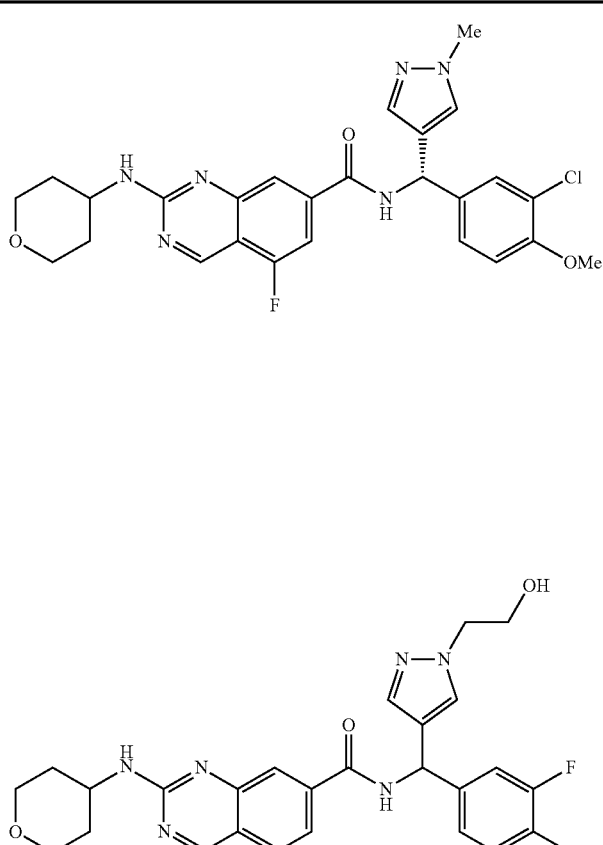 | 0.0006 | 525.2 | |
| I-67 | 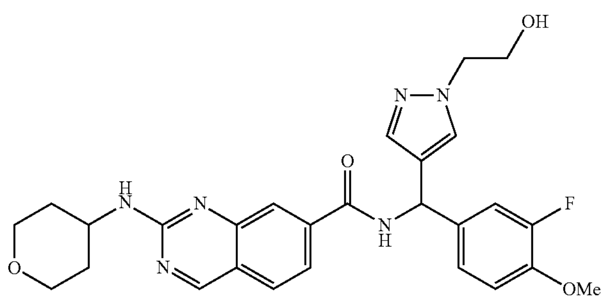 [SMILES: COc1ccc(C(NC(=O)c2ccc3cnc(NC4CCOCC4)nc3c2)c2cnn(CCO)c2)cc1F] | 0.005 | 521.2 | (DMSO-d₆) δ 9.10 (s, 1H), 7.97 (s, 1H), 7.86 (d, J = 9.0 Hz, 1H), 7.64 (d, J = 8.5 Hz, 1H), 7.56 (s, 1H), 7.44 (s, 1H), 7.22 (m, 2H), 7.13 (m, 1H), 6.36 (s, 1H), 4.22 (m, 3H), 4.03 (m, 2H), 3.89 (m, 5H), 3.61 (m, 2H), 2.07 (m, 2H), 1.68 (m, 2H). |
| I-68 | 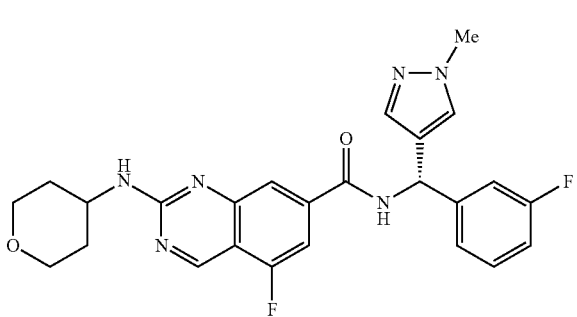 [SMILES: Cn1cc([C@@H](NC(=O)c2cc(F)c3cnc(NC4CCOCC4)nc3c2)c2cccc(F)c2)cn1] | 0.0013 | 479.2 | ¹H NMR (400 MHz, DMSO) δ 9.46 (d, J = 8.4 Hz, 1H), 9.30 (s, 1H), 7.92 (s, 1H), 7.84 (d, J = 1H), 7.56 (s, 1H), 7.44-7.33 (m, 3H), 7.30-7.23 (m, 2H), 7.10 (td, J = 8.8, 2.4 Hz, 1H), 6.32 (d, J = 8.3 Hz, 1H), 4.10 (br s, 1H), 3.90 (d, J = 11.1 Hz, 2H), 3.79 (s, 3H), 3.42 (t, J = 11.1 Hz, 2H), 1.89 (d, J = 11.5 Hz, 2H), 1.59 (qd, J = 11.4, 4 Hz, 2H). |

TABLE I-continued

| Cpd No. | Structure | IC50¹ (µM) | MS² | ¹H-NMR |
|---|---|---|---|---|
| I-69 | 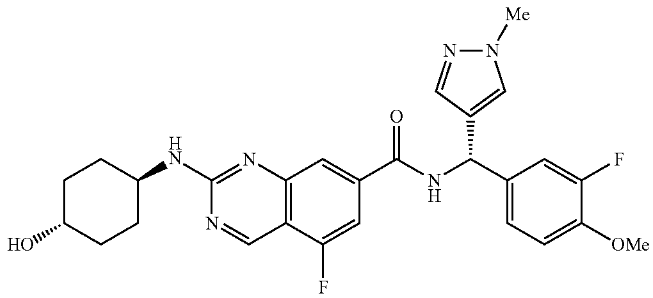 [SMILES: COc1ccc([C@H](NC(=O)c2cc(F)c3cnc(N[C@H]4CC[C@H](O)CC4)nc3c2)c2cnn(C)c2)cc1F] | 0.0012 | 523.2 | ¹H NMR (400 MHz, DMSO) δ 9.40 (d, J = 8.0 Hz, 1H), 9.25 (s, 1H), 7.91 (s, 1H), 7.68 (br d, J = 6.8 Hz, 1H), 7.54 (s, 1H), 7.33 (d, J = 9.6 Hz, 1H), 7.32 (s, 1H), 7.27 (dd, J = 12.6, 1.9 Hz, 1H), 7.20 (dd, J = 8.8, 1.6 Hz, 1H), 7.14 (t, J = 8.6 Hz, 1H), 6.25 (d, J = 8.4 Hz, 1H), 4.54 (d, J = 4.3 Hz, 1H), 3.88-3.76 (m, 1H), 3.82 (s, 3H), 3.79 (s, 3H), 3.48-3.37 (m, 1H), 1.98-1.82 (m, 4H), 1.43-1.20 (m, 4H). |
| I-70 | 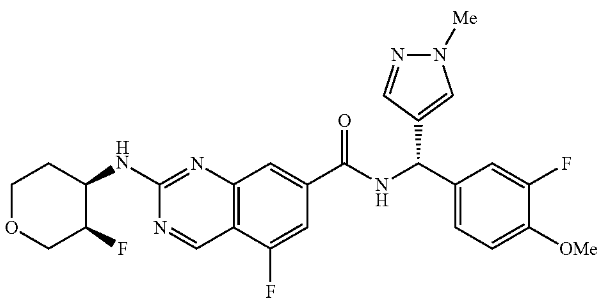 [SMILES: COc1ccc([C@H](NC(=O)c2cc(F)c3cnc(N[C@@H]4CCOC[C@@H]4F)nc3c2)c2cnn(C)c2)cc1F] | 0.004 | 527.2 | ¹H NMR (400 MHz, DMSO) δ 9.41 (d, J = 8.5 Hz, 1H), 9.35 (s, 1H), 7.93 (d, J = 8.5 Hz, 1H), 7.91 (s, 1H), 7.53 (s, 1H), 7.40 (d, J = 10.4 Hz, 1H), 7.33 (s, 1H), 7.28 (dd, J = 12.6, 1.8 Hz, 1H), 7.19 (d, J = 8.6 Hz, 1H), 7.14 (t, J = 8.5 Hz, 1H), 6.25 (d, J = 8.4 Hz, 1H), 4.88 (d, J = 48.8 Hz, 1H), 4.26 (m, 1H), 4.03 (t, J = 12.4 Hz, 1H), 3.93 (m, 1H), 3.82 (s, 3H), 3.79 (s, 3H), 3.69-3.47 (m, 2H), 2.01 (m, 1H), 1.70 (d, J = 9.4 Hz, 1H). |

¹ERK-2 Enzymatic Assay (Example 9)
²APCI-pos m/z (M + 1)
³m/z (M + 1), (M + 3)

Other representative compounds within the scope of the present invention are compiled in TABLE II. These examples are illustrative and should not be considered as limiting the scope of the invention, but merely as representative thereof. Compounds in TABLE II are prepared using methodology extensively described in the Examples which follow and are fully enabled.

TABLE II

| Cpd. No. | Structure | MS | IC50¹ (µM) | ¹H NMR (400 MHz, DMSO-d₆) |
|---|---|---|---|---|
| II-1 | 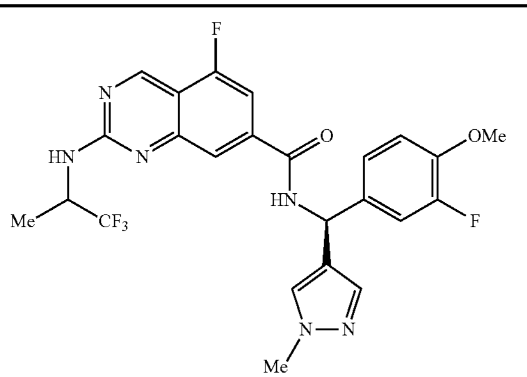 | 521.1 | 0.0062 | δ 9.44 (d, J = 8.4 Hz, 1H), 9.41 (s, 1H), 8.39 (s, 1H), 7.98 (s, 1H), 7.54 (s, 1H), 7.45 (d, J = 10.3 Hz, 1H), 7.32 (s, 1H), 7.28 (dd, J = 12.6, 1.8 Hz, 1H), 7.22-7.17 (m, 1H), 7.14 (t, J = 8.6 Hz, 1H), 6.25 (d, J = 8.4 Hz, 1H), 5.07 (m, 1H), 3.82 (s, 3H), 3.79 (s, 3H), 1.40 (d, J = 7.0 Hz, 3H). |

TABLE II-continued

| Cpd. No. | Structure | MS | IC50[1] (μM) | $^1$H NMR (400 MHz, DMSO-d$_6$) |
|---|---|---|---|---|
| II-2 | 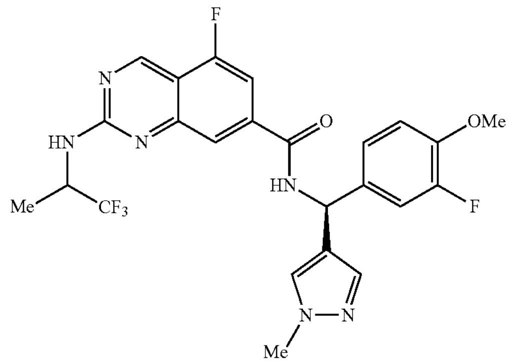 [SMILES: COc1ccc([C@H](NC(=O)c2cc(F)c3cnc(NC(C)C(F)(F)F)nc3c2)c2cnn(C)c2)cc1F] | 521.1 | 0.0136 | δ 9.44 (d, J = 8.5 Hz, 1H), 9.41 (s, 1H), 8.40 (s, 1H), 7.96 (s, 1H), 7.54 (s, 1H), 7.45 (d, J = 10.4 Hz, 1H), 7.33 (s, 1H), 7.27 (dd, J = 12.6, 1.8 Hz, 1H), 7.20 (d, J = 8.6 Hz, 1H), 7.14 (t, J = 8.6 Hz, 1H), 6.24 (d, J = 8.4 Hz, 1H), 5.07 (m, 1H), 3.82 (s, 3H), 3.79 (s, 3H), 1.40 (d, J = 7.0 Hz, 3H). |
| II-3 | 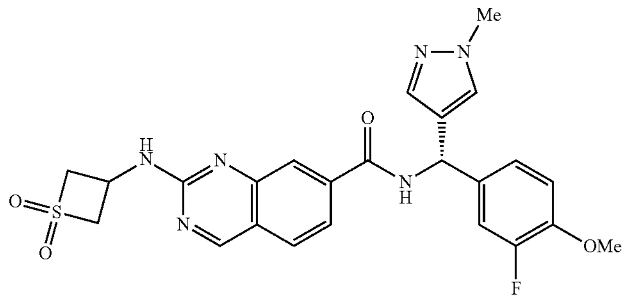 [SMILES: COc1ccc([C@H](NC(=O)c2ccc3cnc(NC4CS(=O)(=O)C4)nc3c2)c2cnn(C)c2)cc1F] | 511.1 | 0.0528 | δ 9.40 (d, J = 8.5 Hz, 1H), 9.28 (s, 1H), 8.30 (s, 1H), 8.07 (s, 1H), 7.94 (d, J = 8.3 Hz, 1H), 7.72 (dd, J = 8.3, 1.3 Hz, 1H), 7.54 (s, 1H), 7.37-7.24 (m, 2H), 7.17 (dt, J = 17.2, 8.6 Hz, 2H), 6.27 (d, J = 8.5 Hz, 1H), 4.61 (d, J = 9.3 Hz, 3H), 4.27 (dd, J = 9.7, 6.8 Hz, 2H), 3.82 (s, 3H), 3.79 (s, 3H). |
| II-4 | 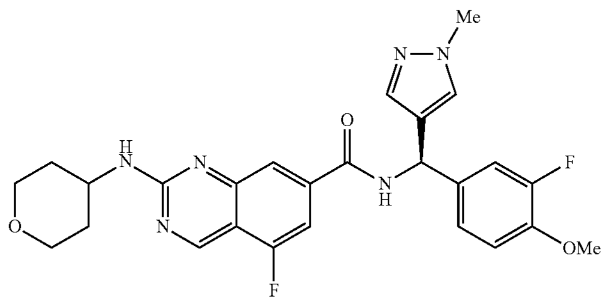 [SMILES: COc1ccc([C@@H](NC(=O)c2cc(F)c3cnc(NC4CCOCC4)nc3c2)c2cnn(C)c2)cc1F] | 509.2 | 0.0157 | |
| II-5 | 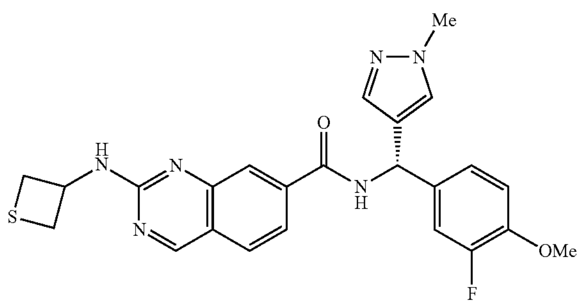 [SMILES: COc1ccc([C@H](NC(=O)c2ccc3cnc(NC4CSC4)nc3c2)c2cnn(C)c2)cc1F] | 479.1 | 0.013 | δ 9.37 (d, J = 8.6 Hz, 1H), 9.22 (s, 1H), 8.23 (d, J = 7.3 Hz, 1H), 8.05 (s, 1H), 7.88 (d, J = 8.3 Hz, 1H), 7.67 (dd, J = 8.3, 1.4 Hz, 1H), 7.55 (s, 1H), 7.35-7.25 (m, 2H), 7.23-7.18 (m, 1H), 7.14 (t, J = 8.6 Hz, 1H), 6.26 (d, J = 8.5 Hz, 1H), 5.34 (dd, J = 16.8, 8.4 Hz, 1H), 3.81 (d, J = 11.9 Hz, 6H), 3.51 (t, J = 9.1 Hz, 2H), 3.35-3.32 (m, 2H). |
| II-6 | 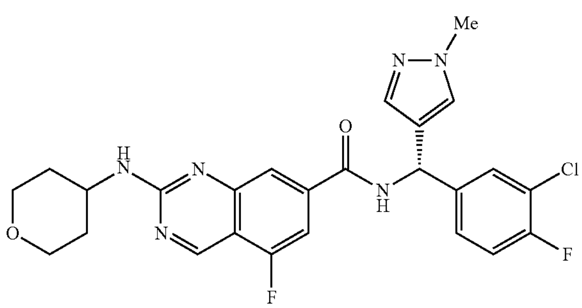 [SMILES: Cn1cc([C@@H](NC(=O)c2cc(F)c3cnc(NC4CCOCC4)nc3c2)c2ccc(F)c(Cl)c2)cn1] | 509.2 | 0.157 | |

TABLE II-continued

| Cpd. No. | Structure | MS | IC50[1] (μM) | $^1$H NMR (400 MHz, DMSO-d$_6$) |
|---|---|---|---|---|
| II-7 | 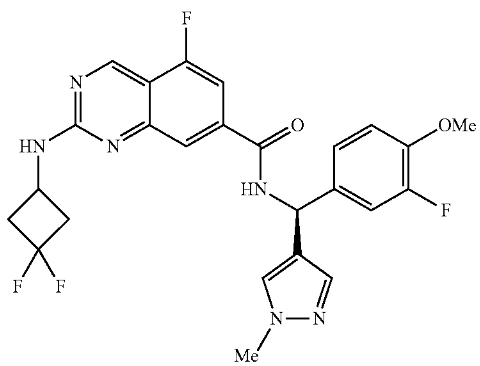 [SMILES: COc1ccc([C@H](NC(=O)c2cc(F)c3cnc(NC4CC(F)(F)C4)nc3c2)c2cnn(C)c2)cc1F] | 479.1 | 0.0056 | δ 9.41 (d, J = 8.5 Hz, 1H), 9.35 (s, 1H), 8.34 (s, 1H), 7.94 (s, 1H), 7.54 (s, 1H), 7.41 (d, J = 10.5 Hz, 1H), 7.33 (s, 1H), 7.27 (dd, J = 12.6, 1.9 Hz, 1H), 7.22-7.18 (m, 1H), 7.14 (t, J = 8.6 Hz, 1H), 6.25 (d, J = 8.4 Hz, 1H), 4.32 (s, 1H), 3.82 (s, 3H), 3.79 (s, 3H), 3.08-2.95 (m, 2H), 2.81-2.63 (m, 3H). |
| II-8 | 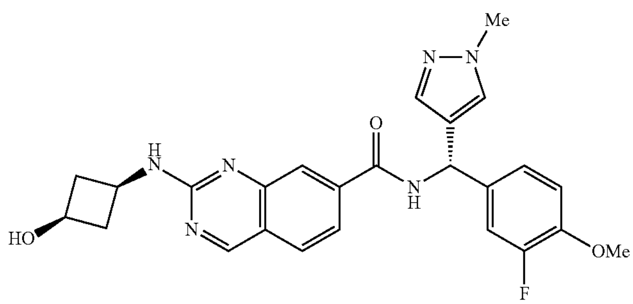 [SMILES: COc1ccc([C@H](NC(=O)c2ccc3cnc(N[C@H]4C[C@@H](O)C4)nc3c2)c2cnn(C)c2)cc1F] | 477.1 | 0.0042 | δ 9.34 (d, J = 8.6 Hz, 1H), 9.14 (s, 1H), 7.99 (s, 1H), 7.81 (t, J = 14.2 Hz, 2H), 7.61 (dd, J = 8.3, 1.3 Hz, 1H), 7.54 (s, 1H), 7.38-7.24 (m, 2H), 7.17 (dt, J = 29.9, 8.6 Hz, 2H), 6.26 (d, J = 8.5 Hz, 1H), 5.06 (d, J = 5.7 Hz, 1H), 3.90 (ddd, J = 22.1, 16.0, 7.9 Hz, 2H), 3.81 (d, J = 12.5 Hz, 6H), 2.71-2.56 (m, 2H), 1.87 (ddd, J = 17.2, 8.6, 2.7 Hz, 2H). |
| II-9 | 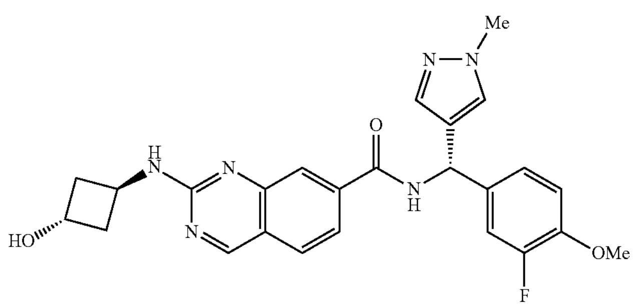 [SMILES: COc1ccc([C@H](NC(=O)c2ccc3cnc(N[C@H]4C[C@H](O)C4)nc3c2)c2cnn(C)c2)cc1F] | 477.2 | 0.0038 | δ 9.35 (d, J = 8.6 Hz, 1H), 9.15 (s, 1H), 8.01 (s, 1H), 7.84 (d, J = 8.3 Hz, 2H), 7.62 (dd, J = 8.3, 1.3 Hz, 1H), 7.55 (s, 1H), 7.36-7.24 (m, 2H), 7.23-7.11 (m, 2H), 6.26 (d, J = 8.6 Hz, 1H), 5.00 (d, J = 5.2 Hz, 1H), 4.47 (s, 1H), 4.34 (dd, J = 11.3, 6.0 Hz, 1H), 3.81 (d, J = 12.0 Hz, 6H), 2.32-2.12 (m, 4H). |
| II-10 | 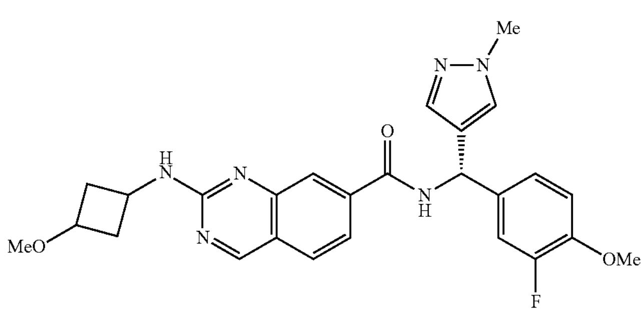 [SMILES: COc1ccc([C@H](NC(=O)c2ccc3cnc(NC4CC(OC)C4)nc3c2)c2cnn(C)c2)cc1F] | 491.2 | 0.0138 | δ 9.35 (d, J = 8.6 Hz, 1H), 9.15 (s, 1H), 7.99 (s, 1H), 7.84 (d, J = 8.3 Hz, 2H), 7.62 (dd, J = 8.3, 1.3 Hz, 1H), 7.54 (s, 1H), 7.37-7.24 (m, 2H), 7.17 (dt, J = 30.0, 8.6 Hz, 2H), 6.26 (d, J = 8.6 Hz, 1H), 4.09 (d, J = 8.0 Hz, 1H), 3.81 (d, J = 12.6 Hz, 6H), 3.64 (p, J = 7.2 Hz, 1H), 3.15 (s, 3H), 2.67 (t, J = 7.9 Hz, 2H), 1.89 (ddd, J = 16.9, 8.8, 2.7 Hz, 2H). |

TABLE II-continued

| Cpd. No. | Structure | MS | IC50¹ (μM) | ¹H NMR (400 MHz, DMSO-d₆) |
|---|---|---|---|---|
| II-11 | 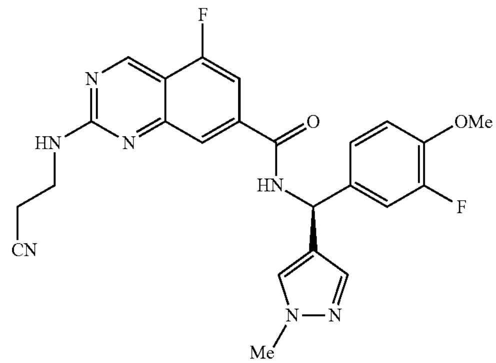 [SMILES: COc1ccc([C@H](NC(=O)c2cc(F)c3cnc(NCCC#N)nc3c2)c2cnn(C)c2)cc1F] | 478.2 | 0.0139 | δ 9.42 (d, J = 8.5 Hz, 1H), 9.35 (s, 1H), 8.15 (s, 1H), 7.95 (s, 1H), 7.54 (s, 1H), 7.42 (d, J = 10.4 Hz, 1H), 7.33 (s, 1H), 7.28 (dd, J = 12.6, 1.9 Hz, 1H), 7.20 (d, J = 8.6 Hz, 1H), 7.14 (t, J = 8.6 Hz, 1H), 6.25 (d, J = 8.2 Hz, 1H), 3.82 (s, 3H), 3.79 (s, 3H), 3.64 (brs, 2H), 2.88 (m, 2H). |
| II-12 | 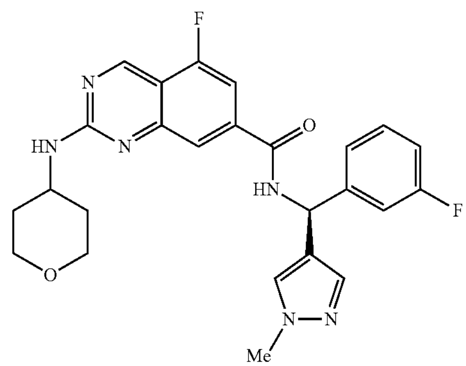 [SMILES: Cn1cc([C@@H](NC(=O)c2cc(F)c3cnc(NC4CCOCC4)nc3c2)c2cccc(F)c2)cn1] | 479.2 | 0.0012 | δ 9.46 (d, J = 8.4 Hz, 1H), 9.30 (s, 1H), 7.92 (s, 1H), 7.84 (s, 1H), 7.56 (s, 1H), 7.44-7.33 (m, 3H), 7.30-7.23 (m, 2H), 7.10 (td, J = 8.8, 2.4 Hz, 1H), 6.32 (d, J = 8.3 Hz, 1H), 4.10 (br s, 1H), 3.90 (d, J = 11.1 Hz, 2H), 3.79 (s, 3H), 3.42 (t, J = 11.1 Hz, 2H), 1.89 (d, J = 11.5 Hz, 2H), 1.59 (qd, J = 11.4, 4 Hz, 2H). |
| II-13 | 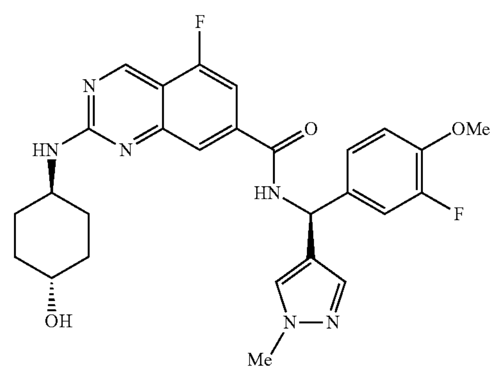 [SMILES: COc1ccc([C@H](NC(=O)c2cc(F)c3cnc(N[C@H]4CC[C@H](O)CC4)nc3c2)c2cnn(C)c2)cc1F] | 523.2 | 0.0012 | δ 9.40 (d, J = 8.0 Hz, 1H), 9.25 (s, 1H), 7.91 (s, 1H), 7.68 (br d, J = 6.8 Hz, 1H), 7.54 (s, 1H), 7.33 (d, J = 9.6 Hz, 1H), 7.32 (s, 1H), 7.27 (dd, J = 12.6, 1.9 Hz, 1H), 7.20 (dd, J = 8.8, 1.6 Hz, 1H), 7.14 (t, J = 8.6 Hz, 1H), 6.25 (d, J = 8.4 Hz, 1H), 4.54 (d, J = 4.3 Hz, 1H), 3.88-3.76 (m, 1H), 3.82 (s, 3H), 3.79 (s, 3H), 3.48-3.37 (m, 1H), 1.98-1.82 (m, 4H), 1.43-1.20 (m, 4H). |
| II-14 | 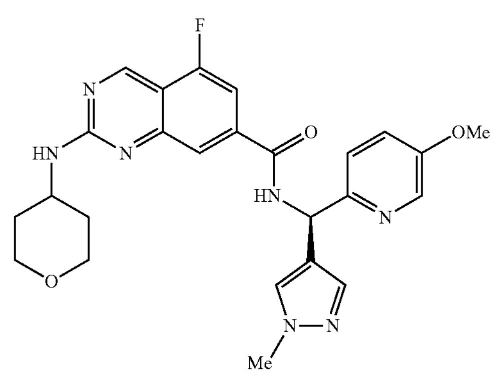 [SMILES: COc1ccc([C@H](NC(=O)c2cc(F)c3cnc(NC4CCOCC4)nc3c2)c2cnn(C)c2)nc1] | 492.2 | 0.153 | δ 9.39 (d, J = 8.2 Hz, 1H), 9.29 (s, 1H), 8.24 (d, J = 2.8 Hz, 1H), 7.92 (s, 1H), 7.83 (s, 1H), 7.55 (s, 1H), 7.45 (d, J = 8.6 Hz, 1H), 7.41-7.34 (m, 2H), 7.34 (s, 1H), 6.29 (d, J = 8.2 Hz, 1H), 4.08 (m, 1H), 3.90 (m, 2H), 3.82 (s, 3H), 3.78 (s, 3H), 3.42 (t, J = 10.9 Hz, 2H), 1.89 (d, J = 11.7 Hz, 2H), 1.59 (qd, J = 12.0, 4.4 Hz, 2H). |

TABLE II-continued

| Cpd. No. | Structure | MS | IC50[1] (μM) | $^1$H NMR (400 MHz, DMSO-d$_6$) |
|---|---|---|---|---|
| II-15 | 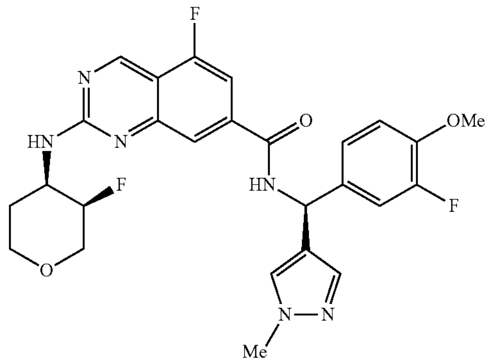 [SMILES: COc1ccc([C@H](NC(=O)c2cc(F)c3cnc(N[C@@H]4CCOC[C@@H]4F)nc3c2)c2cnn(C)c2)cc1F] | 527.2 | 0.0043 | |
| II-16 | 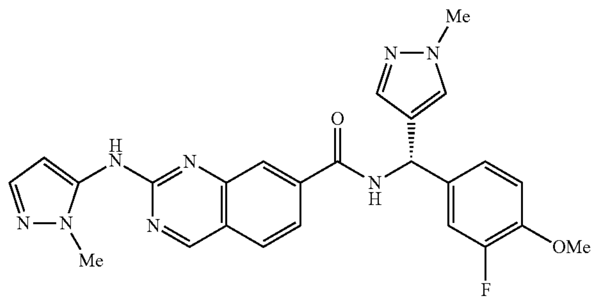 [SMILES: COc1ccc([C@H](NC(=O)c2ccc3cnc(Nc4ccnn4C)nc3c2)c2cnn(C)c2)cc1F] | 487.2 | 0.0021 | δ 9.71 (s, 1H), 9.38 (d, J = 7.5 Hz, 2H), 8.15 (s, 1H), 8.00 (d, J = 8.4 Hz, 1H), 7.80 (d, J = 8.3 Hz, 1H), 7.53 (s, 1H), 7.39 (d, J = 1.7 Hz, 1H), 7.32 (s, 1H), 7.27 (d, J = 12.7 Hz, 1H), 7.16 (dt, J = 17.1, 8.5 Hz, 2H), 6.40 (s, 1H), 6.27 (d, J = 8.5 Hz, 1H), 3.82 (s, 3H), 3.79 (d, J = 3.7 Hz, 3H), 3.73 (d, J = 11.7 Hz, 3H). |
| II-17 | 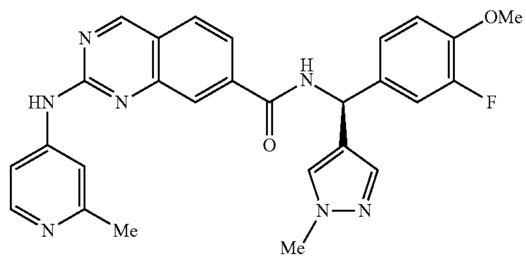 [SMILES: COc1ccc([C@H](NC(=O)c2ccc3cnc(Nc4ccnc(C)c4)nc3c2)c2cnn(C)c2)cc1F] | 498.1 | 0.0048 | |
| II-18 | 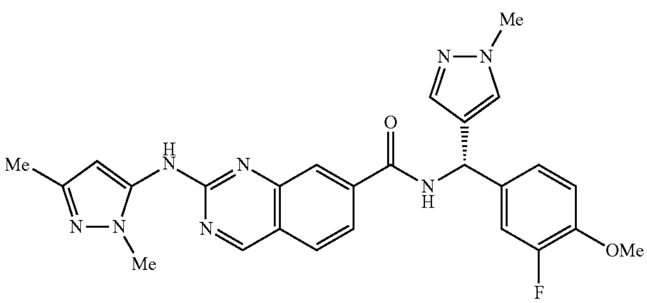 [SMILES: COc1ccc([C@H](NC(=O)c2ccc3cnc(Nc4cc(C)nn4C)nc3c2)c2cnn(C)c2)cc1F] | 501.2 | 0.0021 | δ 9.64 (s, 1H), 9.38 (d, J = 8.8 Hz, 2H), 8.15 (s, 1H), 7.99 (d, J = 8.4 Hz, 1H), 7.79 (dd, J = 8.3, 1.2 Hz, 1H), 7.54 (s, 1H), 7.32 (s, 1H), 7.29-7.24 (m, 1H), 7.20 (d, J = 10.2 Hz, 1H), 7.14 (t, J = 8.6 Hz, 1H), 6.27 (d, J = 8.4 Hz, 1H), 6.18 (s, 1H), 3.80 (d, J = 13.1 Hz, 6H), 3.63 (s, 3H), 2.14 (s, 3H). |
| II-19 | 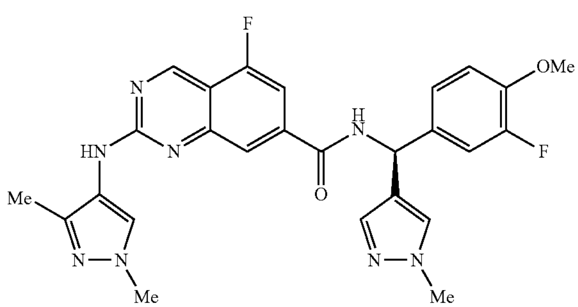 [SMILES: COc1ccc([C@H](NC(=O)c2cc(F)c3cnc(Nc4cn(C)nc4C)nc3c2)c2cnn(C)c2)cc1F] | 519.2 | 0.0068 | |

TABLE II-continued

| Cpd. No. | Structure | MS | IC50[1] (μM) | 1H NMR (400 MHz, DMSO-d6) |
|---|---|---|---|---|
| II-20 | 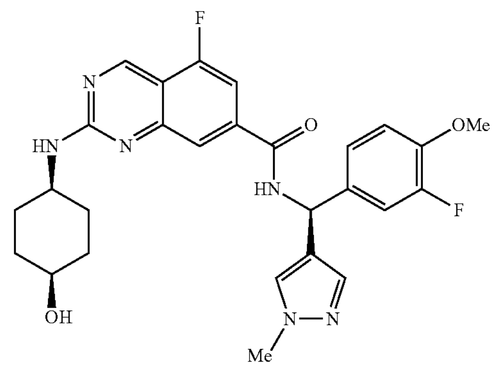 [SMILES: COc1ccc([C@H](NC(=O)c2cc(F)c3cnc(N[C@H]4CC[C@@H](O)CC4)nc3c2)c2cnn(C)c2)cc1F] | 523 | 0.0097 | δ 9.39 (d, J = 8.5 Hz, 1H), 9.26 (s, 1H), 7.88 (s, 1H), 7.70 (s, 1H), 7.54 (s, 1H), 7.32 (d, J = 10.4 Hz, 1H), 7.32 (s, 1H), 7.27 (d, J = 12.7 Hz, 1H), 7.19 (d, J = 9.8 Hz, 1H), 7.13 (t, J = 8.6 Hz, 1H), 6.55 (s, 1H), 6.24 (d, J = 8.4 Hz, 1H), 4.35 (d, J = 2.4 Hz, 1H), 3.87 (s, 1H), 3.82 (s, 3H), 3.79 (s, 3H), 3.76 (s, 1H), 1.86-1.58 (m, 6H), 1.51 (t, J = 11.9 Hz, 2H). |
| II-21 | 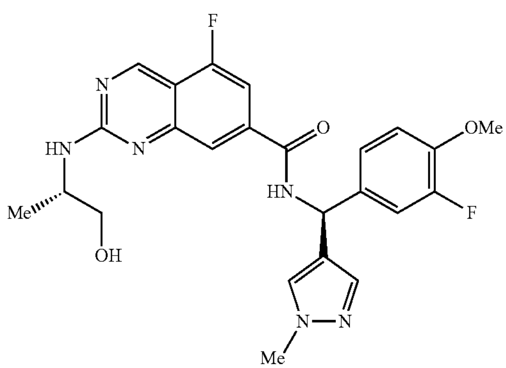 [SMILES: COc1ccc([C@H](NC(=O)c2cc(F)c3cnc(N[C@@H](C)CO)nc3c2)c2cnn(C)c2)cc1F] | 483.1 | 0.0023 | δ 9.38 (d, J = 8.4 Hz, 1H), 9.28 (s, 1H), 7.88 (s, 1H), 7.54 (s, 1H), 7.49 (br s, 1H), 7.34 (d, J = 10 Hz, 2H), 7.32 (s, 1H), 7.27 (d, J = 12.5 Hz, 1H), 7.19 (d, J = 9.9 Hz, 1H), 7.13 (t, J = 8.6 Hz, 1H), 6.25 (d, J = 8.5 Hz, 1H), 4.71 (t, J = 5.6 Hz, 1H), 4.12 (septet, J = 7 Hz, 1H), 3.82 (s, 3H), 3.79 (s, 3H), 3.53 (dt, J = 10.7, 5.4 Hz, 1H), 3.43-3.35 (dt, J = 10.8, 5.2 Hz, 1H), 1.18 (d, J = 6.6 Hz, 3H). |
| II-22 | 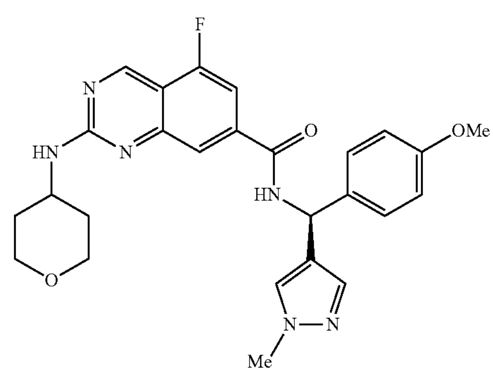 [SMILES: COc1ccc([C@H](NC(=O)c2cc(F)c3cnc(NC4CCOCC4)nc3c2)c2cnn(C)c2)cc1] | 491.1 | 0.0070 | δ 9.37 (d, J = 8.5 Hz, 1H), 9.29 (s, 1H), 7.90 (br s, 1H), 7.79 (br s, 1H), 7.51 (s, 1H), 7.38-7.30 (m, 4H), 6.91 (d, J = 8.7 Hz, 2H), 6.25 (d, J = 8.4 Hz, 1H), 4.07 (br s, 1H), 3.90 (d, J = 11.5 Hz, 1H), 3.79 (s, 3H), 3.74 (s, 3H), 3.42 (t, J = 10.8 Hz, 2H), 1.89 (d, J = 11.6 Hz, 2H), 1.59 (qd, J = 11.7, 4.3 Hz, 2H). |
| II-23 | 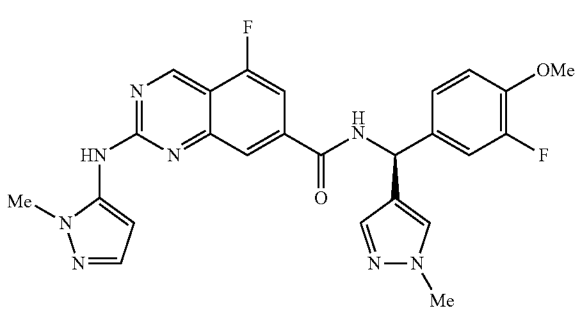 [SMILES: COc1ccc([C@H](NC(=O)c2cc(F)c3cnc(Nc4ccnn4C)nc3c2)c2cnn(C)c2)cc1F] | 505.1 | 0.0108 | |

TABLE II-continued

| Cpd. No. | Structure | MS | IC50¹ (μM) | ¹H NMR (400 MHz, DMSO-d₆) |
|---|---|---|---|---|
| II-24 | 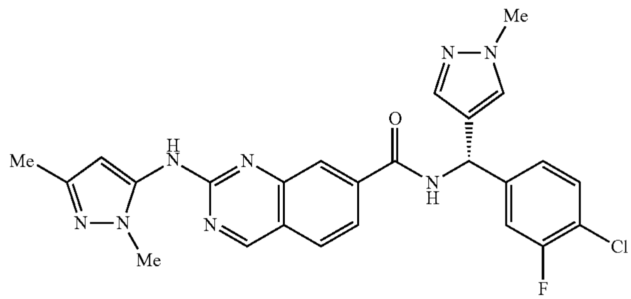 [SMILES: Cc1cc(Nc2ncc3ccc(C(=O)N[C@@H](c4ccc(Cl)c(F)c4)c4cnn(C)c4)cc3n2)n(C)n1] | 505.1 | 0.0146 | δ 9.62 (s, 1H), 9.43 (d, J = 8.3 Hz, 1H), 9.37 (s, 1H), 8.16 (s, 1H), 8.00 (d, J = 8.4 Hz, 1H), 7.79 (dd, J = 8.4, 1.6 Hz, 1H), 7.57 (t, J = 8.0 Hz, 2H), 7.47 (dd, J = 10.6, 2.0 Hz, 1H), 7.36 (s, 1H), 7.31 (dd, J = 8.3, 1.9 Hz, 1H), 6.33 (d, J = 8.3 Hz, 1H), 6.18 (s, 1H), 3.79 (s, 3H), 3.63 (s, 3H), 2.14 (s, 3H). |
| II-25 | 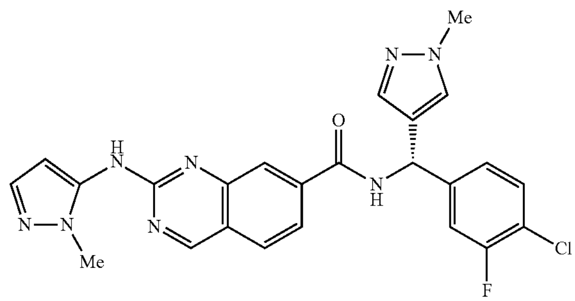 [SMILES: Cn1cc([C@@H](NC(=O)c2ccc3cnc(Nc4ccnn4C)nc3c2)c2ccc(Cl)c(F)c2)cn1] | 491.0 | 0.0031 | δ 9.69 (s, 1H), 9.43 (d, J = 8.3 Hz, 1H), 9.39 (s, 1H), 8.16 (s, 1H), 8.01 (d, J = 8.4 Hz, 1H), 7.80 (dd, J = 8.4, 1.5 Hz, 1H), 7.57 (t, J = 8.1 Hz, 2H), 7.47 (dd, J = 10.5, 2.0 Hz, 1H), 7.38 (d, J = 1.9 Hz, 1H), 7.36 (s, 1H), 7.31 (dd, J = 8.4, 1.9 Hz, 1H), 6.39 (d, J = 1.9 Hz, 1H), 6.32 (d, J = 8.3 Hz, 1H), 3.79 (s, 3H), 3.72 (s, 3H). |
| II-26 | 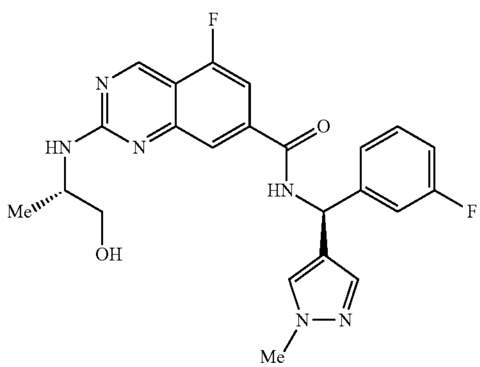 [SMILES: C[C@@H](CO)Nc1ncc2c(F)cc(C(=O)N[C@@H](c3cccc(F)c3)c3cnn(C)c3)cc2n1] | 453.0 | 0.0056 | δ 9.43 (d, J = 8.4 Hz, 1H), 9.28 (s, 1H), 7.89 (s, 1H), 7.57 (s, 1H), 7.46 (s, 1H), 7.40 (td, J = 8.2, 6.2 Hz, 1H), 7.35 (dd, J = 10.6, 1.0 Hz, 1H), 7.35 (s, 1H), 7.28 (d, J = 1.6 Hz, 1H), 7.26 (d, J = 10.8 Hz, 1H), 7.09 (td, J = 8.6, 2.4 Hz, 1H), 6.32 (d, J = 8.4 Hz, 1H), 4.69 (t, J = 5.6 Hz, 1H), 4.19-4.07 (m, 1H), 3.79 (s, 3H), 3.53 (dt, J = 10.8, 5.5 Hz, 1H), 3.44-3.36 (m, 1H), 1.19 (d, J = 6.6 Hz, 3H). |
| II-27 | 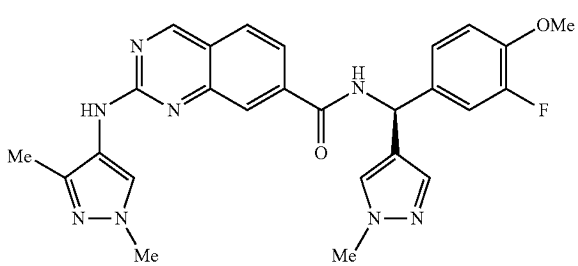 [SMILES: COc1ccc([C@H](NC(=O)c2ccc3cnc(Nc4cn(C)nc4C)nc3c2)c2cnn(C)c2)cc1F] | 501.2 | 0.96 | |
| II-28 | 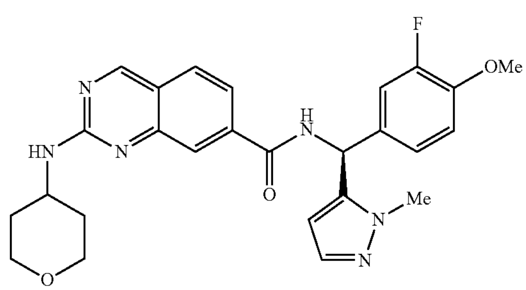 [SMILES: COc1ccc([C@H](NC(=O)c2ccc3cnc(NC4CCOCC4)nc3c2)c2ccnn2C)cc1F] | 491.2 | 0.003 | |

TABLE II-continued

| Cpd. No. | Structure | MS | IC50[1] (μM) | $^1$H NMR (400 MHz, DMSO-d6) |
|---|---|---|---|---|
| II-29 | 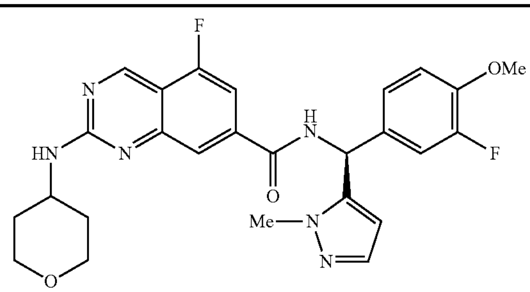 | 509.2 | 0.0022 | |
| II-30 | 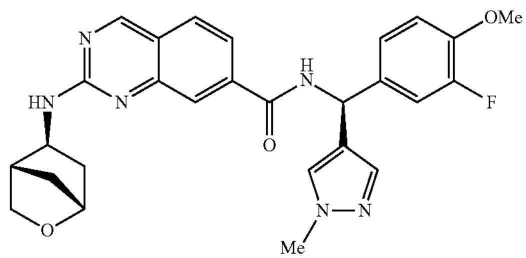 [SMILES: COc1ccc([C@H](NC(=O)c2ccc3cnc(N[C@H]4C[C@H]5C[C@@H]4CO5)nc3c2)c2cnn(C)c2)cc1F] | 503.3 | 1 | |
| II-31 | 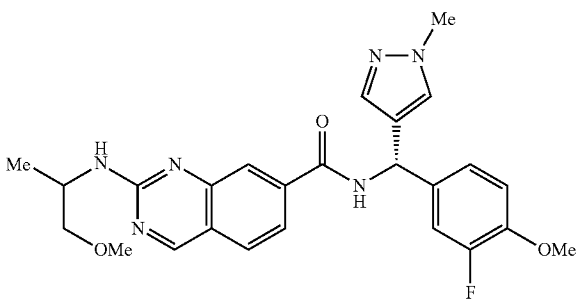 [SMILES: COCC(C)Nc1ncc2ccc(C(=O)N[C@@H](c3ccc(OC)c(F)c3)c3cnn(C)c3)cc2n1] | 479.1 | 0.015 | δ 9.34 (d, J = 8.6 Hz, 1H), 9.16 (s, 1H), 8.00 (s, 1H), 7.84 (d, J = 8.3 Hz, 1H), 7.62 (dd, J = 8.3, 1.5 Hz, 1H), 7.54 (s, 1H), 7.39-7.24 (m, 3H), 7.16 (dt, J = 17.2, 8.6 Hz, 2H), 6.26 (d, J = 8.5 Hz, 1H), 4.37-4.25 (m, 1H), 3.82 (s, 3H), 3.79 (s, 3H), 3.47 (dd, J = 9.4, 6.0 Hz, 1H), 3.41-3.33 (m, 1H), 3.28 (s, 3H), 1.18 (d, J = 6.7 Hz, 3H). |
| II-32 | 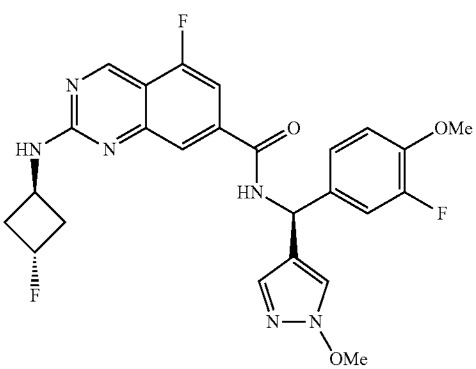 [SMILES: COc1ccc([C@H](NC(=O)c2cc(F)c3cnc(N[C@H]4C[C@H](F)C4)nc3c2)c2cnn(OC)c2)cc1F] | 497.2 | 0.0045 | δ 9.40 (d, J = 8.4 Hz, 1H), 9.31 (s, 1H), 8.23 (s, 1H), 7.93 (s, 1H), 7.54 (s, 1H), 7.38 (d, J = 10.4 Hz, 1H), 7.32 (s, 1H), 7.27 (d, J = 12.7 Hz, 1H), 7.20 (d, J = 8.7 Hz, 1H), 7.14 (t, J = 8.6 Hz, 1H), 6.25 (d, J = 8.4 Hz, 1H), 5.29 (d, J = 56.8 Hz, 1H), 4.67-4.54 (m, 1H), 3.82 (s, 3H), 3.79 (s, 3H), 2.64-2.50 (m, 2H), 2.50-2.38 (m, 2H). |
| II-33 | 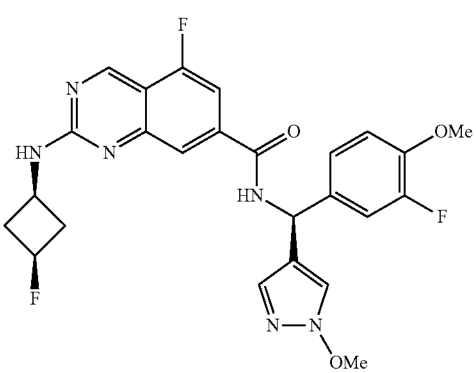 [SMILES: COc1ccc([C@H](NC(=O)c2cc(F)c3cnc(N[C@H]4C[C@@H](F)C4)nc3c2)c2cnn(OC)c2)cc1F] | 497.1 | 0.0038 | δ 9.39 (d, J = 8.5 Hz, 1H), 9.31 (s, 1H), 8.19 (s, 1H), 7.88 (s, 1H), 7.54 (s, 1H), 7.38 (d, J = 10.4 Hz, 1H), 7.33 (s, 1H), 7.27 (d, J = 12.8 Hz, 1H), 7.19 (d, J = 8.6 Hz, 1H), 7.14 (t, J = 8.6 Hz, 1H), 6.24 (d, J = 8.4 Hz, 1H), 4.91 (d, J = 56.6 Hz, 1H), 4.12-3.98 (m, 1H), 3.82 (s, 3H), 3.79 (s, 3H), 2.87-2.75 (s, 2H), 2.34-2.18 (m, 2H). |

TABLE II-continued

| Cpd. No. | Structure | MS | IC50¹ (μM) | ¹H NMR (400 MHz, DMSO-d₆) |
|---|---|---|---|---|
| II-34 | 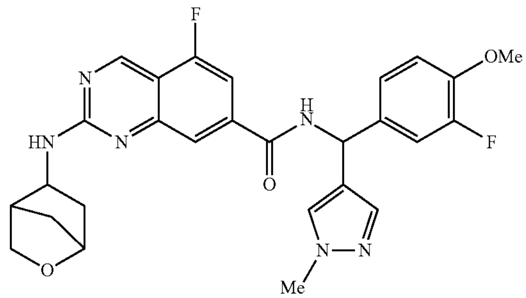 [SMILES: COc1ccc(C(NC(=O)c2cc(F)c3cnc(NC4CC5CC4CO5)nc3c2)c2cnn(C)c2)cc1F] | 521.2 | 1 | |
| II-35 | 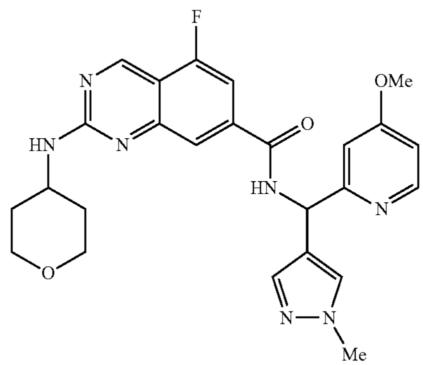 [SMILES: COc1ccnc(C(NC(=O)c2cc(F)c3cnc(NC4CCOCC4)nc3c2)c2cnn(C)c2)c1] | 492.1 | 0.061 | δ 9.39 (d, J = 8.3 Hz, 1H), 9.30 (s, 1H), 8.35 (d, J = 5.7 Hz, 1H), 7.93 (s, 1H), 7.84 (s, 1H), 7.58 (s, 1H), 7.39-7.33 (m, 2H), 7.11 (d, J = 2.3 Hz, 1H), 6.89 (dd, J = 5.7, 2.4 Hz, 1H), 6.27 (d, J = 8.3 Hz, 2H), 4.10 (s, 1H), 3.90 (d, J = 11.3 Hz, 2H), 3.82 (s, 3H), 3.78 (s, 3H), 3.42 (t, J = 11.3 Hz, 2H), 1.89 (d, J = 12.1 Hz, 2H), 1.59 (m, 2H). |
| II-36 | 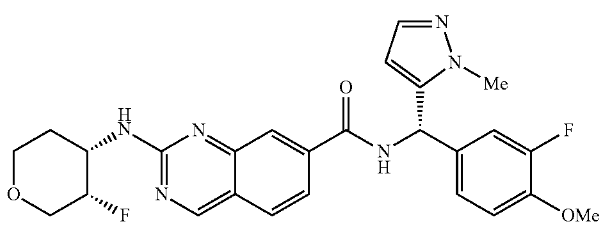 [SMILES: COc1ccc([C@H](NC(=O)c2ccc3cnc(N[C@H]4CCOC[C@H]4F)nc3c2)c2ccnn2C)cc1F] | 509.2 | 0.0038 | (500 MHz, CDCl₃): δ 9.15 (s, 1H), 7.99 (s, 1H), 7.89 (d, J = 8.0 Hz, 1H), 7.66 (d, J = 8.5 Hz, 1H), 7.44 (s, 1H), 7.19-7.14 (m, 3H), 6.55 (s, 1H), 6.13 (s, 1H), 4.80 (s, 1H), 4.45-4.37 (m, 1H), 4.18-4.04 (m, 2H), 3.90 (s, 3H), 3.82 (s, 3H), 3.78-3.60 (m, 2H), 2.14-2.04 (m, 1H), 1.89-1.87 (m, 1H) |
| II-37 | 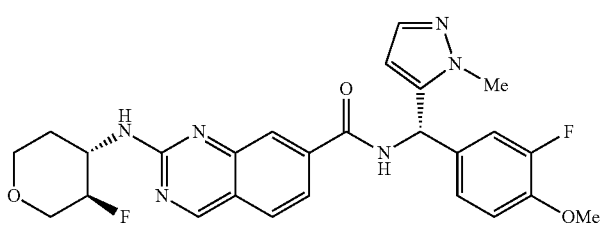 [SMILES: COc1ccc([C@H](NC(=O)c2ccc3cnc(N[C@H]4CCOC[C@@H]4F)nc3c2)c2ccnn2C)cc1F] | 509.2 | 0.0036 | (500 MHz, DMSO-d₆): δ 9.64 (d, J = 8.0 Hz, 1H), 9.22 (s, 1H), 8.07 (s, 1H), 7.90-7.84 (m, 2H), 7.67 (d, J = 8.0 Hz, 1H), 7.35-7.33 (m, 2H), 7.26-7.17 (m, 2H), 6.49 (d, J = 8.0 Hz, 1H), 5.95 (s, 1H), 4.65 (s, 0.5H), 4.55 (s, 0.5H), 4.38 (s, 1H), 4.06-4.02 (m, 1H), 3.86-3.83 (m, 1H), 3.80 (s, 3H), 3.74 (s, 3H), 3.51-3.42 (m, 2H), 2.08-2.01 (m, 1H), 1.68-1.61 (m, 1H) |
| II-38 | 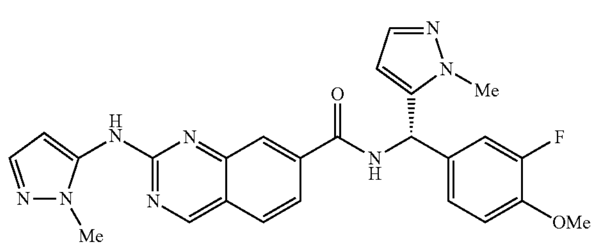 [SMILES: COc1ccc([C@H](NC(=O)c2ccc3cnc(Nc4ccnn4C)nc3c2)c2ccnn2C)cc1F] | 487.3 | 0.0029 | (500 MHz, DMSO-d₆): δ 9.70 (s, 1H), 9.63 (d, J = 8.5 Hz, 1H), 9.39 (s, 1H), 8.16 (s, 1H), 8.01 (d, J = 8.0 Hz, 1H), 7.80 (d, J = 8.5 Hz, 1H), 7.38 (d, J = 1.5, 1H) 7.34-7.30 (m, 2H), 7.26-7.16 (m, 2H), 6.49 (d, J = 8.5 Hz, 1H), 6.39 (d, J = 1.5 Hz, 1H), 5.93 (d, J = 2.0 Hz, 1H), 3.83 (s, 3H), 3.73 (s, 3H), 3.71 (s, 3H); |

TABLE II-continued

| Cpd. No. | Structure | MS | IC50[1] (μM) | $^1$H NMR (400 MHz, DMSO-d6) |
|---|---|---|---|---|
| II-39 | 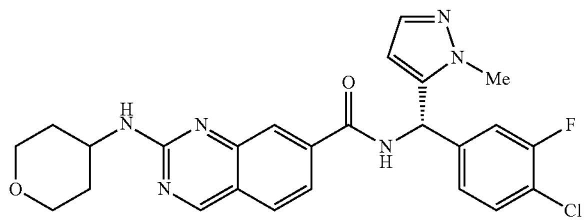 [SMILES: Cn1nccc1[C@@H](NC(=O)c1ccc2cnc(NC3CCOCC3)nc2c1)c1ccc(Cl)c(F)c1] | 495.3 | 0.151 | (500 MHz, DMSO-d6): δ 9.68 (d, J = 8.0 Hz, 1H), 9.17 (s, 1H), 8.06 (s, 1H), 7.86 (d, J = 8.0 Hz, 1H), 7.65-7.53 (m, 4H), 7.38-7.33 (m, 2H), 6.57 (d, J = 8.5 Hz, 1H), 5.89 (d, J = 1.5 Hz, 1H), 4.09-4.05 (m, 1H), 3.89 (d, J = 11.0 Hz, 2H), 3.77 (s, 3H), 3.44-3.38 (m, 2H), 1.89-1.86 (m, 2H), 1.61-1.53 (m, 2H) |
| II-40 | 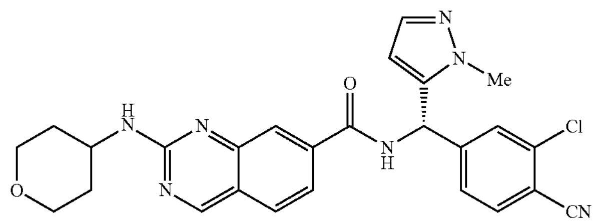 [SMILES: Cn1nccc1[C@@H](NC(=O)c1ccc2cnc(NC3CCOCC3)nc2c1)c1ccc(C#N)c(Cl)c1] | 502.1 | 0.026 | (500 MHz, DMSO-d6): δ 9.73 (d, J = 8.0 Hz, 1H), 9.18 (s, 1H), 8.08-8.02 (m, 2H), 7.88-7.86 (m, 2H), 7.69-7.60 (m, 3H), 7.34 (d, J = 1.5 Hz, 1H), 6.65 (d, J = 8.0 Hz, 1H), 5.85 (d, J = 2.0 Hz, 1H), 4.07 (s, 1H), 3.89 (d, J = 11.5 Hz, 2H), 3.80 (s, 3H), 3.44-3.41 (m, 2H), 1.91-1.87 (m, 2H), 1.60-1.53 (m, 2H) |
| II-41 | 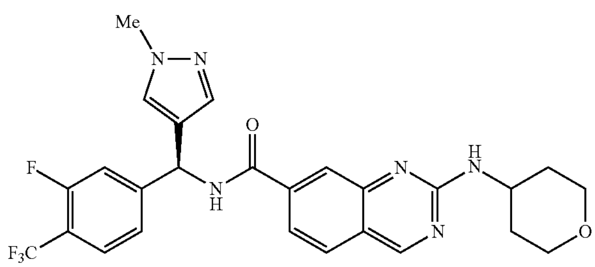 [SMILES: Cn1cc([C@@H](NC(=O)c2ccc3cnc(NC4CCOCC4)nc3c2)c2ccc(C(F)(F)F)c(F)c2)cn1] | 529.3 | 0.0052 | |
| II-42 | 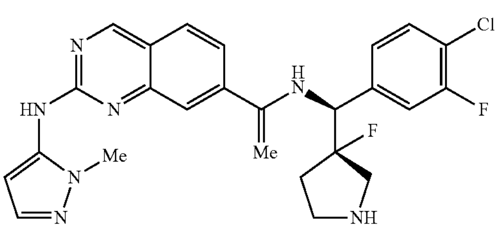 | 498.1 | 0.0346 | |
| II-43 | 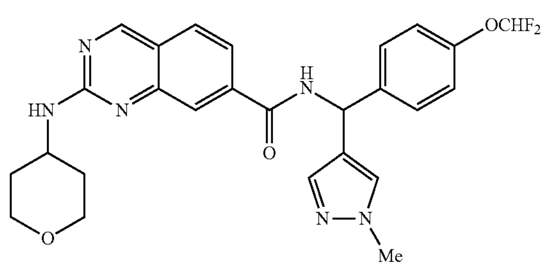 [SMILES: Cn1cc(C(NC(=O)c2ccc3cnc(NC4CCOCC4)nc3c2)c2ccc(OC(F)F)cc2)cn1] | 509.3 | 0.0121 | |
| II-44 | 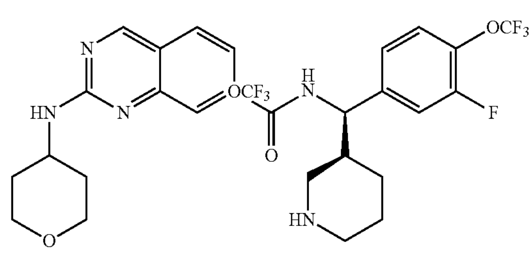 | 548.2 | 0.216 | |

TABLE II-continued

| Cpd. No. | Structure | MS | IC50[1] (μM) | $^1$H NMR (400 MHz, DMSO-d6) |
|---|---|---|---|---|
| II-45 | 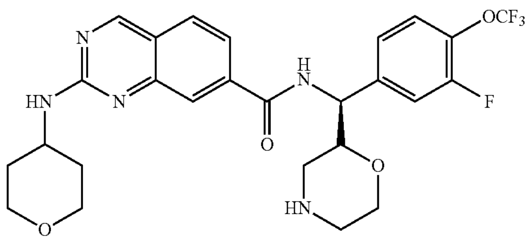 [SMILES: O=C(N[C@@H](c1ccc(OC(F)(F)F)c(F)c1)C1CNCCO1)c1ccc2cnc(NC3CCOCC3)nc2c1] | 550.3 | 0.0069 | |
| II-46 | 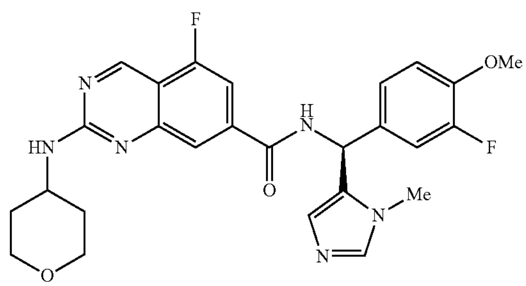 [SMILES: COc1ccc([C@H](NC(=O)c2cc(F)c3cnc(NC4CCOCC4)nc3c2)c2cncn2C)cc1F] | 509.2 | 0.0011 | |
| II-47 | 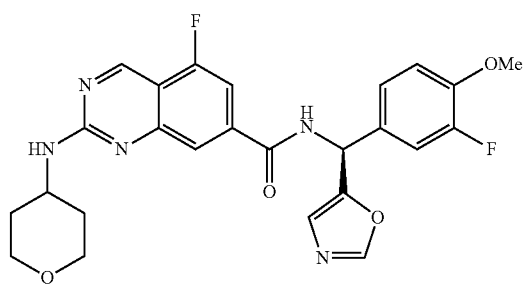 [SMILES: COc1ccc([C@H](NC(=O)c2cc(F)c3cnc(NC4CCOCC4)nc3c2)c2cnco2)cc1F] | 496.2 | 0.0013 | |
| II-48 | 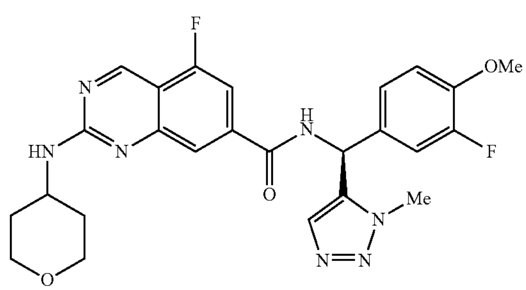 [SMILES: COc1ccc([C@H](NC(=O)c2cc(F)c3cnc(NC4CCOCC4)nc3c2)c2cnnn2C)cc1F] | 510.2 | 0.0014 | |
| II-49 | 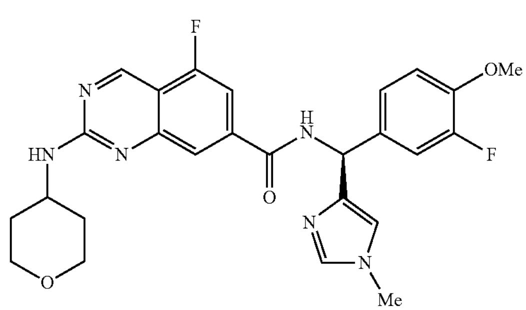 [SMILES: COc1ccc([C@H](NC(=O)c2cc(F)c3cnc(NC4CCOCC4)nc3c2)c2cn(C)cn2)cc1F] | 509.3 | 0.0855 | |

TABLE II-continued

| Cpd. No. | Structure | MS | IC50[1] (µM) | $^1$H NMR (400 MHz, DMSO-d$_6$) |
|---|---|---|---|---|
| II-50 | 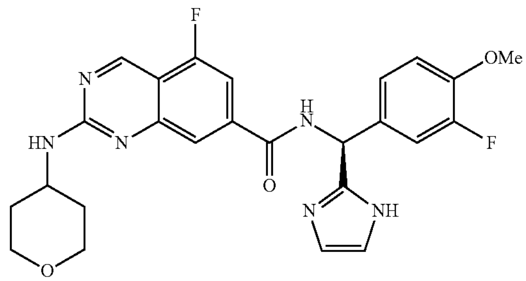 [SMILES: COc1ccc([C@H](NC(=O)c2cc(F)c3cnc(NC4CCOCC4)nc3c2)c2ncc[nH]2)cc1F] | 495.2 | 0.0591 | |
| II-51 | 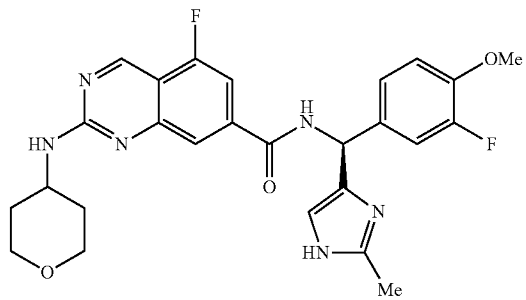 [SMILES: COc1ccc([C@H](NC(=O)c2cc(F)c3cnc(NC4CCOCC4)nc3c2)c2c[nH]c(C)n2)cc1F] | 509.2 | 0.164 | |
| II-52 | 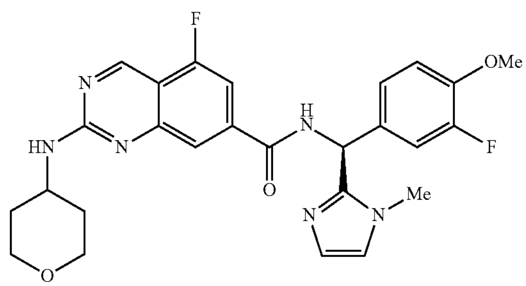 [SMILES: COc1ccc([C@H](NC(=O)c2cc(F)c3cnc(NC4CCOCC4)nc3c2)c2nccn2C)cc1F] | 509.2 | 0.0019 | |
| II-53 | 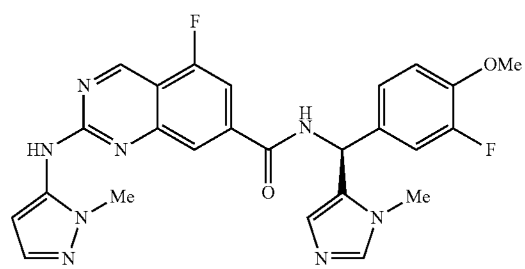 [SMILES: COc1ccc([C@H](NC(=O)c2cc(F)c3cnc(Nc4ccnn4C)nc3c2)c2cncn2C)cc1F] | 505.2 | 0.0015 | |
| II-54 | 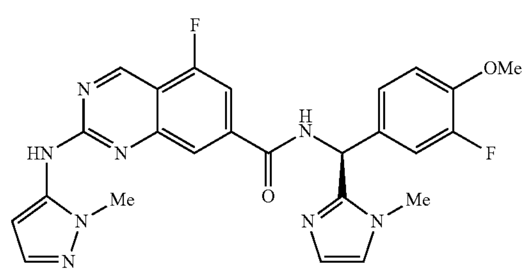 [SMILES: COc1ccc([C@H](NC(=O)c2cc(F)c3cnc(Nc4ccnn4C)nc3c2)c2nccn2C)cc1F] | 505.2 | 0.0085 | |

[1]ERK-2 Enzymatic Assay (Example 9)

Compounds of the present invention can be made by a variety of methods depicted in the illustrative synthetic reaction schemes shown and described below. The starting materials and reagents used in preparing these compounds generally are either available from commercial suppliers, such as Sigma Aldrich Chemical Co., or are prepared by methods known to those skilled in the art. Generally applicable synthetic procedures have been described in treatises are set forth in references such as *Fieser and Fieser's Reagents for Organic Synthesis*; Wiley & Sons: New York, Volumes 1-21;

R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques. Typically such separations involve multiphase extraction, crystallization from a solvent or solvent mixture, distillation, sublimation, or chromatography. Chromatography can involve any number of methods including, for example: chiral, reverse-phase and normal phases; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J Chromatogr.*, 1975 113(3):283-302). Racemic mixtures of chiral compounds of the invention can be separated and isolated by any suitable method, including: (1) formation of ionic, diastereomeric salts with chiral compounds and separation by fractional crystallization or other methods, (2) converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers, and (3) separation of the substantially pure or enriched stereoisomers directly under chiral conditions (see, e.g., *Drug Stereochemistry, Analytical Methods and Pharmacology*, Irving W. Wainer, Ed., Marcel Dekker, Inc., New York 1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (E. Eliel and S. Wilen, *Stereochemistry of Organic Compounds*, John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate, in the presence of base, or Mosher ester, α-methoxy-α-(trifluoromethyl)phenyl acetate (Jacob III. *J. Org. Chem.*, 1982 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" 1989 W. J. Lough, Ed., Chapman and Hall, New York; Okamoto, *J. Chromatogr.*, 1990 513:375-378). Enriched or purified enantiomers can be distinguished by methods used to distinguish other chiral molecules with asymmetric carbon atoms, such as optical rotation and circular dichroism.

Racemic mixtures can be separated by supercritical fluid chromatography using a Mettler Toledo MG II chromatograph using a 5 µm AS-H SFC 21.2×250 mm column or AD-H SFC column using MeOH or IPA containing 0.1% TFA as a cosolvent. Typical conditions include a flow rate of 50 mL/min, a column temperature of 40° C. Run time was typically 5 to 10 min.

Some compounds in the following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

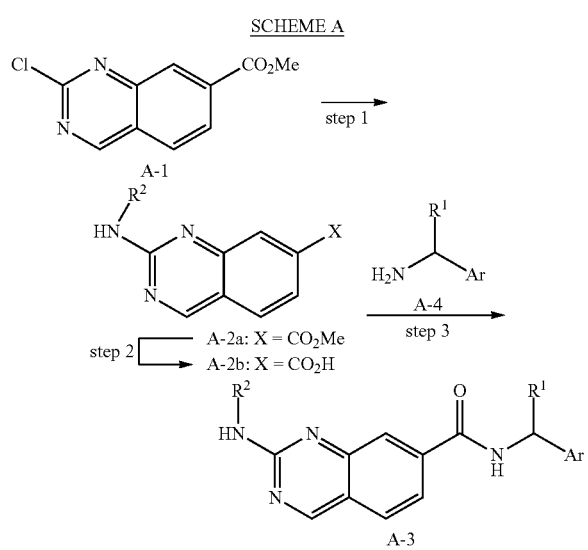

A subset of compounds disclosed herein can be prepared from methyl 2-chloro-quinazoline-7-carboxylate (A–1) (L. Huang et al. WO2007/125405) as shown in SCHEME A. Introduction of the desired amine at the 2-position to afford A-2a is accomplished by direct displacement utilizing an $S_NAr$ reaction with heating. Subsequent hydrolysis of the methyl ester with hydroxide affords the carboxylic acid A-2b, which can be further elaborated using standard peptide coupling protocols to introduce the amide linkage.

Alternatively, introduction of primary or secondary amines by replacement of a leaving group on a (hetero)aryl ring can be accomplished by Buchwald-Hartwig palladium-catalyzed cross-coupling of an amine and A-1 (J. P. Wolfe and S. L. Buchwald *J. Org. Chem* 2000 65:1144-1157 and *Acc. Chem. Res.* 1998 31:805-818; J. P. Wolfe et al. *J. Org. Chem* 2000 65:1158; J. F. Hartwig *Angew. Chem. Int. Ed.* 1998 37:2046-2067). Typical conditions include $Pd(dppf)Cl_2$ in the presence of base, e.g., sodium tert-butoxide or $Cs_2CO_3$, and aprotic solvent. Typical leaving groups include halogens and triflates and optimum leaving groups will depend on the precise reactant.

SCHEME B

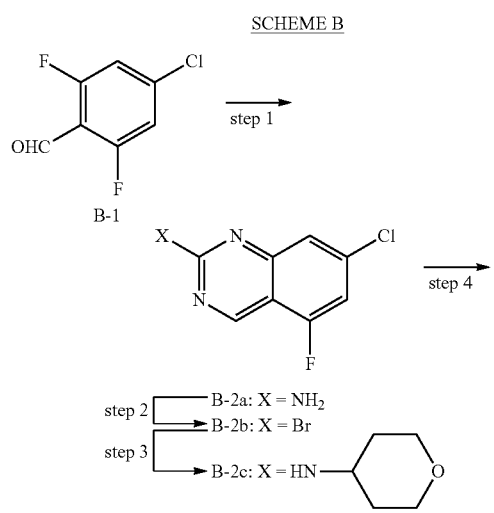

Other compounds disclosed herein are prepared from 5-fluoro-2-(tetrahydro-2H-pyran-4-ylamino)quinazoline-7-carboxylic acid (B-3b) as described in SCHEME B. 2,6-Difluoro-4-chloro-benzaldehyde was converted to the 2-aminoquinazoline B-2a by condensation with guanidine bis-carbonate. This aminoquinazoline is then converted to the 2-bromo-quinazoline B-2b with antimony tribromide and tert-butyl nitrite in $CBr_4$. Displacement of the bromide of B-2b with tetrahydro-2H-pyran-4-amine afforded B-2c. One skilled in the art will appreciate that the reaction can be carried out with the requisite amines to afford other quinazolines within the scope of the invention. The 7-carboxy substituent is introduced via a palladium-catalyzed carboxylation using potassium 2-ethoxy-2-oxoacetate as the source of the carboxyl group to afford the quinazoline ester B-3a. Subsequent hydrolysis of the ester with hydroxide affords the carboxylic acid B-3b which can be further converted to amides using standard coupling protocols. Alternatively, 4-bromo-2,6-difluorobenzaldehyde is cyclized with guanidine bis(carbonate) to afford B-5 which can then be subject to similar functional group transformations albeit in a different sequence. Carbonylation to introduce the methoxy carbonyl (step 7) precedes introduction of the cyclopropylmethylamine (steps 8 and 9). Hydrolysis of the ester affords the substituted quinazoline analogous to B-3b.

The amine A-4 may be prepared as described in SCHEME C, where aryl-heteroaryl amines (C-3) may be prepared by steps 1 through 2, and aryl-heterocyclyl amines (C-6) may be prepared by steps 3 through 7. The requisite aryl-heteroaryl amines A-4 (C-3, R=pyrazolyl, triazolyl oxadiazolyl, oxazolyl or isoxazolyl), which are optionally chiral, can be prepared using the general method depicted in steps 1 and 2 of SCHEME C. Addition of an aryl Grignard or aryl lithium reagent to the N-tert-butylsulfinyl imines (C-2) afforded amines (A-4/C-3) after hydrolysis of the intermediate sulfinamides. Chiral amines are prepared by addition of an aryl Grignard or lithium to a chiral sulfinamide. (D. A. Cogan et al., Tetrahedron 1999 55:8883-8904). The sulfinyl imines are, in turn, available from the large pool of aldehydes which can be easily prepared or purchased.

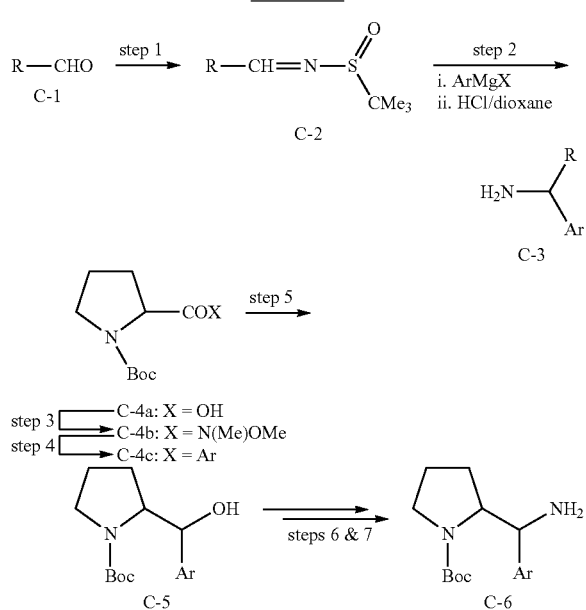

SCHEME C

The requisite aryl-heterocyclyl amines A-4 (C-6, Ar=optionally substituted phenyl) can be prepared from the corresponding heterocyclyl carboxylic acid. Conversion of the N-Boc-proline (C-4a) to the N-methyl-N-methoxyamide (C-4b) and addition of an aryl lithium affords C-4c. C-4c may be reduced with (R)-1-methyl-3,3-diphenylhexahydropyrrolo[1,2-c][1,3,2]oxazaborole and borane diethylaniline (A.M. Salunkhe and E. R. Burkhardt Tetrahedron Lett. 1997 38(9)1523-1526 and 38(9)1519-1522; and E. J. Corey et al., J. Am. Chem. Soc. 1987 109:5551). The conversion of the alcohol to the amine A-4 (C-6) is accomplished via the Gabriel synthesis under Mitsunobu conditions to introduce the phthalimide moiety which can be removed with hydrazine (steps 6 & 7).

Mitsunobu conditions (D. L. Hughes, The Mitsunobu Reaction, in Organic Reactions, Volume 42, 1992, John Wiley & Sons, New York; pp. 335-656) comprise activating alcohols with a mixture of a phosphine, such as a trialkylphosphine like tributylphosphine ((n-Bu)$_3$P), triphenylphosphine (Ph$_3$P) and the like and a diazo-compound like DEAD, DIAD or di-tert-butyl-azodicarboxylate in an inert solvent. Commonly used solvents include, but are not limited to, THF, toluene and DCM. There is no particular limitation on the nature of the solvent to be employed, provided that it has no adverse effect on the reaction or the reagents involved and that it can dissolve the reagents, at least to some extent. The reaction can take place over a wide range of temperatures ranging from ambient temperatures to the reflux temperature of the solvent employed Condensation of the quinazolines A-2b or B-3b and the amine A-4 was carried out with activated esters using known protocols. Activated carboxylic acids include acid chlorides or symmetrical or mixed acid anhydrides which react with amines in a solvent such as DMF, DCM, THF, with or without water as a co-solvent at temperatures between 0° C. and 60° C. generally in the presence of a base, such as Na$_2$CO$_3$, NaHCO$_3$, K$_2$CO$_3$, DIPEA, TEA or pyridine. Carboxylic acids are converted into their acid chlorides using standard reagents well known to someone skilled in the art, such as thionyl chloride, oxalyl chloride, phosphoryl chloride and the like. Those reagents can be used in presence of bases, such as DIPEA, TEA or pyridine.

Alternatively a carboxylic acid can be converted in situ into activated acids by treating the carboxylic acid with EDC, DCC, BOP, PyBrOP, or 2-fluoro-1-methylpyridinium p-toluenesulphonate (Mukaiyama's reagent) and the like, optionally in the presence of modifiers such as HOBt, with or without a base, such as NMM, TEA or DIPEA, in an inert solvent, such as DMF or DCM, at temperatures between 0° C. and 60° C. The reaction may alternatively be carried out in presence of HATU or HOAt and TEA or DIPEA in DMF, DCM or THF. Acylation of amines has been reviewed (J. March, supra pp. 417-425; H. G. Benz, Synthesis of Amides and Related Compounds in Comprehensive Organic Synthesis, E. Winterfeldt, ed., vol. 6, Pergamon Press, Oxford 1991 pp. 381-411; see R. C. Larock, Comprehensive Organic Transformations—A Guide to Functional Group Preparations, 1989, VCH Publishers Inc., New York; pp. 972-976).

The SCHEMES described above provide general procedures which have been applied to compounds encompassed in the present invention. The examples which follow contain additional details, which are useful to introduce the various structural features found in specific compounds.

Biological Activity

Determination of the ERK activity of a compound of formula I is possible by a number of direct and indirect detection methods. Certain exemplary compounds described herein were assayed for their ERK inhibitory activity (Example 7). The range of ERK binding activities was less than 1 nM (nanomolar) to about 10 μM (micromolar). A cell-based function assay (Example 9) was used to determine the effect of ERK inhibitors on down-stream signaling by assaying phosphorylation of P90RSK.

The cytotoxic or cytostatic activity of formula I exemplary compounds was measured by: establishing a proliferating mammalian tumor cell line in a cell culture medium, adding a formula I compound, culturing the cells for a period from about 6 h to about 5 d; and measuring cell viability (Example 8). Cell-based in vitro assays were used to measure viability, i.e., proliferation (IC$_{50}$), cytotoxicity (EC$_{50}$).

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit ERK activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment.

In one embodiment, the pharmaceutical composition also includes at least one additional anti-proliferative agent.

An embodiment, therefore, includes a pharmaceutical composition comprising a compound of Formula I, or a stereoisomer, tautomer or pharmaceutically acceptable salt thereof. A further embodiment includes a pharmaceutical composition comprising a compound of Formula I, or a stereoisomer, tautomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, metabolite, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The referential examples that follow illustrate procedures which prepare the amines required to assemble the ERK inhibitors encompassed in the present invention.

REFERENTIAL EXAMPLE 1

(3,4-dichlorophenyl)(oxazol-5-yl)methanamine hydrochloride (22)

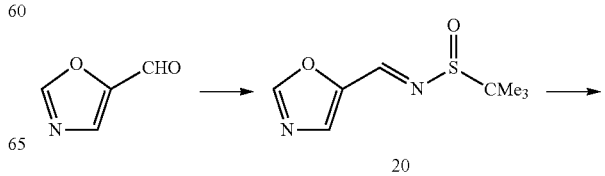

-continued

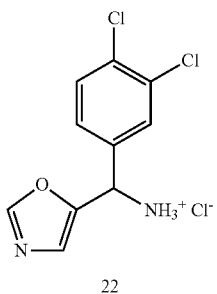

22 step 1: Oxazole-5-carbaldehyde (1.0 g, 10.30 mmol), 2-methylpropane-2-sulfinamide (2.247 g, 18.54 mmol; CASRN 146374-27-8), and tetraethoxytitanium (8.460 g, 37.09 mmol) were stirred in THF (15 mL) and heated to 65° C. for 12 h under nitrogen. The reaction was cooled and poured onto water. The solids were filtered off and the filtrate was extracted with EtOAc. The layers were separated and the organic layer was dried (MgSO₄), filtered and concentrated. The resulting residue was purified by SiO₂ chromatography eluting with an EtOAc/hexane gradient (20 to 25% EtOAc) to afford 1.211 g (58.7%) of (E)-2-methyl-N-(oxazol-5-ylmethylene)propane-2-sulfinamide (20).

step 2: A dried-flask was charged with 20 (1.211 g, 6.047 mmol) and toluene (5 mL) was added. The reaction was stirred under nitrogen, cooled to −78° C. and (3,4-dichlorophenyl)magnesium bromide (18.14 mL, 9.071 mmol, 0.5M in THF) was added. The reaction was then warmed to −10° C. for 15 min. Saturated ammonium chloride was added and the reaction was extracted with DCM. The organic layer was separated, dried (MgSO₄), filtered and concentrated. The resulting residue was dissolved in DCM (10 mL) then 4 N HCl in dioxane (15.12 mL, 60.47 mmol) was added and the solution was stirred for 30 min. The reaction mixture was added dropwise to a stirred solution of ether. The resulting solid was filtered and washed with ether to afford 1.24 g (73.3%) of (3,4-dichlorophenyl)(oxazol-5-yl)methanamine hydrochloride (22).

(4-Chloro-3-fluorophenyl)(isoxazol-5-yl)methanamine was prepared analogously except 5-isoxazolecarboxaldehyde (CASRN 16401-14-2) was used in place of oxazole-5-carbaldehyde and (3,4-dichlorophenyl)magnesium bromide was replaced with (4-chloro-3-fluorophenyl)magnesium bromide (53)

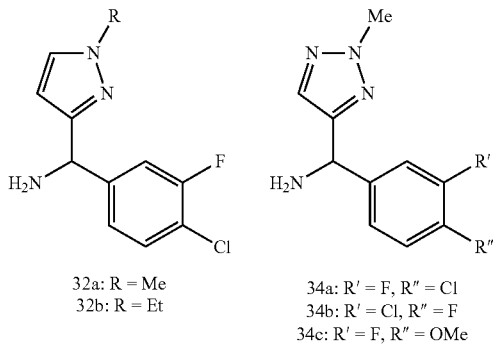

32a: R = Me
32b: R = Et

34a: R' = F, R'' = Cl
34b: R' = Cl, R'' = F
34c: R' = F, R'' = OMe (4-Chloro-3-fluoro-phenyl)-(1-methyl-1H-pyrazol-3-yl)-methylamine (32a) was prepared analogously except oxazole-5-carbaldehyde was replaced with 1-methyl-1H-pyrazole-3-carbaldehyde (CASRN 27258-32-8) and (4-chloro-3-fluorophenyl)magnesium bromide was used in place of (3,4-dichlorophenyl)magnesium bromide in step 2. (4-Chloro-3-fluoro-phenyl)-(1-ethyl-1H-pyrazol-3-yl)-methylamine (32b) was prepared analogously except oxazole-5-carbaldehyde was replaced with 1-ethyl-1H-pyrazole-3-carbaldehyde (CASRN 942319-16-6).

(4-Chloro-3-fluorophenyl)(2-methyl-2H-1,2,3-triazol-4-yl)methanamine (34a), (3-chloro-4-fluorophenyl)(2-methyl-2H-1,2,3-triazol-4-yl)methanamine (34b) and (3-fluoro-4-methoxyphenyl)(2-methyl-2H-1,2,3-triazol-4-yl)methanamine (34c) were prepared analogously from 2-methyl-2H-1,2,3-triazole-4-carbaldehyde (CASRN 1104078-88-7) using (4-chloro-3-fluorophenyl)magnesium bromide, (3-chloro-4-fluorophenyl)magnesium bromide and (3-fluoro-4-methoxyphenyl)magnesium bromide, respectively.

(4-Chloro-3-fluorophenyl)(1,2,4-oxadiazol-5-yl)methanamine was prepared analogously starting from 1,2,4-oxadiazole-5-carbaldehyde (CASRN 1083274-35-4).

REFERENTIAL EXAMPLE 2

4-chloro-3-fluorophenyl)(1H-pyrazol-4-yl)methanamine (40b

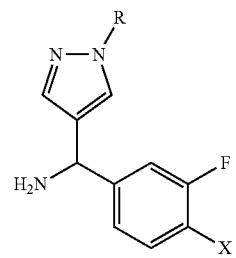

40b: R = H, X = Cl
40c: R = Me, X = Cl
40d: R = Et, X = Cl
40e: R = Me, X = OMe step 1: N-((1H-Pyrazol-4-yl)methylene)-2-methylpropane-2-sulfinamide (36) was prepared from 1H-pyrazole-4-carbaldehyde in accord with the procedure in step 1 of Referential Example 1.

step 2: To a solution of 36 (1.47 g, 7.378 mmol), Boc₂O (1.932 g, 8.852 mmol) and TEA (2.056 mL, 14.75 mmol) in MeCN (30 mL) at RT under nitrogen was added DMAP (0.09012 g, 0.7377 mmol) and the resulting solution was stirred for 1 h. Water was added and the reaction was extracted with ether. The organic layer was separated, dried (MgSO₄), filtered and concentrated. The crude residue was purified by SiO₂ chromatography eluting with 40% EtOAc/hexane to afford 2.14 g (96.9%) of (E)-tert-butyl 4-((tert-butylsulfinylimino)methyl)-1H-pyrazole-1-carboxylate (38).

step 3: (4-Chloro-3-fluorophenyl)(1H-pyrazol-4-yl) methanamine (40b) was prepared as described in step 2 of referential example 1 except (3,4-dichlorophenyl)magnesium bromide was replaced with (4-chloro-3-fluorophenyl) magnesium bromide.

One skilled in the art will appreciate that both (S)-2-methylpropane-2-sulfinamide (CASRN 343338-28-3) and (R)-2-methylpropane-2-sulfinamide (CASRN 196929-78-9) are commercially available and provide a stereoselective route to either enantiomer, e.g., (S)-(3-fluoro-4-methoxyphenyl)(1-methyl-1H-pyrazol-4-yl)methanamine (40f).

(4-Chloro-3-fluorophenyl)(1-methyl-1H-pyrazol-4-yl)methanamine (40c) and (4-chloro-3-fluorophenyl)(1-ethyl-1H-pyrazol-4-yl)methanamine (40d) were prepared analogously from 1-methyl-1-H-pyrazol-4-carboxaldehyde and 1-ethyl-1-H-pyrazol-4-carboxaldehyde, respectively as described in referential example 1. (3-Fluoro-4-methoxyphenyl)(1-methyl-1H-pyrazol-4-yl)methanamine (40e) and (3-chloro-4-methoxyphenyl)(1-methyl-1H-pyrazol-4-yl)methanamine (40f) were prepared analogously from 1-methyl-1H-pyrazol-4-carboxaldehyde and (3-fluoro-4-methoxyphenyl)magnesium bromide or (3-chloro-4-methoxyphenyl)magnesium bromide respectively. (S)-(4-(Difluoromethoxy)phenyl)(1-methyl-1H-pyrazol-4-yl)methanamine (40 g), (S)-4-(amino(1-methyl-1H-pyrazol-3-yl)methyl)-2-fluorobenzonitrile (40 h) and (S)-4-(amino(1-methyl-1H-pyrazol-3-yl)methyl)-2-chlorobenzonitrile (40i) were prepared analogously from 1-methyl-1H-pyrazol-4-carboxaldehyde and (4-difluoromethoxyphenyl)magnesium bromide, (4-cyano-3-fluorophenyl)magnesium bromide and (3-chloro-4-cyanophenyl)magnesium bromide respectively. (S)-(3-Fluoro-4-methoxyphenyl)(2-methyl-2H-1,2,3-triazol-4-yl)methanamine (40k) was prepared analogously from 2-methyl-2H-1,2,3-triazole-4-carbaldehyde and (3-fluoro-4-methoxyphenyl)magnesium bromide. (S)-(3-Fluoro-4-methoxyphenyl)(1-methyl-1H-pyrazol-4-yl)methanamine (40l) was prepared analogously from 1-methyl-1-H-pyrazol-4-carboxaldehyde and (3-chloro-4-fluorophenyl)magnesium bromide as described above. 5-[Amino-(1-methyl-1H-pyrazol-4-yl)-methyl]-2-methoxy-benzonitrile (40m) was prepared analogously from 1-methyl-1-H-pyrazol-4-carboxaldehyde and (3-cyano-4-methoxyphenyl)magnesium bromide. (3-Chloro-4-fluorophenyl)(1-methyl-1H-pyrazol-4-yl)methanamine (40n) was prepared analogously from 1-methyl-1-H-pyrazol-4-carboxaldehyde and (3-chloro-4-fluorophenyl)magnesium bromide.

REFERENTIAL EXAMPLE 3

R)-tert-butyl 2-((S)-amino(3-fluoro-4-(trifluoromethyl)phenyl)methyl) pyrrolidine-1-carboxylate (47a)

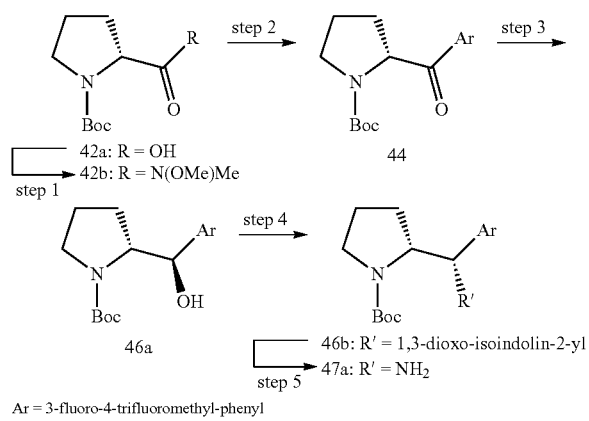

42a: R = OH
42b: R = N(OMe)Me
step 1

46a

46b: R' = 1,3-dioxo-isoindolin-2-yl
47a: R' = NH$_2$
step 5

Ar = 3-fluoro-4-trifluoromethyl-phenyl step 1: (R)-tert-butyl 2-(methoxy(methyl)carbamoyl)pyrrolidine-1-carboxylate. To a stirred solution of 42a (11.93 g, 55.42 mmol) and DCM (70 mL) cooled to −15° C. under nitrogen was added a solution of NMM (5.79 g, 57.3 mmol), ethyl carbonochloridate (12.03 g, 110.8 mmol) and DCM (50 mL) and the mixture was stirred for 15 min. Additional NMM (11.59 g, 114.5 mmol) was added followed by portionwise addition of O,N-dimethylhydroxylamine hydrochloride (10.81 g, 110.8 mmol). The reaction was stirred at RT for 18 h. The reaction was poured onto water and extracted with DCM. The organic layer was dried (MgSO$_4$) filtered, and concentrated and the crude residue was purified by SiO$_2$ chromatography eluting with EtOAc/hexane (1:1) to afford 9.74 g (68.03%) of 42b.

step 2: (R)-tert-butyl 2-(3-fluoro-4-(trifluoromethyl)benzoyl)pyrrolidine-1-carboxylate. To a stirred solution of 4-bromo-2-fluoro-1-(trifluoromethyl)benzene (4.854 g, 19.98 mmol) and ether (50 mL) cooled to −78° C. under nitrogen was added n-butyl lithium (7.99 mL, 19.98 mmol) slowly over 10 min. The reaction was transferred via cannula to a solution of 42b (4.30 g, 16.65 mmol) in THF (50 mL) cooled to −78° C. The reaction was stirred for 10 min after all aryl lithium was added. The reaction was quenched with water and extracted with DCM. The organic layer was dried (MgSO$_4$), concentrated and the crude product purified by SiO$_2$ chromatography eluting with an EtOAc/hexane gradient (1 to 5% EtOAc). A close running impurity was not removed by this purification. The compound was further purified on a SP4 reverse phase column chromatography eluting with MeCN/water gradient (65 to 100% MeCN) to afford 2.105 g (33.2%) of 44.

step 3: (R)-tert-butyl 2-((R)-(3-fluoro-4-(trifluoromethyl)phenyl)(hydroxy)methyl)pyrrolidine-1-carboxylate. To a stirred solution of 44 (1.797 g, 4.973 mmol) in MeOH (50 mL) under nitrogen and cooled to 0° C. was added NaBH$_4$ (188.2 mg, 4.973 mmol) and the reaction was stirred at 0° C. for 1 h. Ice was slowly added and the resulting mixture was stirred for 10 min. The mixture was extracted with DCM, dried (MgSO$_4$) and concentrated to afford 1.8 g (quantitative yield) of crude 46a which was used without further purification.

step 4: (R)-tert-Butyl 2-((S)-(1,3-dioxoisoindolin-2-yl)(3-fluoro-4-(trifluoromethyl)phenyl)methyl)pyrrolidine-1-carboxylate 46a (1.807 g, 4.973 mmol) was placed in THF (50 mL) and cooled to 0° C. Isoindoline-1,3-dione (0.8049 g, 5.471 mmol) and PPh$_3$ (1.957 g, 7.460 mmol) were added, followed by the drop wise addition of DEAD (2.937 mL, 7.460 mmol). The reaction was then allowed to warm to RT, stir for 20 h and was then concentrated to dryness. Ether (300 mL) was then added, and the resulting solid was filtered and discarded. The filtrate was then poured into water and extracted with DCM. The combined organic fractions were dried (MgSO$_4$), filtered and concentrated to give the crude product, which was purified by SiO$_2$ chromatography to give 1.036 g (42.30% yield) of 46b.

step 5: (2R)-tert-butyl 2-((S)-amino(3-fluoro-4-(trifluoromethyl)phenyl)methyl)pyrolidine-1-carboxylate. 46b (1.036 g, 2.104 mmol) was placed in 1:1 THF:MeOH (50 mL). Hydrazine monohydrate (1.053 g, 21.04 mmol) was then added, and the reaction was stirred at RT for 48 h. The reaction was then diluted with THF and filtered. The solid (hydrazine byproduct) was discarded. The filtrate was concentrated and purified by column chromatography eluting with a MeOH/DCM gradient (1-4% MeOH) to afford 596 mg (78%) of 47a.

(R)-tert-butyl 2-((S)-amino(4-chloro-3-fluorophenyl)methyl)pyrrolidine-1-carboxylate (47b) and (R)-tert-butyl 2-((S)-amino(3-fluoro-4-methoxyphenyl)methyl)pyrrolidine-1-carboxylate (47c) can be prepared analogously except in step 1, 42a is replaced by 1-bromo-4-chloro-3-fluoro-benzene and 4-bromo-2-fluoro-1-methoxy-benzene respectively.

(2R,5R)-5-Methyl-pyrrolidine-2-carboxylic acid was prepared in accord with the procedure described by F. A. Davis et al. Org. Lett. 2001 3(5):759-762 and converted to (2R,5R)-tert-butyl 2-((S)-amino(4-chloro-3-fluorophenyl)methyl)-5-methylpyrrolidine-1-carboxylate (48) as described hereinabove.

(2R,4S)-4-Fluoropyrrolidine-2-carboxylic acid was converted to (2R,4S)-tert-butyl 2-((S)-amino(3-fluoro-4-methoxyphenyl)methyl)-4-fluoropyrrolidine-1-carboxylate (49) as described hereinabove.

REFERENTIAL EXAMPLE 4

S)-tert-butyl 2-((S)-amino(3-fluoro-4-(trifluoromethyl)phenyl)methyl)pyrrolidine-1-carboxylate (55)

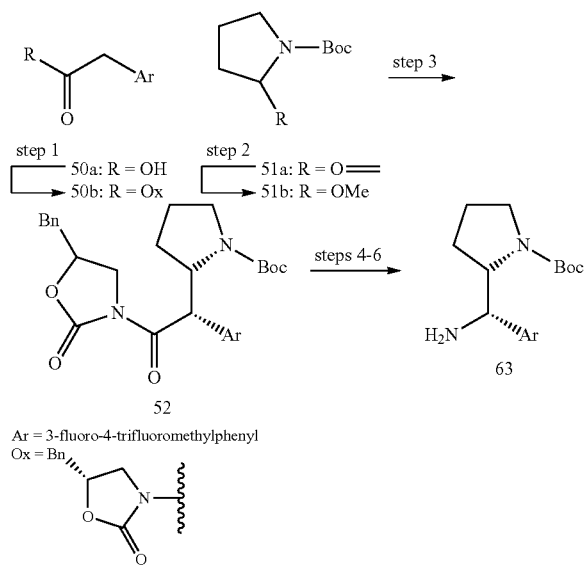

step 1: (R)-4-benzyl-3-(2-(3-fluoro-4-(trifluoromethyl)phenyl)acetyl)oxazolidin-2-one (50b). To a solution of 50a (16.8 g, 75.6 mmol) in ether (150 mL) cooled to 0° C. was added slowly DIPEA (13.2 mL, 75.6 mmol) followed by trimethylacetyl chloride (9.31 mL, 75.6 mmol). The mixture was agitated at 0° C. for 1 h and filtered, and the solids were washed with ether (100 mL). The filtrate was then cooled to −78° C. Meanwhile, (R)-(+)-4-benzyl-2-oxazolidinone (13.4 g, 75.6 mmol) in THF (150 mL) was cooled to −78° C., and a 2.5 M hexane solution of butyl lithium (30.3 mL, 75.6 mmol) was added slowly. The mixture was agitated for 15 min at −78° C. and transferred by cannula to the solution of the mixed anhydride. The resulting solution was agitated at −78° C. for 15 min, allowed to warm up to 0° C. and agitated an additional 30 min. The reaction was quenched with saturated NH$_4$Cl (50 mL), diluted with EtOAc (500 mL) and washed sequentially with water, aqueous NaHCO$_3$ and brine, dried (MgSO$_4$), and evaporated. The solidified residue (~30 g) was recrystallized from EtOH (ca. 150 mL) to afford 13.0 g (45.1%) of 50b as crystalline solid.

step 2: tert-butyl 2-methoxypyrrolidine-1-carboxylate (51b). To a solution of 51a (20.0 g, 107.98 mmol) in dry Et$_2$O (250 mL) cooled to −78° C. was added portionwise 1M DIBAL-H solution in toluene (73.426 mL, 110.14 mmol). The mixture was stirred for 1 h at −78° C., then allowed to warm to RT and stirred overnight. The reaction mixture was cooled to 0° C., and saturated NH$_4$Cl (50 mL) was added, followed by 1M Rochelle's Salt solution (300 mL). The mixture was transferred to a 2 L Erlenmeyer flask, more ether was added, and it was stirred vigorously for 1 h (emulsion loosens and separates over this time). The mixture was transferred to a separatory funnel, the aqueous solution was drained, and the organics were washed with Rochelle's Salt solution and brine, dried (Na$_2$SO$_4$), filtered, and concentrated. The resulting oil was then concentrated one time from MeOH. The resulting oil was dissolved in MeOH (250 mL) and p-TsOH monohydrate (1.0270 g, 5.3990 mmol) was added. The reaction mixture was stirred for 48 h at RT. The mixture was concentrated and the residue was taken up in DCM (300 mL), and this solution was poured into saturated NaHCO$_3$ (300 mL). The mixture was extracted with DCM, and the combined organic layers were dried (Na$_2$SO$_4$), filtered, and concentrated to afford 20.09 g (92%) of 51b as an oil.

step 3: (S)-tert-butyl 5-((S)-2-((R)-4-benzyl-2-oxooxazolidin-3-yl)-1-(3-fluoro-4-(trifluoromethyl)phenyl)-2-oxoethyl)-2,2-dimethylpyrrolidine-1-carboxylate (52). To a solution of 50b (2.00 g, 5.24 mmol) in DCM (25 mL) cooled to −78° C. was added slowly a TiCl$_4$ (5.51 mL, 5.51 mmol, 1M solution in toluene) followed by drop wise addition of DIPEA (0.959 mL, 5.51 mmol). The resulting deep purple mixture was agitated at −78° C. for 15 min. A solution of 51b (1.38 g, 6.03 mmol) in DCM (5 mL) was added, and the mixture was agitated for 15 min at −78° C. and then allowed to warm up over 1 h. The reaction was quenched with NH$_4$Cl (20 mL), diluted with DCM (250 mL), washed sequentially with water, aqueous NaHCO$_3$, dried (MgSO$_4$), and evaporated to a thick oil. The crude product was purified by SiO$_2$ chromatography eluting with 15% EtOAc/hexane to afford 1.69 g (55.7%) of 52 as foamy solid.

step 4: (S)-2-((S)-1-(tert-butoxycarbonyl)pyrrolidin-2-yl)-2-(3-fluoro-4-(trifluoromethyl)phenyl)acetic acid (57). To a solution of THF (100 mL), water (50 mL) and 1M LiOH (5.70 mL, 5.70 mmol) cooled to 0° C. was added H$_2$O$_2$ (0.728 mL, 7.13 mmol) and the mixture was agitated for 10 min. A solution of 52 (1.65 g, 2.85 mmol) in THF (20 mL) was added, and the mixture was allowed to warm to RT and agitate overnight. 1M Na$_2$SO$_3$ (20 mL) was added, and the mixture was agitated for 15 minutes. The mixture was acidified with 2M KHSO$_4$, and brine (100 mL) was added. The aqueous phase was separated and extracted twice with EtOAc. The combined organics were washed with brine, dried (MgSO$_4$), filtered and evaporated. The crude product was purified by SiO$_2$ chromatography (Flash 40L) eluting with 20% EtOAc/hexane containing 1% HOAc to afford 1.0 g (83.6%) of 57 as a solid.

step 5: (S)-tert-butyl 2-((S)-(((benzyloxy)carbonyl)amino)(3-fluoro-4-(trifluoromethyl)phenyl)methyl)pyrrolidine-1-carboxylate (61). To a solution of DIPEA (0.598 mL, 3.43 mmol), diphenylphosphoryl azide (0.591 mL, 2.74 mmol) and toluene (15 mL) was added 57 (0.895 g, 2.29 mmol). After agitating for 30 min, the mixture was heated to 100° C. and agitated for 3 h. The mixture was then cooled to 70° C., and benzyl alcohol (2 mL, 18.5 mmol) was added and the mixture stirred overnight. After evaporating to dryness, the crude product was purified by SiO$_2$ chromatography eluting with an EtOAc/hexane gradient (10 to 20% EtOAc) to afford 1.04 g (88%) of 61 as a solid.

step 6: (S)-tert-butyl 2-((S)-amino(3-fluoro-4-(trifluoromethyl)phenyl)methyl)pyrrolidine-1-carboxylate (63). To a solution of 61 (1.04 g, 2.09 mmol) and EtOH (25 mL), was added Pd/C (10% Degussa wet, 0.5 g). The mixture was hydrogenated overnight under balloon pressure. The mixture was then filtered and evaporated to afford 0.52 g (68.5%) of 63 as thick oil.

(S)-tert-Butyl 2-((S)-amino(4-chloro-3-fluorophenyl)methyl)pyrrolidine-1-carboxylate (65) can be prepared analogously except in step 1, 3-fluoro-4-(trifluoromethyl)phenylacetic acid (50a) is replaced by 3-fluoro-4-chlorophenyl acetic acid.

REFERENTIAL EXAMPLE 5

S)-tert-butyl 3-(amino(3-chloro-4-fluorophenyl)methyl)pyrrolidine-1-carboxylate (73a/73b)

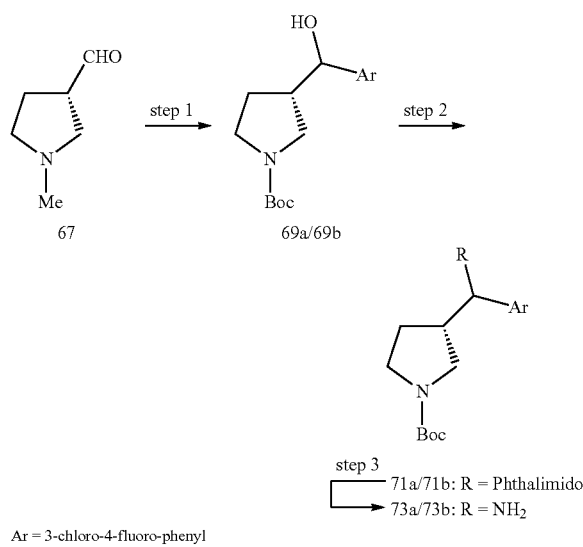

Ar = 3-chloro-4-fluoro-phenyl step 1: (3S)-tert-butyl 3-((3-chloro-4-fluorophenyl)(hydroxy)methyl)pyrrolidine-1-carboxylate (69a/69b). To a stirred solution of (S)-tert-butyl 3-formylpyrrolidine-1-carboxylate (67)(367.3 mg, 1.843 mmol) in THF (9.2 mL, 0.2 M) under nitrogen atmosphere cooled to 0° C. and degassed with $N_2$ was added dropwise a THF solution of (3-chloro-4-fluorophenyl)magnesium bromide (4056 µL, 2.028 mmol) and the solution stirred at 0° C. for 3 h. The reaction was then quenched by addition of water (3 mL) THF was removed by rotovap, and the mixture was extracted with EtOAc (2×30 mL). The combined organics were washed with water (2×30 mL) and brine (1×30 mL). The organic extracts were dried ($Na_2SO_4$), filtered and concentrated. The crude product was loaded onto an SP1 samplet and purified by chromatography eluting a DCM/acetone gradient (2 to 45% acetone) to afford 364 mg (60%) of 69a/69b as an approximate 1:1 mixture of diastereomers as a clear oil which was used without additional purification.

step 2: (3S)-tert-butyl 3-((3-chloro-4-fluorophenyl)(1,3-dioxoisoindolin-2-yl)methyl)pyrrolidine-1-carboxylate (71a/71b). To a solution of 69a/69b (364.3 mg, 1.105 mmol) in THF (5.5 mL, 0.2 M) under nitrogen was added phthalimide (178.8 mg, 1.215 mmol) and $PPh_3$ (376.7 mg, 1.436 mmol). The reaction was cooled to 0° C. and diethyl azodicarboxylate (654.0 µL, 1.436 mmol) was added dropwise via syringe. The reaction was allowed to warm to RT and stirred for 16 h. The reaction was concentrated to dryness by rotovap, diluted to 30 mL with EtOAc and washed with water (2×30 mL) and brine (1×30 mL). The organics were isolated, dried ($Na_2SO_4$), filtered and concentrated. The crude product was purified by $SiO_2$ chromatography eluting with a hexanes/acetone gradient (5 to 70% acetone) to afford 212 mg (42%) of 71a/71b as a clear oil containing approximately a 1:1 mixture of diastereomers.

step 3: (S)-tert-butyl 3-(amino(3-chloro-4-fluorophenyl)methyl)pyrrolidine-1-carboxylate (73a/73b). A solution of 71a/71b (212.3 mg, 0.4626 mmol) in 1:1 THF:MeOH (2.3 mL, 0.2 M) was treated with hydrazine monohydrate (224.4 µL, 4.626 mmol) and heated to 60° C. overnight. The reaction was cooled to RT, and the solids were filtered off. The filtrate was concentrated to dryness and taken up in EtOAc (30 mL). The EtOAc solution was washed with saturated $NaHCO_3$ (2×30 mL) and brine (1×30 mL). The organics were isolated, dried ($Na_2SO_4$), filtered and concentrated. The crude product was purified by $SiO_2$ chromatography eluting with a 1-25% gradient of MeOH/3% $NH_4OH$ in DCM to afford 110 mg (72%) of 73a/73b as a clear oil containing approximately a 1:1 mixture of diastereomers.

(R)-tert-Butyl 3-(amino(3-chloro-4-fluorophenyl)methyl)pyrrolidine-1-carboxylate (75a/75b) can be prepared analogously, except in step 1 (R)-tert-butyl 3-formylpyrrolidine-1-carboxylate is substituted for (S)-tert-butyl 3-formylpyrrolidine-1-carboxylate (67).

REFERENTIAL EXAMPLE 6

3S,4S)-3-fluorotetrahydro-2H-pyran-4-amine (60c) and (3R,4R)-3-fluorotetrahydro-2H-pyran-4-amine (60d)

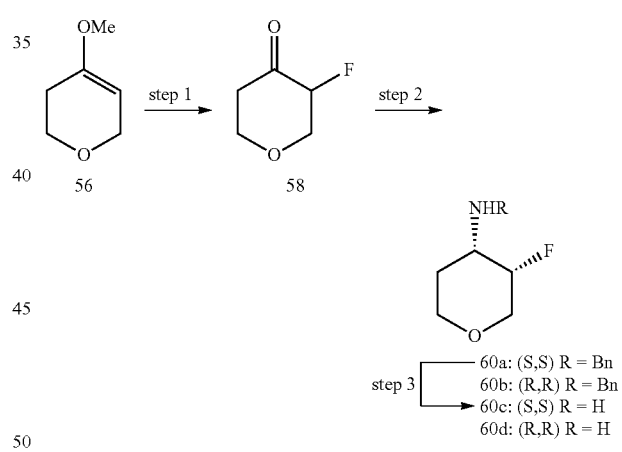

step 1: To a stirred solution of 1-chloromethyl-4-fluoro-1,4-diazoniabicyclo[2.2.2]octane bis-tetrafluoroborate (147 g, 414 mmol, Selectfluor®) in MeCN/$H_2O$ (1:1, 800 mL) cooled to 0° C. under nitrogen in a 3 L round-bottom flask was added dropwise a solution of 56 (45.0 g, 394 mmol, CASRN 17327-22-9) in MeCN (120 mL). The reaction was stirred for 30 min. in an ice bath before the bath was removed and the reaction was stirred for an additional 1 h. Solid NaCl (200 g) was then added to the reaction along with DCM (300 mL). A saturated $Na_2CO_3$ solution was added slowly until pH was 10. The mixture was transferred into a 4 L sep. funnel and thrice extracted into DCM. The aqueous layer was then placed in a continuous liquid-liquid extractor with DCM and heated to 58° C. for 18 h. The combined organic extracts were dried ($MgSO_4$), filtered and concentrated at 20° C. on the rotovap. The crude product was purified by $SiO_2$ chromatography eluting with DCM/MeOH gradient (500:3 to 500:5 DCM: MeOH) to afford 30 g (64.4%) of 3-fluorodihydro-2H-pyran-4(3H)-one (58).

step 2: To a solution of 58 (30 g, 254 mmol) and DCE (800 mL) cooled to 0° C. under nitrogen was added phenylmethanamine (29.8 mL, 267 mmol) and the solution was stirred for 10 min. To the reaction mixture was added $NaBH(OAc)_3$ (75.4 g, 356 mmol) followed by the dropwise addition of glacial HOAc (14.5 mL, 254 mmol). The reaction was stirred for 2 h and then poured into 1M NaOH and extracted with DCM. The combined organic fractions were dried ($MgSO_4$), filtered and concentrated. The crude product was purified by reverse phase column chromatography using a $MeCN/H_2O$ gradient (0 to 40% MeCN) to afford 39 g (73.4%) of the racemic cis product [(3S,4S)— and (3R,4R)—N-benzyl-3-fluorotetrahydro-2H-pyran-4-amine 60a and 60b respectively].

The enantiomers can be separated by chromatography on a Chiralpak IC, 5×25 cm column eluting with 10% IPA (0.1% $NH_4OH$)/90% $CO_2$ at a flow rate of 300 mL/min and a temperature of 40° C. The back pressure was 100 Bar.

step 3: To a solution of 60a (3.7 g, 18 mmol) and MeOH (40 mL) at RT was added Pd/C (3.8 g, 1.8 mmol) and the resulting suspension stirred under $H_2$ for 18 h. The catalyst was filtered, washed with MeOH. The solvent was concentrated to afford 2.1 g (100%) (3S,4S)-3-fluorotetrahydro-2H-pyran-4-amine (60c): $H^1$ NMR (400 MHz, $CDCl_3$) δ 4.58-4.44 (m, 1H), 4.19-4.09 (m, 1H), 4.05-3.95 (m, 1H), 3.56-3.38 (m, 2H), 2.96-2.84 (m, 1H), 1.88-1.77 (m, 1H), 1.72-1.65 (m, 1H) The enantiomer, (3R,4R)-3-fluorotetrahydro-2H-pyran-4-amine (60d), can be prepared analogously by repacing 60a with 60b.

REFERENTIAL EXAMPLE 7

3S,4R)-3-fluorotetrahydro-2H-pyran-4-amine (66a) and (3R,4S)-3-fluorotetrahydro-2H-pyran-4-amine (66b)

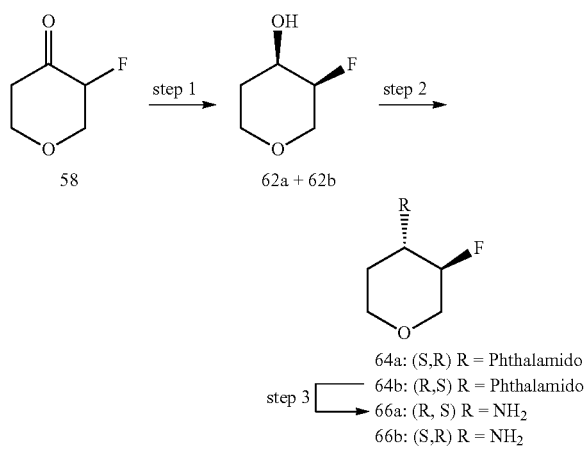

step 1: To a stirred solution of 58 (34.58 g, 292.8 mmol) and THF (350 mL) cooled to −78° C. under nitrogen was added drop wise L-selectride (307.4 mL, 307.4 mmol) and the reaction was stirred for 30 min. MeOH (35.58 mL, 878.4 mmol) and 1M NaOH (878.4 mL, 878.4 mmol) were then added, and the reaction was allowed to warm to 0° C. To the solution was added dropwise with care $H_2O_2$ (99.59 mL, 1464 mmol) and the reaction was stirred for an additional 30 min. Saturated brine (50 mL) was then added, and the reaction was concentrated to remove THF. The solution was diluted with DCM (500 mL) and transferred to a liquid-liquid continuous extractor, which was heated at 58° C. for 24 h. The organic fraction was then separated, dried ($MgSO_4$), filtered and concentrated. The crude product was purified by $SiO_2$ chromatography eluting with a DCM/EtOAc gradient (5:1 to 3:1) to afford 21 g (60.2%) of the racemic cis product (3R,4S)— and (3S,4R)-3-fluorotetrahydro-2H-pyran-4-ol (62a and 62b respectively).

step 2: To a stirred solution of 62a and 62b (15.0 g, 125 mmol), isoindoline-1,3-dione (20.2 g, 137 mmol), and 2-(diphenylphosphino)pyridine (42.7 g, 162 mmol) and THF (550 mL) cooled to 0° C. under nitrogen was added (E)-di-tert-butyl diazene-1,2-dicarboxylate (37.4 g, 162 mmol) and the reaction stirred at RT for 24 h. To the reaction mixture was added 4M HCl in dioxane (156 mL, 624 mmol) and the resulting solution stirred for 2 h then concentrated to dryness. The residue was dissolved in ether and washed six times with 4M HCl. The solids that did not dissolve in ether were set aside for later purification (batch 1). The organic solution was then dried ($MgSO_4$), filtered and concentrated. The crude material was suspended in THF and filtered, giving solid product (batch 2). The filtrate was next concentrated, resuspended in DCM and filtered. The solid was discarded. The filtrate was combined with the first two batches of solids (batches 1 and 2), concentrated, and purified by $SiO_2$ chromatography eluting with a DCM/MeOH gradient (500:2 to 500:5) to afford 14 g (45%) of racemic 2-((3S,4R) and (3R,4S)-3-fluorotetrahydro-2H-pyran-4-yl)isoindoline-1,3-dione (64a and 64b respectively).

The enantiomers were separated by chromatography on a Chiralpak IA, 5×25 cm column eluting with 10% MeOH: DCM(1:1)/90% $CO_2$ at a flow rate of 300 mL/min and a temperature of 40° C. The back pressure was 100 Bar.

step 3: To a solution of 64b (8.4 g, 34 mmol) and THF/MeOH (1:1, 160 mL) was added hydrazine monohydrate (17 g, 337 mmol) and the reaction was stirred at 50° C. for 6 h, then cooled to RT for 24 h. The resulting mixture was filtered and the solid washed with THF. The filtrate was concentrated and the crude product was purified by $SiO_2$ chromatography eluting with a DCM:MeOH gradient (500:20 to 500:25) to afford 4.0 g (100%) of (3R,4S)-3-fluorotetrahydro-2H-pyran-4-amine (66a): $H^1$ NMR (400 MHz, $CDCl_3$) δ 4.28-4.04 (m, 2H), 3.94-3.85 (m, 1H), 3.45-3.35 (m, 1H), 3.30-3.20 (m, 1H), 3.05-2.92 (m, 1H), 1.97-1.88 (m, 1H), 1.58-1.48 (m, 1H). The other enantiomer, (3R,4S)-3-fluorotetrahydro-2H-pyran-4-amine (66b), was prepared analogously from 64b.

EXAMPLE 1

N-((4-chloro-3-fluorophenyl)(1-methyl-1H-pyrazol-4-yl)methyl)-2-((S)-1-hydroxypropan-2-ylamino) quinazoline-7-carboxamide (I-1)

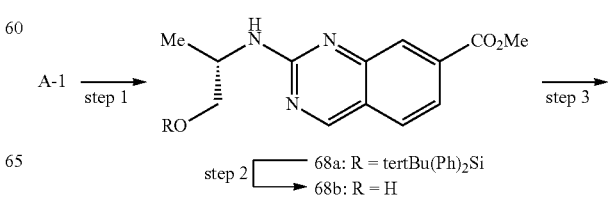

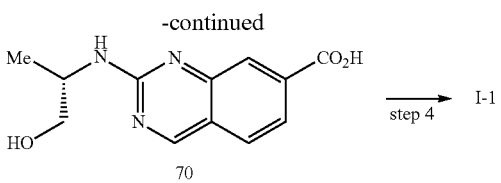

(S)-1-(tert-butyldiphenylsilyloxy)propan-2-amine (67)—To a stirred solution of (S)-2-aminopropan-1-ol (3.0 g, 39.9 mmol) and DCM (20 mL) at RT under nitrogen was added TEA (11.1 mL, 79.9 mmol) and DMAP (0.488 g, 3.99 mmol) and the resulting solution stirred for 10 min. tert-Butyldiphenylsilyl chloride (12.1 g, 43.9 mmol) was added, and the reaction was stirred for 18 h, then poured into water, and extracted with DCM. The combined organic fractions were dried (MgSO$_4$), filtered, and concentrated to afford a crude product that was purified by SiO$_2$ chromatography eluting with 10% MeOH/DCM to afford 9.5 g (75.9%) of 67.

step 1: A stirred solution of methyl 2-chloroquinazoline-7-carboxylate (A-1, 3.0 g, 13 mmol), 67 (5.1 g, 16 mmol), DBU (4.1 g, 27 mmol) and MeCN (30 mL) under nitrogen was heated to 60° C. for 18 h. The reaction was then cooled to RT, and poured into water, and extracted with DCM. The combined organic fractions were dried (MgSO$_4$), filtered, and concentrated to afford a crude product that was purified by SiO$_2$ chromatography eluting with 1% MeOH/MeOH to afford 5.1 g (76%) of 68a.

step 2: To a stirred solution of 68a (5.0 g, 10 mmol) and THF (10 mL/g) at RT was added TBAF (12 mL, 12 mmol, 1M solution in THF) and the reaction was stirred at RT for 1 h, then poured into H$_2$O, and extracted with DCM. The combined organic fractions were dried (MgSO$_4$), filtered and concentrated. The crude product was purified by SiO$_2$ chromatography eluting with a MeOH/DCM gradient (1 to 3% MeOH) to afford 2.5 g (96%) of 68b.

step 3: To a stirred solution of 68b (2.5 g, 9.6 mmol) and THF (50 mL) was added MeOH (10 mL) followed by 1M NaOH (38 mL, 38 mmol) and the resulting mixture was stirred at RT for 1 h. The reaction was then concentrated and acidified to pH 2 with 1M HCl which afforded a yellow precipitate that was filtered, washed with water and then ether and dried to afford 1.6 g (68%) of (S)-2-(1-hydroxypropan-2-ylamino)quinazoline-7-carboxylic acid (70).

step 4: To a stirred solution of the hydrochloride salt of 40c (140 mg, 0.506 mmol), and DIPEA (88.1 µL, 0.506 mmol) and DMF (5 mL) under nitrogen was added 70 (125 mg, 0.506 mmol) and HBTU (211 mg, 0.556 mmol) and the reaction was stirred at RT for 18 h. The reaction was poured into water and extracted with EtOAc. The combined extracts were dried (MgSO$_4$) and evaporated and the crude material was purified by reverse phase chromatography (SP4) eluting with a MeCN/H$_2$O gradient (10 to 95% MeCN) to afford 83.5 mg (35.2%) of N-((4-chloro-3-fluorophenyl)(1-methyl-1H-pyrazol-4-yl)methyl)-2-((S)-1-hydroxypropan-2-ylamino)quinazoline-7-carboxamide (I-1).

2-(Isopropylamino)quinazoline-7-carboxylic acid (69a), (S)-2-(1,1,1-trifluoropropan-2-ylamino)quinazoline-7-carboxylic acid (69b), (R)-2-(1-cyclopropylethylamino)quinazoline-7-carboxylic acid (69c), 2-((3S,4S)-3-fluorotetrahydro-2H-pyran-4-ylamino)quinazoline-7-carboxylic acid (69d), 2-((3R,4S)-3-fluorotetrahydro-2H-pyran-4-ylamino)quinazoline-7-carboxylic acid (69e) and 2-(tetrahydro-2H-pyran-4-ylamino)quinazoline-7-carboxylic acid (69f), 2-((3R,4R)-3-fluorotetrahydro-2H-pyran-4-ylamino)quinazoline-7-carboxylic acid (69g) and 2-((3R, 4S)-3-fluorotetrahydro-2H-pyran-4-ylamino)quinazoline-7-carboxylic acid (69h) were prepared analogously using steps 1 and 3, except 67 was replaced with iso-propyl amine, (S)-1,1,1-trifluoropropan-2-amine, (R)-1-cyclopropylethanamine, 60c, 66a, 4-amino-tetrahydropyran, 60d and 66b respectively.

2-(Tetrahydro-pyran-4-ylamino)-quinazoline-7-carboxylic acid [(4-chloro-3-fluoro-phenyl)-(1-methyl-1H-pyrazol-4-yl)-methyl]-amide (I-2), 2-(tetrahydropyran-4-ylamino)-quinazoline-7-carboxylic acid [(4-chloro-3-fluoro-phenyl)-(1-methyl-1H-pyrazol-3-yl)-methyl]-amide (I-4), N-((4-chloro-3-fluorophenyl)(1-methyl-1H-pyrazol-3-yl)methyl)-2-((S)-1-hydroxypropan-2-ylamino)quinazoline-7-carboxamide (I-6), 2-(tetrahydropyran-4-ylamino)-quinazoline-7-carboxylic acid [(S)-(4-chloro-3-fluoro-phenyl)-(1-methyl-1H-pyrazol-4-yl)-methyl]-amide (I-12), 2-(tetrahydropyran-4-ylamino)-quinazoline-7-carboxylic acid [(R)-(4-chloro-3-fluoro-phenyl)-(1-methyl-1H-pyrazol-4-yl)-methyl]-amide (I-13), 2-((S)-2-hydroxy-1-methyl-ethylamino)-quinazoline-7-carboxylic acid [(R)-(4-chloro-3-fluoro-phenyl)-(1-methyl-1H-pyrazol-4-yl)-methyl]-amide (I-14), 2-((S)-2-hydroxy-1-methyl-ethylamino)-quinazoline-7-carboxylic acid [(S)-(4-chloro-3-fluoro-phenyl)-(1-methyl-1H-pyrazol-4-yl)-methyl]-amide (I-15), 2-(tetrahydropyran-4-ylamino)-quinazoline-7-carboxylic acid [(R)-(4-chloro-3-fluoro-phenyl)-(1-ethyl-1 H-pyrazol-3-yl)-methyl]-amide (I-18), 2-(tetrahydropyran-4-ylamino)-quinazoline-7-carboxylic acid [(S)-(4-chloro-3-fluoro-phenyl)-(1-ethyl-1H-pyrazol-3-yl)-methyl]-amide (I-19), 2-(tetrahydropyran-4-ylamino)-quinazoline-7-carboxylic acid [(S)-(4-chloro-3-fluoro-phenyl)-(1-methyl-1H-pyrazol-3-yl)-methyl]-amide (I-20) 2-(tetrahydropyran-4-ylamino)-quinazoline-7-carboxylic acid [(R)-(4-chloro-3-fluoro-phenyl)-(1-methyl-1H-pyrazol-3-yl)-methyl]-amide (I-21), 2-((3R,4R)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide (I-27), 2-((3S,4S)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide (I-28), 2-((3R,4S)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide (I-29), 2-((3S,4R)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide (I-30), 2-(tetrahydropyran-4-ylamino)-quinazoline-7-carboxylic acid [(S)-(3-fluoro-4-methoxy-phenyl)-(1-methyl-1H-pyrazol-4-yl)-methyl]-amide (I-32), 2-(tetrahydro-pyran-4-ylamino)-quinazoline-7-carboxylic acid [(4-chloro-3-fluoro-phenyl)-[1,2,4]oxadiazol-5-yl-methyl]-amide (I-34), 2-(tetrahydropyran-4-ylamino)-quinazoline-7-carboxylic acid [(S)-(4-difluoromethoxy-phenyl)-(1-methyl-1H-pyrazol-4-yl)-methyl]-amide (I-41), 2-(tetrahydro-pyran-4-ylamino)-quinazoline-7-carboxylic acid [(S)-(3-chloro-4-methoxy-phenyl)-(1-methyl-1H-pyrazol-4-yl)-methyl]-amide (I-44), 2-(tetrahydro-pyran-4-ylamino)-quinazoline-7-carboxylic acid [(R)-(4-cyano-3-fluoro-phenyl)-(1-methyl-1H-pyrazol-4-yl)-methyl]-amide (I-45), (R)—N-((3-chloro-4-cyanophenyl)(1-methyl-1H-pyrazol-4-yl)methyl)-2-(tetrahydro-2H-pyran-4-ylamino)quinazoline-7-carboxamide (I-48), (R)—N-((3-cyano-4-methoxyphenyl)(1-methyl-1H-pyrazol-4-yl)methyl)-2-(tetrahydro-2H-pyran-4-ylamino)quinazoline-7-carboxamide (I-49) and (S)-N-((3-chloro-4-cyanophenyl)(1-methyl-1H-pyrazol-4-yl)methyl)-2-(tetrahydro-2H-pyran-4-ylamino)quinazoline-7-carboxamide (I-50) were prepared analogously from the appropriate 2-substituted-quinazoline-7-carboxylic acid and the appropriate amine.

One skilled in the art will appreciate that the compounds can be either administered as racemic mixtures or resolved enantiomers. The enantiomers can be prepared by resolution of the racemates on chiral HPLC support, for example, using a Chiral Tech IC column (4.6 mm×250 mm,) eluting with EtOH/hexane at a flow rate of 1 mL/min. Alternately the amines can be prepared by chiral synthesis using chiral N-tert-butylsulfinyl imines (C-2) affording chiral amines. Coupling of the chiral amines affords the pure enantiomers directly.

2-Substituted-quinazoline-7-carboxylic acid wherein the 2-amino substituent is enantiomerically pure form when condensed with a racemic amine result in a diastereomeric mixture which can be separated using standard $SiO_2$ or reverse phase chromatography.

2-(Tetrahydro-pyran-4-ylamino)-quinazoline-7-carboxylic acid [(S)-(3-chloro-4-fluoro-phenyl)-(1-methyl-1H-pyrazol-4-yl)-methyl]-amide (I-55) was prepared analogously from 69f and (S)-40n.

2-(Tetrahydro-pyran-4-ylamino)-quinazoline-7-carboxylic acid [(3-cyano-4-methoxy-phenyl)-(1-methyl-1H-pyrazol-4-yl)-methyl]-amide (I-56) was prepared analogously from 69f and (S)-40m.

EXAMPLE 2

2-(tetrahydropyran-4-ylamino)-quinazoline-7-carboxylic acid [(3-chloro-4-fluoro-phenyl)-(3-fluoro-pyrrolidin-3-yl)-methyl]-amide (I-16)

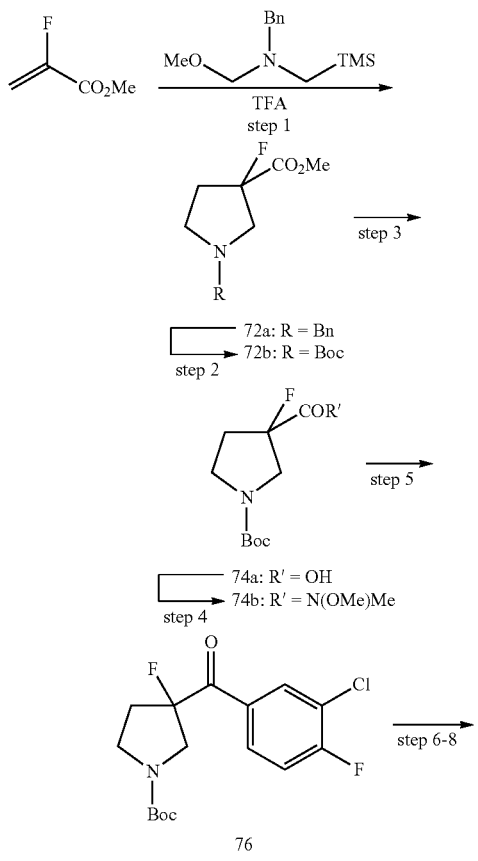

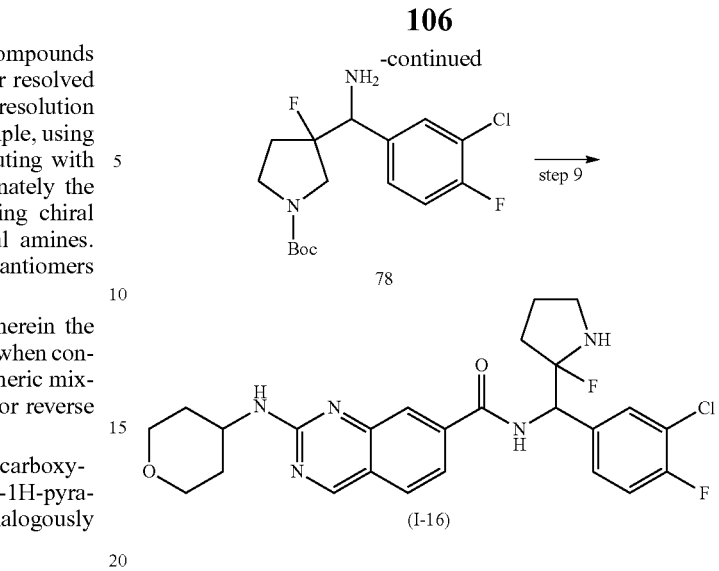

step 1: A 0.3 M solution of methyl 2-fluoroacrylate (4.37 g, 41.99 mmol) and DCM (140 mL) was stirred under nitrogen and cooled to 0° C. The reaction mixture was then treated with N-benzyl-1-methoxy-N-((trimethylsilyl)methyl)methanamine (10.47 g, 44.09 mmol) followed by TFA (1.56 mL, 20.99 mmol). The reaction mixture was warmed to RT and stirred for 16 h. The reaction mixture was then concentrated in vacuo. The crude product was purified by $SiO_2$ Biotage chromatography (hexanes/acetone) to afford 4.24 g (42.6%) of methyl 1-benzyl-3-fluoropyrrolidine-3-carboxylate (72a): $^1$H NMR (400 MHz, DMSO-$d_6$) δ=7.35-7.23 (m, 5H), 3.72 (s, 3H), 3.63 (s, 2H), 2.97-2.80 (m, 3H), 2.54-2.48 (m, 1H), 2.43-2.30 (m, 1H), 2.18-2.04 (m, 1H).

step 2: To a stirred solution of 72a (2.90 g, 12.2 mmol), EtOAc (61 mL) and di-tert-butyl dicarbonate (3.20 g, 14.7 mmol) was added palladium hydroxide (1.72 g, 1.22 mmol). The flask was degassed with $N_2$ then the reaction mixture was sparged with $H_2$ gas for 5 min then stirred under an $H_2$ atmosphere at RT for 16 h under an $H_2$ filled balloon. The suspension was filtered through glass microfibre filter ("gf/f") paper and then the filtrate was washed with water (1x 60 mL) and brine (1x 60 mL), dried ($Na_2SO_4$), filtered, and concentrated in vacuo. The crude product was purified by $SiO_2$ Biotage chromatography (hexanes/EtOAc) to afford 2.90 g (96.0%) of 72b:
$^1$H NMR (400 MHz, DMSO-$d_6$) δ=3.76 (s, 3H), 3.71-3.55 (m, 3H), 3.37-3.31 (m, 1H), 2.46-2.27 (m, 2H), 1.40 (s, 9H).

step 3: To a solution of 72b (414.4 mg, 1.676 mmol) and 3:1 THF:MeOH (5.6 mL) was added 2.0 M aqueous KOH (2.1 mL, 4.19 mmol) and the solution stirred at RT for 2 h. The organic solvent was removed in vacuo and the residue diluted with 20% IPA/DCM and then acidified to pH 3 with 1.0 M HCl. This mixture was twice extracted with 20% IPA/DCM and combined extracts were twice washed with water, dried ($Na_2SO_4$), filtered, and concentrated in vacuo to afford 352.8 mg (90.3%) of 74a. $^1$H NMR (400 MHz, DMSO-$d_6$) δ=13.80 (s, 1H), 3.69-3.54 (m, 3H), 3.36-3.32 (m, 1H), 2.43-2.24 (m, 2H), 1.40 (s, 9H).

step 4: Preparation of tert-butyl 3-fluoro-3-(methoxy(methyl)carbamoyl)pyrrolidine-1-carboxylate (74b) from 74a can be accomplished in accord with the procedure in step 1 of referential example 3.

step 5: To a solution of 74b (410.2 mg, 1.49 mmol) and THF (7.4 mL) cooled to 0° C. in an oven-dried flask and degassed with $N_2$ was added 3-chloro-4-fluorophenylmagnesium bromide (3.1 mL, 1.56 mmol, 0.5 M THF solution) and the resulting solution stirred at 0° C. for 2 h. The reaction was quenched with water and concentrated in vacuo. The residue was twice extracted with EtOAc. The combined extracts were washed with water (2×) and brine (1×), dried ($Na_2SO_4$), filtered and concentrated in vacuo. The crude product was purified by $SiO_2$ Biotage chromatography eluting with a hexanes/EtOAc gradient to afford 218.4 mg (42.6%) of 76: MS m/z APCI-pos (M+1-100)=246.1, 248.1.

step 6: To a solution of 76 (218.4 mg, 0.632 mmol) and MeOH (3.2 mL) cooled to 0° C. was added $NaBH_4$ (26.29 mg, 0.695 mmol) and stirred at 0° C. for 1 h. The reaction was diluted with a small amount of water and concentrated in vacuo. The residue was diluted with EtOAc and washed twice with water (2×) then brine (1×), dried ($Na_2SO_4$), filtered and concentrated in vacuo. The crude product was purified by $SiO_2$ Biotage chromatography (hexanes/EtOAc) to afford 194.9 mg (88.7%) of tert-butyl 3-((3-chloro-4-fluorophenyl)(hydroxy)methyl)-3-fluoropyrrolidine-1-carboxylate (77): LC/MS: m/z [M+1-100] 248.1, 249.1.

step 7: To a solution of 77 (194.9 mg, 0.560 mmol) and THF (5.6 mL) cooled to 0° C. was added phthalimide (90.70 mg, 0.616 mmol) and $Ph_3P$ (191.1 mg, 0.729 mmol). The reaction mixture was then treated with DEAD (331.8 μL, 0.729 mmol) and warmed to RT and stirred for 16 h. The reaction mixture was concentrated in vacuo. The crude product was purified by $SiO_2$ Biotage chromatography eluting with hexanes/acetone to afford 238.5 mg (89.2%) of tert-butyl 3-((3-chloro-4-fluorophenyl)(1,3-dioxoisoindolin-2-yl)methyl)-3-fluoropyrrolidine-1-carboxylate (79): LC/MS: [M+1-100] m/z 377.0, 379.0.

step 8: To a stirred solution of 79 (238.5 mg, 0.500 mmol) and THF:MeOH (5.0 mL 1:1) was added hydrazine monohydrate (242.6 μL, 5.001 mmol) and the solution was heated to 60° C. for 16 h. The reaction was then cooled to RT and concentrated in vacuo. The residue was diluted with EtOAc and washed sequentially with water (1×), $NaHCO_3$ (1×), and brine (1×), dried ($Na_2SO_4$), filtered and concentrated in vacuo to afford 160.1 mg (92.3%) of tert-butyl 3-(amino(3-chloro-4-fluorophenyl)methyl)-3-fluoropyrrolidine-1-carboxylate (78).

step 9: A solution of 78 (160.1 mg, 0.462 mmol) and DMF (2.3 mL) was treated with 2-(tetrahydro-2H-pyran-4-ylamino)quinazoline-7-carboxylic acid (69f, 126.2 mg, 0.462 mmol), HATU (193.1 mg, 0.508 mmol) and DIPEA (160.8 μL, 0.923 mmol) and stirred at RT for 16 h. The reaction mixture was diluted with EtOAc and thrice washed with water, twice with $NaHCO_3$, and once with brine, dried ($Na_2SO_4$), filtered and concentrated in vacuo. The crude reaction mixture was then purified by $SiO_2$ Biotage chromatography eluting with hexanes/acetone. The isolated material was dissolved in DCM (2.0 mL) and treated with 1:1 DCM:TFA (1.0 mL) and stirred at RT for 2 h. The solution was concentrated in vacuo, diluted with $NaHCO_3$ and twice extracted with EtOAc. The combined organics were washed twice with $NaHCO_3$ and once with brine, dried ($Na_2SO_4$), filtered and concentrated in vacuo to afford 125.8 mg (54.3%) of I-16.

The enantiomers (I-36, I-37, I-38 and I-39) were resolved by chromatography on a 4.6×50 mm, 3 μm Chiralpak IC, column eluting with a mobile phase of 50% $CO_2$/50% MeOH (0.1% $Et_2NH$) at a flow rate of 5 mL/min and a 2 min runtime.

2-(Tetrahydropyran-4-ylamino)-quinazoline-7-carboxylic acid [(S)-(3-fluoro-4-trifluoromethyl-phenyl)-(S)-pyrrolidin-2-yl-methyl]-amide (I-3), 2-isopropylamino-quinazoline-7-carboxylic acid [(S)-(3-fluoro-4-trifluoromethyl-phenyl)-(R)-pyrrolidin-2-yl-methyl]-amide (I5) 2-(tetrahydropyran-4-ylamino)-quinazoline-7-carboxylic acid [(S)-(3-fluoro-4-trifluoromethyl-phenyl)-(R)-pyrrolidin-2-yl-methyl]-amide (I-7), 2-(tetrahydropyran-4-ylamino)-quinazoline-7-carboxylic acid [(R)-(3-chloro-4-fluoro-phenyl)-(R)-pyrrolidin-3-yl-methyl]-amide (I-8), 2-(tetrahydropyran-4-ylamino)-quinazoline-7-carboxylic acid [(R)-(3-chloro-4-fluoro-phenyl)-(S)-pyrrolidin-3-yl-methyl]-amide (I-9), 2-(tetrahydropyran-4-ylamino)-quinazoline-7-carboxylic acid [(S)-(3-chloro-4-fluoro-phenyl)-(S)-pyrrolidin-3-yl-methyl]-amide (I-10), 2-(tetrahydropyran-4-ylamino)-quinazoline-7-carboxylic acid [(S)-(3-chloro-4-fluoro-phenyl)-(R)-pyrrolidin-3-yl-methyl]-amide (I-11), 2-(tetrahydropyran-4-ylamino)-quinazoline-7-carboxylic acid [(S)-(4-chloro-3-fluoro-phenyl)-(R)-pyrrolidin-2-yl-methyl]-amide (I-23), 2-(tetrahydropyran-4-ylamino)-quinazoline-7-carboxylic acid [(S)-(3-fluoro-4-methoxy-phenyl)-(R)-pyrrolidin-2-yl-methyl]-amide (I-24), 2-((R)-1-cyclopropyl-ethylamino)-quinazoline-7-carboxylic acid [(S)-(3-fluoro-4-methoxy-phenyl)-(R)-pyrrolidin-2-yl-methyl]-amide (I-26), 2-(tetrahydropyran-4-ylamino)-quinazoline-7-carboxylic acid [(S)-(3-fluoro-4-methoxy-phenyl)-((2R,4S)-4-fluoro-pyrrolidin-2-yl)-methyl]-amide (I-31), 2-(tetrahydropyran-4-ylamino)-quinazoline-7-carboxylic acid [(S)-(4-chloro-3-fluoro-phenyl)-((2R,5R)-5-methyl-pyrrolidin-2-yl)-methyl]-amide (I-35) and 2-((S)-2,2,2-trifluoro-1-methyl-ethylamino)-quinazoline-7-carboxylic acid [(S)-(4-chloro-3-fluoro-phenyl)-(S)-pyrrolidin-2-yl-methyl]-amide (I-40) were prepared analogously from the appropriate 2-substitued quinazoline-2-carboxylic acid and the requisite amine.

2-(Tetrahydropyran-4-ylamino)-quinazoline-7-carboxylic acid [(S)-(3-fluoro-4-trifluoromethyl-phenyl)-((R-1-methyl-pyrrolidin-2-yl)-methyl]-amide (I-17) was prepared by reductive amination of I-5 with $NaHB(OAc)_3$ and paraformaldehyde. Reductive amination is preferably carried out carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7. Reductive amination procedures have been reviewed: R. M. Hutchings and M. K. Hutchings *Reduction of C═N to CHNH by Metal Hydrides in Comprehensive Organic Synthesis* col. 8, I. Fleming (Ed) Pergamon, Oxford 1991 pp. 47-54.

One skilled in the art will appreciate that the compounds can be either administered as racemic mixtures or resolved enantiomers. The enantiomers can be prepared by resolution of the racemates on chiral HPLC support, for example, using a Chiral Tech IC column (4.6 mm×250 mm,) eluting with 40% EtOH/hexane at a flow rate of 1 mL/min. Alternately the amines can be prepared by chiral synthesis using utilizing (R)-1-methyl-3,3-diphenylhexahydropyrrolo[1,2-c][1,3,2]oxazaborole in place of an achiral hydride reducing agent. Coupling of the chiral amines affords the pure enantiomers directly. It also should be apparent when a chiral proline derivative is the starting material. The amine resulting from reduction with a chiral hydride is a pair of diastereomers which can be separated using standard $SiO_2$ or reverse phase chromatography.

EXAMPLE 3

5-fluoro-2-(tetrahydropyran-4-ylamino)-quinazoline-7-carboxylic acid [(S)-(3-fluoro-4-methoxy-phenyl)-(R)-pyrrolidin-2-yl-methyl]-amide (I-25)

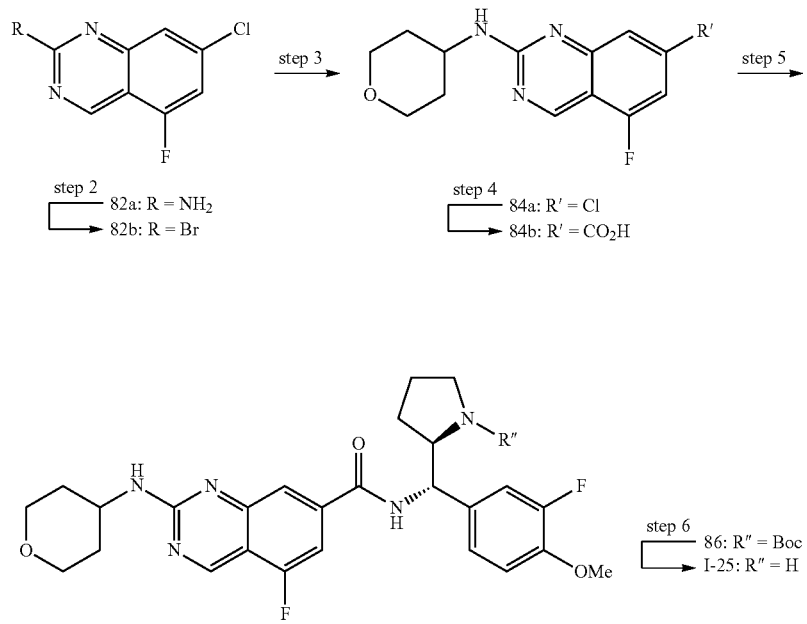

step 2
82a: R = NH$_2$
82b: R = Br step 4
84a: R' = Cl
84b: R' = CO$_2$H step 6
86: R'' = Boc
I-25: R'' = H step 1: To a stirred suspension of 4-chloro-2,6-difluorobenzaldehyde (45 g, 255 mmol) in DMA (360 mL), at room temperature under nitrogen was added guanidine bis(carbonate) (70.0 g, 382 mmol). The mixture was heated to 140° C. for 3 hours. The reaction was then cooled to room temperature followed by addition of 400 mL water with stirring. The mixture was then filtered. The solids were then collected and triturated in 200 mL methanol for 10 minutes, then filtered. These solids were then dried in vacuo to obtain 31.6 g (63%) of 7-chloro-5-fluoroquinazolin-2-amine (82a) as a brown solid.

step 2: To a stirred solution of 82a (20 g, 101 mmol) in dibromomethane (1012 mL, 101 mmol) at RT under N$_2$ was added tribromostibine (73.2 g, 202 mmol) and the resulting solution stirred for 10 min. tert-Butyl nitrite (48.2 mL, 405 mmol) was added and the reaction was immediately placed in 50° C. water bath and stirred for 13 h. The reaction was cooled to RT and the resulting precipitate was filtered and discarded. The filtrate was partitioned between DCM (2 L) and H$_2$O (2 L). The biphasic mixture was filtered and the precipitate discarded. The organic layer was separated and loaded directly on a 1 kg SiO$_2$ plug and eluted with DCM. The combined fractions containing product were concentrated in vacuo to a afford 13.4 g (51%) of 82b as a light yellow solid.

step 3: To a stirred solution of tetrahydro-2H-pyran-4-amine (14.8 g, 146 mmol) and TEA (10.2 mL, 73.0 mmol) in IPA (150 mL) at RT in a capped high pressure reaction vessel was added 82b (13.4 g, 48.7 mmol). The reaction was sealed under nitrogen and heated to 85° C. and stirred 2 h. After cooling to RT the precipitate was filtered and washed with IPA (150 mL). These precipitates were then dried in vacuo to afford 14.7 g (100%) of 84a as a tan solid.

step 4: A stirred suspension of 84a (206 mg, 0.695 mmol), potassium 2-ethoxy-2-oxoacetate (163 mg, 1.04 mmol), Pd(TFA)$_2$ (6.93 mg, 0.0208 mmol), 1,3-bis(dicyclohexylphosphino)propane bis-(tetrafluoroborate (25.5 mg, 0.0417 mmol) in NMP (2.3 mL) under nitrogen was heated on an oil bath at 150° C. for 18 h. The reaction was then cooled to 50° C. and sodium hydroxide (1042 µL, 2.08 mmol) was added and the mixture was stirred for 1 h. The reaction was cooled to RT and the reaction solution was loaded to a 50 g Biotage C18 reverse phase column and eluted with a H$_2$O/MeOH gradient (0 to 100% MeOH). The fractions containing product were combined and 1 N HCl (2 mL) was added and stirred for 2 min. The solution was concentrated in vacuo and the residue azeotroped with EtOH (100 mL) to afford 175 mg (72%) of 84b containing 1 mole equivalent NaCl as a brown solid.

step 5: To a stirred suspension of 84b (30 mg, 0.086 mmol) in DCM (1 mL) under nitrogen at RT was added CDI (17 mg, 0.10 mmol). After stirring for 1 h, (R)-tert-butyl 2-((S)-amino (3-fluoro-4-methoxyphenyl)methyl)pyrrolidine-1-carboxylate (47c) (42 mg, 0.13 mmol) was added and stirred overnight. This solution was added directly to a SiO$_2$ column and eluted with a DCM/EtOAc gradient (0 to 100% MeOH) to afford 24 mg (47%) of 86 as a yellow solid.

step 6: To a solution of 86 (24 mg, 0.040 mmol) and DCM (0.3 mL) was added 4M HCl/dioxane (301 µL, 1.2 mmol). The reaction mixture was stirred for 1 h, then concentrated in vacuo. The crude product was dissolved in DCM (2 mL) and washed with satd. aq. NaHCO$_3$ (1 mL) The organic phase was isolated, dried (Na$_2$SO$_4$), filtered and concentrated in vacuo to afford 20 mg (100%) of I-25.

5-Fluoro-2-(2-methoxy-ethylamino)-quinazoline-7-carboxylic acid (87a), 5-fluoro-2-(3-fluoro-propylamino)-quinazoline-7-carboxylic acid (87b), 2-(cyclopropylmethyl-amino)-5-fluoro-quinazoline-7-carboxylic acid (87c), (R)-5-fluoro-2-(tetrahydrofuran-3-ylamino)quinazoline-7-carboxylic acid (87d), (S)-5-fluoro-2-(tetrahydrofuran-3-ylamino)quinazoline-7-carboxylic acid (87e), 5-fluoro-2-[(oxetan-3-ylmethyl)-amino]-quinazoline-7-carboxylic acid (87f) and 5-fluoro-2-(3-methyl-oxetan-3-ylamino)-quinazoline-7-carboxylic acid (87 g) were prepared analogously, except in step 3, tetrahydro-2H-pyran-4-amine was replaced with 2-methoxy-ethylamine, 3-fluoro-propylamine, cyclopropylmethyl-amino, (S)-(tetrahydro-furan-3-yl)amine, (R)-(tetrahydro-furan-3-yl)amine, oxetan-3-ylmethanamine and 3-methyl-oxetan-3-ylamine respectively.

EXAMPLE 4

(S)-N-((4-chloro-3-fluorophenyl)(1-methyl-1H-pyrazol-3-yl)methyl)-5-fluoro-2-(tetrahydro-2H-pyran-4-ylamino)quinazoline-7-carboxamide (I-22)

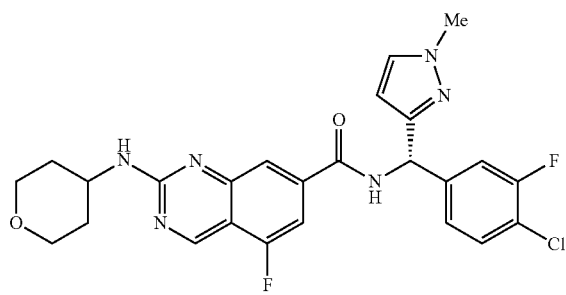 [SMILES: Cn1ccc([C@@H](NC(=O)c2cc(F)c3cnc(NC4CCOCC4)nc3c2)c2ccc(Cl)c(F)c2)n1]

A solution of 84b (50 mg, 0.17 mmol), HBTU (72 mg, 0.19 mmol), DIPEA (90 μL, 0.51 mmol), (S)-(4-chloro-3-fluorophenyl)(1-methyl-1H-pyrazol-3-yl)methanamine (32b) (45 mg, 0.19 mmol) and DMF (1.5 mL) at RT under nitrogen was stirred for 4 h. The mixture was then poured into $H_2O$ (2 mL), and extracted with DCM (5 mL). The organic fraction was dried ($MgSO_4$), filtered and concentrated in vacuo. The crude product was purified by $SiO_2$ chromatography eluting with EtOAc to afford 51 mg (58%) of I-22.

(S)-5-Fluoro-N-((3-fluoro-4-methoxyphenyl)(2-methyl-2H-1,2,3-triazol-4-yl)methyl)-2-(tetrahydro-2H-pyran-4-ylamino)quinazoline-7-carboxamide (I-51) was prepared analogously except 32b was replaced with 34c, and 5-fluoro-N-((S)-(3-fluoro-4-methoxyphenyl)(1-methyl-1H-pyrazol-4-yl)methyl)-2-((3S,4S)-3-fluorotetrahydro-2H-pyran-4-ylamino)quinazoline-7-carboxamide (I-52) was prepared analogously except 84b was replaced with 5-fluoro-2-((3S,4S)-3-fluorotetrahydro-2H-pyran-4-ylamino)quinazoline-7-carboxamide which can be prepared in accord with the procedure in example 3 except in step 3, 2H-pyran-4-amine was replaced with 60c.

5-Fluoro-2-(tetrahydro-pyran-4-ylamino)-quinazoline-7-carboxylic acid [(3-fluoro-4-methoxy-phenyl)-(2-methyl-2H-[1,2,3]triazol-4-yl)-methyl]-amide (I-53) was prepared analogously except 32b was replaced with 34c.

5-Fluoro-2-(tetrahydro-pyran-4-ylamino)-quinazoline-7-carboxylic acid [(R)-(3-fluoro-4-methoxy-phenyl)-(2-methyl-2H-[1,2,3]triazol-4-yl)-methyl]-amide (I-54) was prepared analogously except 32b was replaced with (R)-34c.

5-Fluoro-2-(tetrahydro-pyran-4-ylamino)-quinazoline-7-carboxylic acid [(S)-(3-chloro-4-cyano-phenyl)-(1-methyl-1H-pyrazol-4-yl)-methyl]-amide (I-65) was prepared analogously except 32b was replaced with (S)-40i.

5-Fluoro-2-(tetrahydro-pyran-4-ylamino)-quinazoline-7-carboxylic acid [(S)-(3-chloro-4-methoxy-phenyl)-(1-methyl-1H-pyrazol-4-yl)-methyl]-amide (I-66) was prepared analogously except 32b was replaced with (S)-40f.

5-Fluoro-2-(2-methoxy-ethylamino)-quinazoline-7-carboxylic acid [(S)-(3-fluoro-4-methoxy-phenyl)-(1-methyl-1H-pyrazol-4-yl)-methyl]-amide (I-58) was prepared analogously except 32b was replaced with 40f and 84b was replaced with 87a.

5-Fluoro-2-(3-fluoro-propylamino)-quinazoline-7-carboxylic acid [(S)-(3-fluoro-4-methoxy-phenyl)-(1-methyl-1H-pyrazol-4-yl)-methyl]-amide (I-59) was prepared analogously except 32b was replaced with 40f and 84b was replaced with 87b.

2-(Cyclopropylmethyl-amino)-5-fluoro-quinazoline-7-carboxylic acid [(S)-(3-fluoro-4-methoxy-phenyl)-(1-methyl-1H-pyrazol-4-yl)-methyl]-amide (I-60) was prepared analogously except 32b was replaced with 40f and 84b was replaced with 87c.

5-Fluoro-N-((S)-(3-fluoro-4-methoxyphenyl)(1-methyl-1H-pyrazol-4-yl)methyl)-2-((R)-tetrahydrofuran-3-ylamino)quinazoline-7-carboxamide (I-61) was prepared analogously except 32b was replaced with 40f and 84b was replaced with 87d.

5-Fluoro-N-((S)-(3-fluoro-4-methoxyphenyl)(1-methyl-1H-pyrazol-4-yl)methyl)-2-((R)-tetrahydrofuran-3-ylamino)quinazoline-7-carboxamide (I-62) was prepared analogously except 32b was replaced with 40f and 84b was replaced with 87e.

5-Fluoro-2-[(oxetan-3-ylmethyl)-amino]-quinazoline-7-carboxylic acid [(S)-(3-fluoro-4-methoxy-phenyl)-(1-methyl-1H-pyrazol-4-yl)-methyl]-amide (I-63) was prepared analogously except 32b was replaced with 40f and 84b was replaced with 87f.

5-Fluoro-2-(3-methyl-oxetan-3-ylamino)-quinazoline-7-carboxylic acid [(S)-(3-fluoro-4-methoxy-phenyl)-(1-methyl-1H-pyrazol-4-yl)-methyl]-amide (I-64) was prepared analogously except 32b was replaced with 40f and 84b was replaced with 87 g.

EXAMPLE 5

5-fluoro-2-(tetrahydropyran-4-ylamino)-quinazoline-7-carboxylic acid [(S)-(3-fluoro-4-methoxy-phenyl)-(1-methyl-1H-pyrazol-4-yl)-methyl]-amide (I-33)

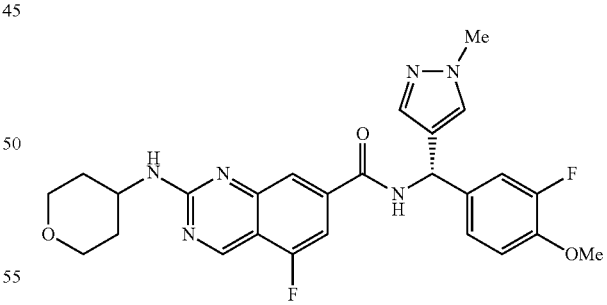

A solution of 84b (62 g, 21 mmol), HBTU (8.9 g, 23 mmol), DIPEA (11 mL, 64 mmol), (S)-(3-fluoro-4-methoxyphenyl)(1-methyl-1H-pyrazol-4-yl)methanamine (40l) (5.8 g, 21 mmol) and DMF (60 mL) at RT under nitrogen was stirred for 5 h. The mixture was then poured into $H_2O$ (120 mL) and extracted with EtOAc (5×120 mL). The organic fractions were combined and dried ($MgSO_4$), filtered and concentrated in vacuo. The crude product was triturated with DCM followed by trituration with EtOAc to give 6.5 g (60%) of I-33 as a yellow solid.

EXAMPLE 6

N-((S)-(4-chloro-3-fluorophenyl)(1-methyl-1H-pyrazol-4-yl)methyl)-2-((2S,4R)-2-(hydroxymethyl)tetrahydro-2H-pyran-4-ylamino)quinazoline-7-carboxamide (I-47)

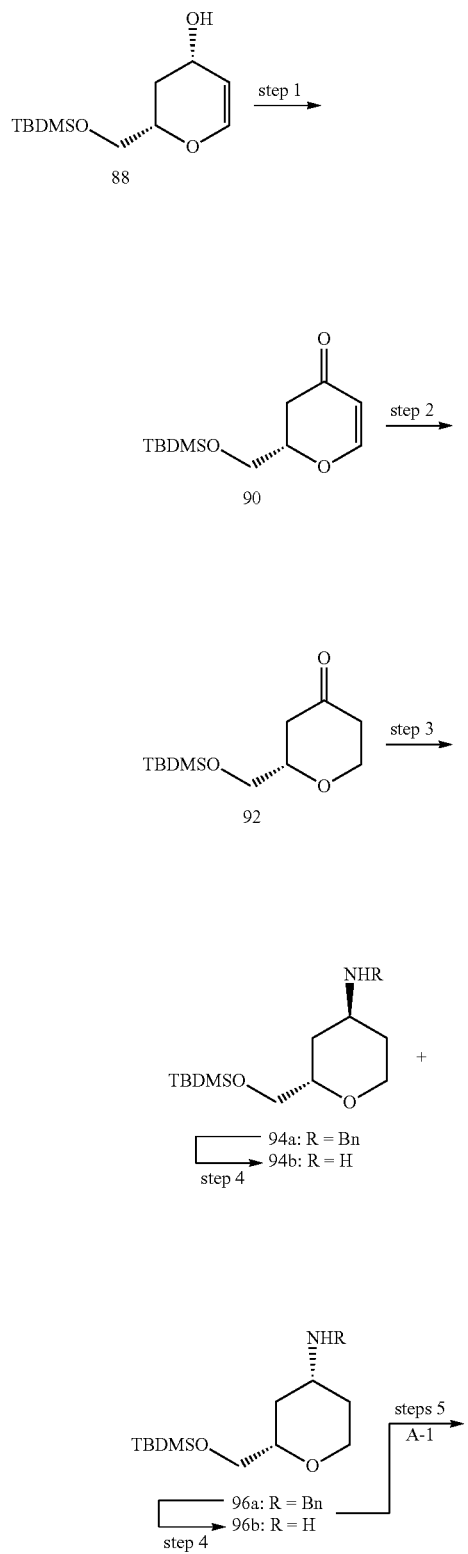

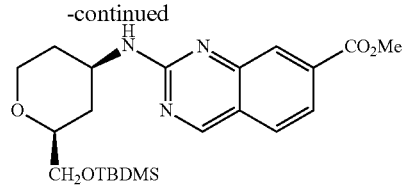

steps 6-9 ↓ step 1: To a solution of (2S,4S)-2-((tert-butyldimethylsilyloxy)methyl)-3,4-dihydro-2H-pyran-4-ol (88, 3.565 g, 14.59 mmol) (prepared from (2R,3S,4R)-2-(hydroxymethyl)-3,4-dihydro-2H-pyran-3,4-diol according to the procedures in L. A. Paquette and J. A. Oplinger, *J. Org. Chem*. 1988 53:2953-2959) and DCM (25 mL) was added 4 Å molecular sieves (7 g) followed by N-methyl morpholine N-oxide (3.418 g, 29.17 mmol) and tetrapropylammonium perruthenate (0.2563 g, 0.7293 mmol). The reaction was stirred for 1.5 h at RT. The mixture was passed through a plug of $SiO_2$ and eluted with DCM. The filtrate was concentrated and the resulting residue was purified by $SiO_2$ chromatography eluting with 25% EtOAc/hexane to afford 3.097 g (87.6%) of 90.

step 2: A suspension of 90 (3.097 g, 12.78 mmol), Pd/C (0.5439 g, 0.2555 mmol) and EtOAc (30 mL) and was stirred and maintained under hydrogen balloon pressure for 18 h. The reaction was filtered through a plug of Celite® and concentrated. The resulting residue was purified by $SiO_2$ chromatography eluting with 20% EtOAc/hexane to afford 2.035 g (65.17%) of 92.

step 3: To a solution of 92 (1.885 g, 7.713 mmol), phenylmethanamine (0.9470 mL, 8.484 mmol) and DCE (40 mL) was added $NaBH(OAc)_3$ (2.288 g, 10.80 mmol) and the reaction stirred for 1 h. The reaction mixture was poured into water and extracted with DCM. The combined organic extracts were washed with $NaHCO_3$, dried ($MgSO_4$), filtered and concentrated. The resulting residue was purified by $SiO_2$ eluting with a DCM/MeOH gradient (0 to 3% MeOH) to afford (2S,4R)—N-benzyl-2-((tert-butyldimethylsilyloxy)methyl)tetrahydro-2H-pyran-4-amine (96a, 1.686 g, 65.15% yield) and the trans (2S,4S)—N-benzyl-2-((tert-butyldimethylsilyloxy)methyl)tetrahydro-2H-pyran-4-amine (94a, 1.04 g, 40.18% yield).

step 4: To a solution of 94a (1.04 g, 3.10 mmol) and EtOH (20 mL) was added Pd/C (0.660 g, 0.310 mmol) and the reaction was stirred and maintained under balloon hydrogen pressure for 18 h. The mixture was filtered through a zap cap membrane filter. The filtrate was concentrated to afford 664 mg (87.3%) of 94b which was used without further purification.

The conversion of 96a to (2S,4R)-2-((tert-butyldimethylsilyloxy)methyl)tetrahydro-2H-pyran-4-amine (96b) was carried out analogously.

step 5: Condensation of 96b and A-1 can be carried out in accord with the procedure described in step 1 of example 1 to afford 98. Hydrolysis of the methyl ester (step 6), removal of the silyl-protecting group (step 7) can be carried out as described in steps 2 and 3 of example 1. Condensation of 2-((2S,4R)-2-(hydroxymethyl)tetrahydro-2H-pyran-4-ylamino)quinazoline-7-carboxylic acid and (S)-(4-chloro-3-fluorophenyl)(1-methyl-1H-pyrazol-4-yl)methanamine (100) can be carried out in accord with the procedure in step 4 of example 1 to afford I-47.

2-((2S,4R)-2-Hydroxymethyl-tetrahydro-pyran-4-ylamino)-quinazoline-7-carboxylic acid [(S)-(3-fluoro-4-methoxy-phenyl)-(1-methyl-1H-pyrazol-4-yl)-methyl]-amide (I-43) was prepared analogously except 100 was replaced with (S)-(4-methoxy-3-fluorophenyl)(1-methyl-1H-pyrazol-4-yl)methanamine.

2-((2S,4S)-2-hydroxymethyl-tetrahydro-pyran-4-ylamino)-quinazoline-7-carboxylic acid [(S)-(4-chloro-3-fluoro-phenyl)-(1-methyl-1H-pyrazol-4-yl)-methyl]-amide (I-42) and N-((S)-(3-fluoro-4-methoxyphenyl)(1-methyl-1H-pyrazol-4-yl)methyl)-2-((2S,4S)-2-(hydroxymethyl)tetrahydro-2H-pyran-4-ylamino)quinazoline-7-carboxamide (I-46) were prepared analogously except 96b was replaced with 94b and for the case of (I-46), 100 was replaced with (S)-40e.

Acetic acid (2S,4S)-4-(7-{[(S)-(3-fluoro-4-methoxy-phenyl)-(1-methyl-1H-pyrazol-4-yl)-methyl]-carbamoyl}-quinazolin-2-ylamino)-tetrahydro-pyran-2-ylmethyl ester (I-57) cam be prepared be acetylation of I-46.

EXAMPLE 7

N-((3-fluoro-4-methoxyphenyl) (1-(2-hydroxyethyl)-1H-pyrazol-4-yl) methyl)-2-(tetrahydro-2H-pyran-4-ylamino) quinazoline-7-carboxamide (I-67)

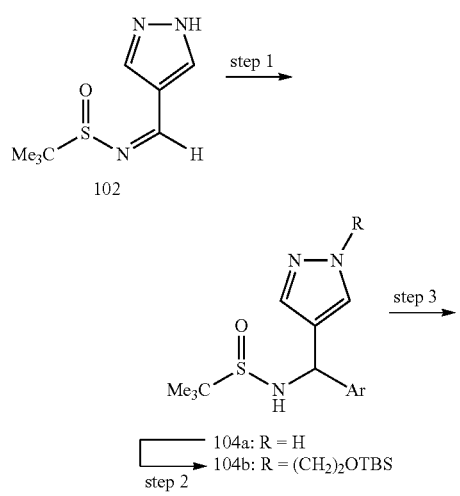

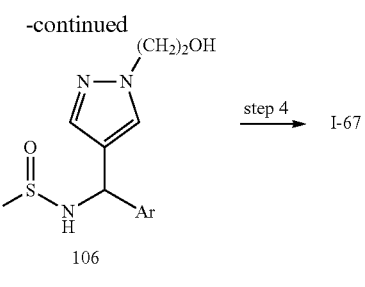

Ar = 3-fluoro-4-methoxy-phenyl step 1: To a solution of 102 (500 mg, 2.50 mmol) in THF (20 mL) was added (3-fluoro-4-methoxyphenyl)magnesium bromide (10 mL, 25 mmol) at −78° C. The resultant mixture was warmed to RT and stirred for 2 h. The reaction mixture was treated with $NH_4Cl$ (5 mL) and thrice extracted with EtOAc (50 mL). The combined organic extracts were washed with brine (10 mL), dried ($Na_2SO_4$), filtered and concentrated. The residue was purified by $SiO_2$ chromatography eluting with EtOAc/petroleum ether (1:2) to afford 600 mg (74%) of 104a: LC-MS (ESI) m/z: 326 (M+H).

step 2: To the solution of 104a (350 mg, 1.08 mmol) in DMF (3.0 mL) cooled to 0° C. was added NaH (47.0 mg, 1.18 mmol). After stirring for 10 min, (2-bromoethoxy)(tert-butyl)dimethylsilane (513 mg, 2.15 mmol) was added. The reaction mixture was warmed to RT and stirred for another 1.5 h. The reaction was quenched with water (1.0 mL) and extracted with EtOAc (3 10 mL). The combined organic extracts were washed with brine (5 mL), dried ($Na_2SO_4$), filtered and concentrated in vacuo. The residue was purified by $SiO_2$ chromatography eluting with EtOAc/petroleum ether (1:10) to afford 400 mg (77%) of 104b as a white solid: LC-MS (ESI) m/z: 484 (M+H).

step 3: A solution of 104b (400 mg, 0.830 mmol) in ca. 0.2 N HCl in EtOAc (20 mL) and MeOH (1.0 mL) was stirred at RT for 2 h. The solid 106 (178 mg, 71% yield) was collected by filtration and was used without further purification: LC-MS (ESI) m/z: 266 (M+H).

step 4: A mixture of 106 (64 mg, 0.22 mmol), 69f (40 mg, 0.15 mmol), and HATU (89 mg, 0.23 mmol) in DMF (4.0 mL) and TEA (1.0 mL) was stirred at RT for 3 h. The mixture was diluted with EtOAc (100 mL), washed with water (3 10 mL), dried ($Na_2SO_4$), filtered and concentrated. The residue was purified by Prep-HPLC to give the 13 mg (17%) of I-67 as a yellow solid.

EXAMPLE 8

2-(Cyclopropylmethyl-amino)-5-fluoro-quinazoline-7-carboxylic acid [(S)-(3-fluoro-4-methoxy-phenyl)-(1-methyl-1H-pyrazol-4-yl)-methyl]-amide (I-60)

step 6 (SCHEME B): A 20 L 4-necked round-bottom flask was purged and maintained with a nitrogen atmosphere then charged with 4-bromo-2,6-difluorobenzaldehyde (730 g, 3.30 mol, 1.00 equiv), DMA (8 L), followed by the addition of guanidinium carbonate (476 g, 2.64 mol, 0.80 equiv). The resulting solution was stirred at 140° C. for 4 h, cooled to 30° C. and diluted with 5 L of water/ice with stirring for 30 min. The resulting solids were collected by filtration, washed with 2×3 L of water, and stirred in MeOH (3 L) for 30 min. The solids were collected by filtration and dried in a vacuum oven to afford 660 g (83%) of 7-bromo-5-fluoroquinazolin-2- amine as a yellow solid: $^1$H NMR (400 MHz, DMSO) δ 9.23 (s, 1H), 7.45 (s, 1H), 7.27 (s, 2H), 7.26 (d, J=10 Hz, 1H). LCMS: MH+242.1, 244.1 step 7: 7-Bromo-5-fluoro-quinazolin-2-amine (8.02 g, 33.1 mmol, 1.00 equiv), Pd(OAc)$_2$ (750 mg, 3.34 mmol, 0.10 equiv), 1,3-bis(dicyclohexylphosphino)propane bis(tetrafluoroborate) (2.04 g, 3.22 mmol, 0.10 equiv) and K$_2$CO$_3$ (9.27 g, 66.4 mmol, 2.00 equiv) were suspended together in DMF (100 ml) under nitrogen and treated with anhydrous MeOH (13.5 mL, 333 mmol, 10 equiv). The flask was thoroughly flushed with carbon monoxide, and then heated to 100° C. with a continuous flow of carbon monoxide, which was switched to a static positive pressure on reaching temperature. After 6 h the reaction was cooled. The mixture was diluted with water (200 mL) and extracted twice into EtOAc. The combined organic phases were washed with water and brine, dried (Na$_2$SO$_4$), filtered and concentrated in vacuo to afford a crude orange solid (6.76 g) which was absorbed onto SiO$_2$ and purified by automated SiO$_2$ chromatography eluting with an EtOAc/heptane gradient (0 to 100% EtOAc) to afford 4.30 g (59%) of methyl 2-amino-5-fluoroquinazoline-7-carboxylate as a pale orange solid: $^1$H NMR (400 MHz, CDCl3) δ 9.35 (s, 1H), 8.07 (s, 1H), 7.48 (dd, J=10.0, 1.0 Hz, 1H), 5.35 (br s, 2H), 3.98 (s, 3H); LCMS: MH+222.2 step 8: A suspension of methyl 2-amino-5-fluoro-quinazoline-7-carboxylate (4.28 g, 19.3 mmol, 1.00 equiv), CuI (1.81 g, 9.5 mmol, 0.49 equiv) and diiodomethane (7.80 mL, 96.8 mmol, 5.0 equiv) in THF (80 ml) was treated with isoamyl nitrite (7.80 mL, 58.1 mmol, 3.00 equiv) at ambient temperature, and the mixture heated to 60 ° C. After 18 h the reaction was cooled. The mixture was diluted with EtOAc (100 mL), filtered through a Celite® pad, and the dark green filtrate concentrated in vacuo to an oily residue (23.0 g) which was absorbed onto SiO$_2$ and purified by flash chromatography eluting with an EtOAc/heptane gradient (0 to 30% EtOAc) to afford 3.54 g (55%) of methyl 5-fluoro-2-iodoquinazoline-7-carboxylate as a cream-white solid: $^1$H NMR (400 MHz, CDCl3) δ 9.39 (s, 1H), 8.49 (s, 1H), 7.90 (d, J=9.5 Hz, 1H), 4.02 (s, 3H); LCMS: MH+333.0 step 9: A mixture of methyl 5-fluoro-2-iodo-quinazoline-7-carboxylate (50 mg, 0.15 mmol, 1.0 equiv), cyclopropylmethylamine hydrochloride (32 mg, 0.30 mmol) and DIPEA (0.105 mL, 0.60 mmol) in DMF (0.5 mL) was stirred at 75 ° C. for 1 h. The cooled mixture was diluted with EtOAc (30 mL) and washed with water (30 mL). The organic extract was dried (Na$_2$SO$_4$), filtered and concentrated in vacuo to afford a yellow solid that was used without further purification.

step 10: A solution of methyl 2-(cyclopropylmethylamino)-5-fluoro-quinazoline-7-carboxylate (40 mg, 0.15 mmol) in THF (1.3 mL) and water (0.4 mL) was treated with LiOH (10.4 mg, 0.44 mmol) and stirred at ambient temperature for 1 h. The mixture was acidified with 1M aqueous citric acid and the resulting precipitate collected via centrifugation, washed with water, and then dried under high vacuum to afford 2-(cyclopropylmethylamino)-5-fluoroquinazoline-7-carboxylic acid as a yellow solid which was used without further purification.

The condensation of 2-(cyclopropylmethylamino)-5-fluoroquinazoline-7-carboxylic acid and (S)-(3-fluoro-4-methoxyphenyl)(1-methyl-1H-pyrazol-4-yl)methanamine (401) to afford I-60 was carried out in accord with the procedure in Example 5.

EXAMPLE 9

ERK-2 Enzymatic Assay

Compounds were tested in an enzymatic assay using human ERK-2 (Mitogen Activated Kinase 1), recombinantly expressed as an N-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in DMSO in 3-fold serial dilutions at 100× final concentrations. In addition to compound, the assay contained 50 mM HEPES [pH 7.3], 10 mM MgCl$_2$, 1 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and IC$_{50}$ values were determined using a four-parameter fit. Representative data is in TABLE I and TABLE II. The reported IC$_{50}$ may be from a single assay or the mean of multiple assays.

EXAMPLE 10

Cell Proliferation/Viability Assay

Viable cells after a 3-day (72-hour) incubation with ERK compounds were quantified using the Cell Titer-Blue Cell Viability Assay from Promega.

Materials and Methods: HCT116 cells were plated in 96 well micro-plates at a density of 1,000 cells/well. The cells were allowed to attach to micro-plate overnight at 37° C./5% CO$_2$. After overnight attachment, diluted compounds were then added to the cells at a final concentration of 0.5% DMSO. After 3 days (72 hours) at 37° C./5% CO$_2$, the number of viable cells was determined using the Cell Titer-Blue Cell Viability Assay from Promega. Briefly, Cell Titer-Blue reagent were added to the cells and incubated for 1 hour. Fluorescence (560 nm$_{excitation}$/590 nm$_{emission}$) was then read using a fluorescence micro-plate reader. Background from high concentration Erk-inhibited wells was subtracted. Representative data is in TABLE III (infra). The reported IC$_{50}$ may be from a single assay or the mean of multiple assays.

EXAMPLE 11

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 h and quantifying fluorescent pP90RSK (Ser380) signal on fixed cells and normalizing to GAPDH signal.

Materials and Methods: HepG2 cells were obtained from ATCC and grown in DMEM supplemented with 10% fetal bovine serum. Cells were plated in 96-well plates at 35,000 cells/well and allowed to attach overnight at 37° C./5% CO$_2$. Diluted compounds were then added at a final concentration of 0.5% DMSO. After 1.5 h compound incubation, cells were stimulated with the addition of PMA (phorbol 12-myristate 13-acetate) at a final concentration of 100 ng/mL; the PMA stimulation was a 30-min incubation at 37° C./5% CO$_2$. After the 30-minute PMA stimulation, cells were washed with PBS and fixed in 3.7% formaldehyde in PBS at room temperature for 15-20 min. This was followed by another wash in PBS and then permeabilization in 100% MeOH at room temperature for 10-15 min. Following the permeabilization incubation, cells were washed in PBS/0.05% Tween-20, followed by a block in Odyssey blocking buffer (LI-COR Biosciences) for at least 1 hour. Antibodies to phosphorylated P90RSK (Ser380) (Cell Signaling #9335, rabbit monoclonal) and GAPDH (Fitzgerald 10R-G109a, mouse monoclonal) were added to the cells and incubated overnight at 4° C. pP90RSK (Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 h. Both secondary antibodies were used at a 1:1000 dilution. Cells were then washed and analyzed for fluorescence at both wavelengths using the Odyssey Infrared Imaging System (LI-COR Biosciences). Phosphorylated P90RSK(Ser380) signal was normalized to GAPDH signal. Representative data is in TABLE III (infra). The reported $IC_{50}$ may be from a single assay or the mean of multiple assays.

TABLE III

| Cpd. No. | Cell Proliferation/Viability Assay [1] $IC_{50}$ (µM) | Cellular P90RSK(Ser380) Phosphorylation Assay [2] $IC_{50}$ (µM) |
| --- | --- | --- |
| I-1 | 2.4 | 0.0755 |
| I-2 | 0.851 | 0.0227 |
| I-3 | 0.272 | 0.046 |
| I-5 | 0.298 | 0.0117 |
| I-14 | 0.875 | 0.0598 |
| I-22 | 0.274 | 0.0235 |
| I-28 | 2.1 | 0.0874 |
| I-34 | 5.0 | 0.0791 |
| I-35 | 0.044 | 0.0053 |
| I-39 | 0.010 | 0.0174 |
| I-40 | N/A | 2.9 |
| I-41 | N/A | 0.115 |
| I-47 | N/A | 0.029 |
| I-60 | N/A | 0.334 |
| I-61 | N/A | 0.066 |
| I-64 | N/A | 0.978 |
| I-67 | N/A | 0.165 |
| II-5 | | 0.0505 |
| II-13 | | 0.0844 |
| II-18 | | 0.364 |
| II-25 | | 0.0199 |
| II-38 | | 0.038 |

[1] Example 10
[2] Example 11

EXAMPLE 12

Pharmaceutical compositions of the subject Compounds for administration via several routes can be prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |

-continued

| Ingredients | grams |
| --- | --- |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I

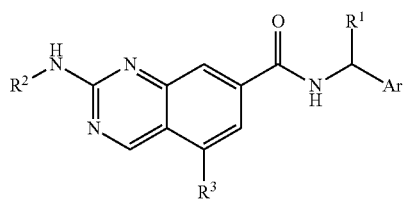

I wherein:
$R^1$ is heterocyclyl or heteroaryl optionally substituted with one to three substituents independently selected from the group consisting of $C_{1-6}$ alkyl, $C_{1-6}$ hydroxyalkyl, halogen, hydroxy and oxo;
Ar is phenyl or pyridinyl optionally substituted by 1 to 5 groups independently selected from the group consisting of $C_{1-6}$ alkyl, $C_{1-6}$ haloalkyl, $C_{1-6}$ alkoxy, $C_{3-6}$ cycloalkyl, halogen, $C_{1-6}$ haloalkoxy, $C_{1-6}$ alkylthio, $C_{1-6}$ acylamino, cyano and nitro;
$R^2$ is selected from the group consisting of (a) $C_{1-10}$ alkyl, (b) $C_{1-6}$ haloalkyl, (c) heterocyclyl or heterocyclyl-$C_{1-6}$ alkyl wherein said heterocyclyl or heterocyclyl-$C_{1-6}$ alkyl is selected from the group consisting of tetrahydropyranyl, tetrahydrofuranyl, 2-oxabicyclo[2.2.1]heptan-5-yl, oxetanyl, piperidinyl, N—$C_{1-6}$ alkyl-piperidinyl, 1,1-dioxothietan-3-yl, thietan-3-yl, and N—$C_{1-6}$ alkyl-2-oxo-pyrrolidinyl and wherein said heterocyclyl or heterocyclyl-$C_{1-6}$ alkyl is optionally substituted by 1 to 3 groups independently selected from the group consisting of $C_{1-6}$ alkyl, $C_{1-6}$ haloalkyl, $C_{1-4}$ acyloxy-$C_{1-2}$ alkyl, halogen, hydroxy, phenyl, $C_{1-3}$ hydroxyalkyl and oxo, (d) $C_{3-7}$ cycloalkyl or $C_{3-7}$ cycloalkyl-$C_{1-6}$ alkyl wherein said cycloalkyl or $C_{3-7}$ cycloalkyl-$C_{1-6}$ alkyl are optionally substituted by one to three hydroxy, $C_{1-3}$ alkoxy or halo groups, (e) $C_{1-6}$ heteroalkyl wherein the heteroalkyl moiety at least includes $C_{1-6}$ hydroxyalkyl or $C_{1-3}$ alkoxy-$C_{1-6}$ alkoxy, (f) heteroaryl wherein said heteroaryl is selected from the group consisting of pyrazolyl and pyridinyl wherein said heteroaryl is optionally independently substituted with one to three groups selected from the group consisting of $C_{1-6}$ alkyl groups, $C_{1-6}$ haloalkyl and halogen, and (g) $C_{1-3}$ cyanoalkyl;
$R^3$ is hydrogen or halogen; or,
a stereoisomer, tautomer or pharmaceutically acceptable salt thereof.

2. The compound of claim 1 wherein $R^1$ is an optionally substituted heteroaryl selected from the group consisting of pyrazolyl, triazolyl, oxadiazolyl, oxazolyl, imidazolyl and isoxazolyl.

3. The compound of claim 2 wherein $R^1$ is optionally substituted 1H-pyrazol-3-yl or 1H-pyrazol-4-yl.

4. The compound of claim 3 wherein $R^1$ is 1-methyl-1H-pyrazol-3-yl, 1-methyl-1H-pyrazol-4-yl, 1-ethyl-1H-pyrazol-3-yl or 1-(2-hydroxyethyl)-1H-pyrazol-4-yl.

5. The compound of claim 1 wherein $R^1$ is an optionally substituted pyrrolidinyl, piperidinyl or morpholinyl.

6. The compound of claim 1 wherein $R^1$ is pyrrolidin-2-yl or pyrrolidin-3-yl.

7. The compound of claim 1 wherein $R^1$ is 1-methyl-pyrrolidin-2-yl, 1-methyl-pyrrolidin-3-yl, 3-fluoro-pyrrolidin-3-yl, 4-fluoro-pyrrolidin-2-yl or 5-methyl-pyrrolidin-2-yl.

8. The compound of claim 1 wherein $R^2$ is selected from (a) tetrahydropyranyl, (b) tetrahydrofuranyl, (c) oxetanyl, wherein said tetrahydropyranyl, tetrahydrofuranyl and oxetanyl are optionally substituted with one to three groups independently selected from the group consisting of $C_{1-6}$ alkyl, $C_{1-6}$ haloalkyl, $C_{1-3}$ hydroxyalkyl, $C_{1-4}$ acyloxy-$C_{1-2}$ alkyl, and halogen, (d) 2-hydroxy-1-methyl-ethan-1-yl, (e) 2,2,2-trifluoro-1-methyl-ethan-1-yl, (f) 1-cyclopropyl-ethan-1-yl, (g) 2-methoxyethyl, (h) 3-fluoropropyl, (i) cyclopropylmethyl, (j) oxetanylmethyl, (k) 4-hydroxycyclohexyl and (l) pyrazolyl wherein said pyrazolyl moiety is optionally substituted with one to three groups independently selected from $C_{1-6}$ alkyl, $C_{1-6}$ haloalkyl and halogen.

9. The compound of claim 8 wherein $R^2$ is tetrahydropyran-4-yl, 3-fluoro-tetrahydropyran-4-yl or 2-hydroxymethyl-tetrahydropyran-4-yl.

10. The compound of claim 8 wherein $R^2$ is 2-methylpyrazol-3-yl, 2,5-dimethylpyrazol-3-yl or 1,3-dimethylpyrazol-4-yl.

11. The compound of claim 1 wherein $R^1$ is selected from the group consisting of 1-methyl-1H-pyrazol-4-yl, 1-methyl-1H-pyrazol-3-yl, 1-ethyl-1H-pyrazol-3-yl, 1,2,4-oxadiazol-5-yl, 2-methyl-2H-1,2,3-triazol-4-yl, 1-(2-hydroxyethyl)-1H-pyrazol-4-yl, pyrrolidin-2-yl, pyrrolidin-3-yl, 3-fluoro-pyrrolidin-3-yl, 1-methyl-pyrrolidin-2-yl, 4-fluoro-pyrrolidin-2-yl and 5-methyl-pyrrolidin-2-yl.

12. The compound of claim 1 wherein $R^2$ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydropyran-4-yl, 3-fluorotetrahydropyran-4-yl, 2-(hydroxymethyl)tetrahydropyran-4-yl, (4-tetrahydro-2H-pyran-2-yl) methyl acetate, tetrahydrofuran-3-yl, 3-methyloxetan-3-yl, oxetan-3-ylmethyl, 2-methoxyethyl, 2-methylpyrazol-3-yl, 2,5-dimethylpyrazol-3-yl and 1,3-dimethylpyrazol-4-yl.

13. The compound of claim 1 wherein Ar is selected from the group consisting of 4-chloro-3-fluorophenyl, 3-chloro-4-fluorophenyl, 3-fluoro-4-trifluoromethylphenyl, 3-fluoro-4-methoxyphenyl, 4-difluoromethoxyphenyl, 3-chloro-4-methoxyphenyl, 4-cyano-3-fluorophenyl, 3-chloro-4-cyanophenyl, 3-cyano-4-methoxyphenyl and 3-fluorophenyl.

14. The compound of claim 1 wherein $R^3$ is hydrogen or fluoro.

15. The compound of claim 1 selected from the group consisting of:
- N-((4-chloro-3-fluorophenyl)(1-methyl-1H-pyrazol-4-yl)methyl)-2-((S)-1-hydroxypropan-2-ylamino)quinazoline-7-carboxamide;
- 2-(tetrahydropyran-4-ylamino)-quinazoline-7-carboxylic acid [(4-chloro-3-fluoro-phenyl)-(1-methyl-1H-pyrazol-4-yl)-methyl]-amide;
- 2-(tetrahydropyran-4-ylamino)-quinazoline-7-carboxylic acid [(S)-(3-fluoro-4-trifluoromethyl-phenyl)-(S)-pyrrolidin-2-yl-methyl]-amide;
- 2-(tetrahydropyran-4-ylamino)-quinazoline-7-carboxylic acid [(4-chloro-3-fluoro-phenyl)-(1-methyl-1H-pyrazol-3-yl)-methyl]-amide;
- 2-isopropylamino-quinazoline-7-carboxylic acid [(S)-(3-fluoro-4-trifluoromethyl-phenyl)-(R)-pyrrolidin-2-yl-methyl]-amide;
- N-((4-chloro-3-fluorophenyl)(1-methyl-1H-pyrazol-3-yl)methyl)-2-((S)-1-hydroxypropan-2-ylamino)quinazoline-7-carboxamide;
- 2-(tetrahydropyran-4-ylamino)-quinazoline-7-carboxylic acid [(S)-(3-fluoro-4-trifluoromethyl-phenyl)-(R)-pyrrolidin-2-yl-methyl]-amide;
- 2-(tetrahydropyran-4-ylamino)-quinazoline-7-carboxylic acid [(R)-(3-chloro-4-fluoro-phenyl)-(R)-pyrrolidin-3-yl-methyl]-amide;
- 2-(tetrahydropyran-4-ylamino)-quinazoline-7-carboxylic acid [(R)-(3-chloro-4-fluoro-phenyl)-(S)-pyrrolidin-3-yl-methyl]-amide;
- 2-(tetrahydropyran-4-ylamino)-quinazoline-7-carboxylic acid [(S)-(3-chloro-4-fluoro-phenyl)-(S)-pyrrolidin-3-yl-methyl]-amide;
- 2-(tetrahydropyran-4-ylamino)-quinazoline-7-carboxylic acid [(S)-(3-chloro-4-fluoro-phenyl)-(R)-pyrrolidin-3-yl-methyl]-amide;
- 2-(tetrahydropyran-4-ylamino)-quinazoline-7-carboxylic acid [(S)-(4-chloro-3-fluoro-phenyl)-(1-methyl-1H-pyrazol-4-yl)-methyl]-amide;
- 2-(tetrahydropyran-4-ylamino)-quinazoline-7-carboxylic acid [(R)-(4-chloro-3-fluoro-phenyl)-(1-methyl-1H-pyrazol-4-yl)-methyl]-amide;
- 2-((S)-2-hydroxy-1-methyl-ethylamino)-quinazoline-7-carboxylic acid [(R)-(4-chloro-3-fluoro-phenyl)-(1-methyl-1H-pyrazol-4-yl)-methyl]-amide;
- 2-((S)-2-hydroxy-1-methyl-ethylamino)-quinazoline-7-carboxylic acid [(S)-(4-chloro-3-fluoro-phenyl)-(1-methyl-1H-pyrazol-4-yl)-methyl]-amide;
- 2-(tetrahydropyran-4-ylamino)-quinazoline-7-carboxylic acid [(3-chloro-4-fluoro-phenyl)-(3-fluoro-pyrrolidin-3-yl)-methyl]-amide;
- 2-(tetrahydropyran-4-ylamino)-quinazoline-7-carboxylic acid [(S)-(3-fluoro-4-trifluoromethyl-phenyl)-((R)-1-methyl-pyrrolidin-2-yl)-methyl]-amide;
- 2-(tetrahydropyran-4-ylamino)-quinazoline-7-carboxylic acid [(R)-(4-chloro-3-fluoro-phenyl)-(1-ethyl-1H-pyrazol-3-yl)-methyl]-amide;
- 2-(tetrahydropyran-4-ylamino)-quinazoline-7-carboxylic acid [(S)-(4-chloro-3-fluoro-phenyl)-(1-ethyl-1H-pyrazol-3-yl)-methyl]-amide;
- 2-(tetrahydropyran-4-ylamino)-quinazoline-7-carboxylic acid [(S)-(4-chloro-3-fluoro-phenyl)-(1-methyl-1H-pyrazol-3-yl)-methyl]-amide;
- 2-(tetrahydropyran-4-ylamino)-quinazoline-7-carboxylic acid [(R)-(4-chloro-3-fluoro-phenyl)-(1-methyl-1H-pyrazol-3-yl)-methyl]-amide;
- (S)-N-((4-chloro-3-fluorophenyl)(1-methyl-1H-pyrazol-3-yl)methyl)-5-fluoro-2-(tetrahydro-2H-pyran-4-ylamino)quinazoline-7-carboxamide;
- 2-(tetrahydropyran-4-ylamino)-quinazoline-7-carboxylic acid [(S)-(4-chloro-3-fluoro-phenyl)-(R)-pyrrolidin-2-yl-methyl]-amide;
- 2-(tetrahydropyran-4-ylamino)-quinazoline-7-carboxylic acid [(S)-(3-fluoro-4-methoxy-phenyl)-(R)-pyrrolidin-2-yl-methyl]-amide;
- 5-fluoro-2-(tetrahydropyran-4-ylamino)-quinazoline-7-carboxylic acid [(S)-(3-fluoro-4-methoxy-phenyl)-(R)-pyrrolidin-2-yl-methyl]-amide;
- 2-((R)-1-cyclopropyl-ethylamino)-quinazoline-7-carboxylic acid [(S)-(3-fluoro-4-methoxy-phenyl)-(R)-pyrrolidin-2-yl-methyl]-amide;
- 2-((3R,4R)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide;
- 2-((3S,4S)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide;
- 2-((3R,4S)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide;
- 2-((3S,4R)-3-fluoro-tetrahydropyran-4-ylamino)-quinazoline-7-carboxylic acid [(S)-(4-chloro-3-fluoro-phenyl)-(1-methyl-1H-pyrazol-4-yl)-methyl]-amide;
- 2-(tetrahydropyran-4-ylamino)-quinazoline-7-carboxylic acid [(S)-(3-fluoro-4-methoxy-phenyl)-((2R,4S)-4-fluoro-pyrrolidin-2-yl)-methyl]-amide;
- 2-(tetrahydropyran-4-ylamino)-quinazoline-7-carboxylic acid [(S)-(3-fluoro-4-methoxy-phenyl)-(1-methyl-1H-pyrazol-4-yl)-methyl]-amide;
- 5-fluoro-2-(tetrahydropyran-4-ylamino)-quinazoline-7-carboxylic acid [(S)-(3-fluoro-4-methoxy-phenyl)-(1-methyl-1H-pyrazol-4-yl)-methyl]-amide;
- 2-(tetrahydro-pyran-4-ylamino)-quinazoline-7-carboxylic acid [(4-chloro-3-fluoro-phenyl)-[1,2,4]oxadiazol-5-yl-methyl]-amide;
- 2-(tetrahydropyran-4-ylamino)-quinazoline-7-carboxylic acid [(S)-(4-chloro-3-fluoro-phenyl)-((2R,5R)-5-methyl-pyrrolidin-2-yl)-methyl]-amide;
- 2-(tetrahydropyran-4-ylamino)-quinazoline-7-carboxylic acid [(S)-(3-chloro-4-fluoro-phenyl)-((S)-3-fluoro-pyrrolidin-3-yl)-methyl]-amide;
- 2-(tetrahydropyran-4-ylamino)-quinazoline-7-carboxylic acid [(R)-(3-chloro-4-fluoro-phenyl)-((R)-3-fluoro-pyrrolidin-3-yl)-methyl]-amide;
- 2-(tetrahydropyran-4-ylamino)-quinazoline-7-carboxylic acid [(R)-(3-chloro-4-fluoro-phenyl)-((S)-3-fluoro-pyrrolidin-3-yl)-methyl]-amide;

2-(tetrahydropyran-4-ylamino)-quinazoline-7-carboxylic acid [(S)-(3-chloro-4-fluoro-phenyl)-((R)-3-fluoro-pyrrolidin-3-yl)-methyl]-amide;

2-((S)-2,2,2-trifluoro-1-methyl-ethylamino)-quinazoline-7-carboxylic acid [(S)-(4-chloro-3-fluoro-phenyl)-(S)-pyrrolidin-2-yl-methyl]-amide;

2-(tetrahydropyran-4-ylamino)-quinazoline-7-carboxylic acid [(S)-(4-difluoromethoxy-phenyl)-(1-methyl-1H-pyrazol-4-yl)-methyl]amide;

2-((2S,4S)-2-hydroxymethyl-tetrahydro-pyran-4-ylamino)-quinazoline-7-carboxylic acid [(S)-(4-chloro-3-fluoro-phenyl)-(1-methyl-1H-pyrazol-4-yl)-methyl]-amide;

2-((2S,4R)-2-hydroxymethyl-tetrahydro-pyran-4-ylamino)-quinazoline-7-carboxylic acid [(S)-(3-fluoro-4-methoxy-phenyl)-(1-methyl-1H-pyrazol-4-yl)-methyl]amide;

2-(tetrahydro-pyran-4-ylamino)-quinazoline-7-carboxylic acid [(S)-(3-chloro-4-methoxy-phenyl)-(1-methyl-1H-pyrazol-4-yl)-methyl]-amide;

2-(tetrahydro-pyran-4-ylamino)-quinazoline-7-carboxylic acid [(R)-(4-cyano-3-fluoro-phenyl)-(1-methyl-1H-pyrazol-4-yl)-methyl]-amide;

N-((S)-(3-fluoro-4-methoxyphenyl)(1-methyl-1H-pyrazol-4-yl)methyl)-2-((2S,4S)-2-(hydroxymethyl)tetrahydro-2H-pyran-4-ylamino)quinazoline-7-carboxamide;

N-((S)-(4-chloro-3-fluorophenyl)(1-methyl-1H-pyrazol-4-yl)methyl)-2-((2S,4R)-2-(hydroxymethyl)tetrahydro-2H-pyran-4-ylamino)quinazoline-7-carboxamide;

(R)—N-((3-chloro-4-cyanophenyl)(1-methyl-1H-pyrazol-4-yl)methyl)-2-(tetrahydro-2H-pyran-4-ylamino)quinazoline-7-carboxamide;

(R)—N-((3-cyano-4-methoxyphenyl)(1-methyl-1H-pyrazol-4-yl)methyl)-2-(tetrahydro-2H-pyran-4-ylamino)quinazoline-7-carboxamide;

(S)-N-((3-chloro-4-cyanophenyl)(1-methyl-1H-pyrazol-4-yl)methyl)-2-(tetrahydro-2H-pyran-4-ylamino)quinazoline-7-carboxamide;

(S)-5-fluoro-N4(3-fluoro-4-methoxyphenyl)(2-methyl-2H-1,2,3-triazol-4-yl)methyl)-2-(tetrahydro-2H-pyran-4-ylamino)quinazoline-7-carboxamide;

5-fluoro-N-((S)-(3-fluoro-4-methoxyphenyl)(1-methyl-1H-pyrazol-4-yl)methyl)-2-((3S,4S)-3-fluorotetrahydro-2H-pyran-4-ylamino)quinazoline-7-carboxamide;

5-fluoro-N-((3-fluoro-4-methoxyphenyl)(2-methyl-2H-1,2,3-triazol-4-yl)methyl)-2-(tetrahydro-2H-pyran-4-ylamino)quinazoline-7-carboxamide;

(R)-5-fluoro-N-((3-fluoro-4-methoxyphenyl)(2-methyl-2H-1,2,3-triazol-4-yl)methyl)-2-(tetrahydro-2H-pyran-4-ylamino)quinazoline-7-carboxamide;

(S)-N-((3-chloro-4-fluorophenyl)(1-methyl-1H-pyrazol-4-yl)methyl)-2-(tetrahydro-2H-pyran-4-ylamino)quinazoline-7-carboxamide;

(S)-N-((3-cyano-4-methoxyphenyl)(1-methyl-1H-pyrazol-4-yl)methyl)-2-(tetrahydro-2H-pyran-4-ylamino)quinazoline-7-carboxamide;

((2S,4S)-4-(7-((S)-(3-fluoro-4-methoxyphenyl)(1-methyl-1H-pyrazol-4-yl)methylcarbamoyl)quinazolin-2-ylamino)tetrahydro-2H-pyran-2-yl)methyl acetate;

(S)-5-fluoro-N-((3-fluoro-4-methoxyphenyl)(1-methyl-1H-pyrazol-4-yl)methyl)-2-(2-methoxyethylamino)quinazoline-7-carboxamide;

(S)-5-fluoro-N-((3-fluoro-4-methoxyphenyl)(1-methyl-1H-pyrazol-4-yl)methyl)-2-(3-fluoropropylamino)quinazoline-7-carboxamide;

(S)-2-(cyclopropylmethylamino)-5-fluoro-N-((3-fluoro-4-methoxyphenyl)(1-methyl-1H-pyrazol-4-yl)methyl)quinazoline-7-carboxamide;

5-fluoro-N-((S)-(3-fluoro-4-methoxyphenyl)(1-methyl-1H-pyrazol-4-yl)methyl)-2-((R)-tetrahydrofuran-3-ylamino)quinazoline-7-carboxamide;

5-fluoro-N-((S)-(3-fluoro-4-methoxyphenyl)(1-methyl-1H-pyrazol-4-yl)methyl)-2-((S)-tetrahydrofuran-3-ylamino)quinazoline-7-carboxamide;

(S)-5-fluoro-N-((3-fluoro-4-methoxyphenyl)(1-methyl-1H-pyrazol-4-yl)methyl)-2-(oxetan-3-ylmethylamino)quinazoline-7-carboxamide;

(S)-5-fluoro-N-((3-fluoro-4-methoxyphenyl)(1-methyl-1H-pyrazol-4-yl)methyl)-2-(3-methyloxetan-3-ylamino)quinazoline-7-carboxamide;

(S)-N-((3-chloro-4-cyanophenyl)(1-methyl-1H-pyrazol-4-yl)methyl)-5-fluoro-2-(tetrahydro-2H-pyran-4-ylamino)quinazoline-7-carboxamide;

(S)-N-((3-chloro-4-methoxyphenyl)(1-methyl-1H-pyrazol-4-yl)methyl)-5-fluoro-2-(tetrahydro-2H-pyran-4-ylamino)quinazoline-7-carboxamide;

(S)-N-((3-fluoro-4-methoxyphenyl)(1-(2-hydroxyethyl)-1H-pyrazol-4-yl)methyl)-2-(tetrahydro-2H-pyran-4-ylamino)quinazoline-7-carboxamide;

(S)-5-fluoro-N-((3-fluorophenyl)(1-methyl-1H-pyrazol-4-yl)methyl)-2-((tetrahydro-2H-pyran-4-yl)amino)quinazoline-7-carboxamide;

5-Fluoro-2-((1R,4S)-4-hydroxy-cyclohexylamino)-quinazoline-7-carboxylic acid [(S)-(3-fluoro-4-methoxy-phenyl)-(1-methyl-1H-pyrazol-4-yl)-methyl]-amide;

5-fluoro-N-((S)-(3-fluoro-4-methoxyphenyl)(1-methyl-1H-pyrazol-4-yl)methyl)-2-(((3R,4R)-3-fluorotetrahydro-2H-pyran-4-ylamino)quinazoline-7-carboxamide;

5-fluoro-N-[(3-fluoro-4-methoxy-phenyl)-(1-methylpyrazol-4-yl)methyl]-2-[(2,2,2-trifluoro-1-methyl-ethyl)amino]quinazoline-7-carboxamide;

5-fluoro-N-((S)-(3-fluoro-4-methoxyphenyl)(1-methyl-1H-pyrazol-4-yl)methyl)-2-(2,2,2-trifluoropropan-2-ylamino)quinazoline-7-carboxamide;

2-[(1 1-dioxothietan-3-yl)amino]-N-[(S)-(3-fluoro-4-methoxy-phenyl)-(1-methylpyrazol-4-yl)methyl]quinazoline-7-carboxamide;

5-fluoro-N—[(RN—[(R)-(3-fluoro-4-methoxy-phenyl)-(1-methylpyrazol-4-yl)methyl]-2-(tetrahydropyran-4-ylamino)quinazoline-7-carboxamide;

N-[(S)-(3-fluoro-4-methoxy-phenyl)-(1-methylpyrazol-4-yl)methyl]-2-(thietan-3-ylamino)quinazoline-7-carboxamide;

5-fluoro-N—[(R)-(3-fluoro-4-methoxy-phenyl)-(1-methylpyrazol-4-yl)methyl]-2-(tetrahydropyran-4-ylamino)quinazoline-7-carboxamide;

2-[(3 3-difluorocyclobutyl)amino]-5-fluoro-N-[(S)-(3-fluoro-4-methoxy-phenyl)-(1-methylpyrazol-4-yl)methyl]quinazoline-7-carboxamide;

N-((S)-(3-fluoro-4-methoxyphenyl)(1-methyl-1H-pyrazol-4-yl)methyl)-2-((1S,3R)-3-hydroxycyclobutylamino)quinazoline-7-carboxamide;

N-((S)-(3-fluoro-4-methoxyphenyl)(1-methyl-1H-pyrazol-4-yl)methyl)-2-((1R,3S)-3-hydroxycyclobutylamino)quinazoline-7-carboxamide;

(S)-N-((3-fluoro-4-methoxyphenyl)(1-methyl-1H-pyrazol-4-yl)methyl)-2-(3-methoxycyclobutylamino)quinazoline-7-carboxamide;

2-(2-cyanoethylamino)-5-fluoro-N-[(S)-(3-fluoro-4-methoxy-phenyl)-(1-methylpyrazol-4-yl)methyl]quinazoline-7-carboxamide;

5-fluoro-N-[(S)-(3-fluorophenyl)-(1-methylpyrazol-4-yl)methyl]-2-(tetrahydropyran-4-ylamino)quinazoline-7-carboxamide;

5-fluoro-N-((S)-(3-fluoro-4-methoxyphenyl)(1-methyl-1H-pyrazol-4-yl)methyl)-2-((1R,4S)-4-hydroxycyclohexylamino)quinazoline-7-carboxamide;

5-fluoro-N—[(R)-(5-methoxy-2-pyridyl)-(1-methylpyrazol-4-yl)methyl]-2-(tetrahydropyran-4-ylamino)quinazoline-7-carboxamide;

5-fluoro-N-[(S)-(3-fluoro-4-methoxy-phenyl)-(1-methylpyrazol-4-yl)methyl]-2-[[(3R,4R)-3-fluorotetrahydropyran-4-yl]amino]quinazoline-7-carboxamide;

N-[(S)-(3-fluoro-4-methoxy-phenyl)-(1-methylpyrazol-4-yl)methyl]-2-[(2-methylpyrazol-3-yl)amino]quinazoline-7-carboxamide;

N-[(S)-(3-fluoro-4-methoxy-phenyl)-(1-methylpyrazol-4-yl)methyl]-2-[(2-methyl-4-pyridyl)amino]quinazoline-7-carboxamide;

2-[(2,5-dimethylpyrazol-3-yl)amino]-N-[(S)-(3-fluoro-4-methoxy-phenyl)-(1-methylpyrazol-4-yl)methyl]quinazoline-7-carboxamide;

2-[(1,3-dimethylpyrazol-4-yl)amino]-5-fluoro-N-[(S)-(3-fluoro-4-methoxy-phenyl)-(1-methylpyrazol-4-yl)methyl]quinazoline-7-carboxamide;

5-fluoro-N-((S)-(3-fluoro-4-methoxyphenyl)(1-methyl-1H-pyrazol-4-yl)methyl)-2-((1S,4R)-4-hydroxycyclohexylamino)quinazoline-7-carboxamide;

5-fluoro-N-[(S)-(3-fluoro-4-methoxy-phenyl)-(1-methylpyrazol-4-yl)methyl]-2-[[(1S)-2-hydroxy-1-methyl-ethyl]amino]quinazoline-7-carboxamide;

5-fluoro-N-[(S)-(4-methoxyphenyl)-(1-methylpyrazol-4-yl)methyl]-2-(tetrahydropyran-4-ylamino)quinazoline-7-carboxamide;

5-fluoro-N-[(S)-(3-fluoro-4-methoxy-phenyl)-(1-methylpyrazol-4-yl)methyl]-2-[(2-methylpyrazol-3-yl)amino]quinazoline-7-carboxamide;

N-[(S)-(4-chloro-3-fluoro-phenyl)-(1-methylpyrazol-4-yl)methyl]-2-[(2 5-dimethylpyrazol-3-yl)amino]quinazoline-7-carboxamide;

N-[(S)-(4-chloro-3-fluoro-phenyl)-(1-methylpyrazol-4-yl)methyl]-2-[(2-methylpyrazol-3-yl)amino]quinazoline-7-carboxamide;

5-fluoro-N-[(S)-(3-fluorophenyl)-(1-methylpyrazol-4-yl)methyl]-2-[[(1S)-2-hydroxy-1-methyl-ethyl]amino]quinazoline-7-carboxamide;

2-[(1 3-dimethylpyrazol-4-yl)amino]-N-[(S)-(3-fluoro-4-methoxy-phenyl)-(1-methylpyrazol-4-yl)methyl]quinazoline-7-carboxamide;

N-[(S)-(3-fluoro-4-methoxy-phenyl)-(2-methylpyrazol-3-yl)methyl]-2-(tetrahydropyran-4-ylamino)quinazoline-7-carboxamide;

5-fluoro-N-[(S)-(3-fluoro-4-methoxy-phenyl)-(2-methylpyrazol-3-yl)methyl]-2-(tetrahydropyran-4-ylamino)quinazoline-7-carboxamide;

2-((1R,4S,5S)-2-oxabicyclo[2.2.1]heptan-5-ylamino)-N-((S)-(3-fluoro-4-methoxyphenyl)(1-methyl-1H-pyrazol-4-yl)methyl)quinazoline-7-carboxamide;

N-((S)-(3-fluoro-4-methoxyphenyl)(1-methyl-1H-pyrazol-4-yl)methyl)-2-(1-methoxypropan-2-ylamino)quinazoline-7-carboxamide;

5-fluoro-N-((S)-(3-fluoro-4-methoxyphenyl)(1-methoxy-1H-pyrazol-4-yl)methyl)-2-((1R,3S)-3-fluorocyclobutylamino)quinazoline-7-carboxamide;

5-fluoro-N-((S)-(3-fluoro-4-methoxyphenyl)(1-methoxy-1H-pyrazol-4-yl)methyl)-2-((1R,3S)-3-fluorocyclobutylamino)quinazoline-7-carboxamide;

5-fluoro-N-[(3-fluoro-4-methoxy-phenyl)-(1-methylpyrazol-4-yl)methyl]-2-(2-oxabicyclo[2.2.1]heptan-5-ylamino)quinazoline-7-carboxamide;

5-fluoro-N-[(4-methoxy-2-pyridyl)-(1-methylpyrazol-4-yl)methyl]-2-(tetrahydropyran-4-ylamino)quinazoline-7-carboxamide;

N-[(S)-(3-fluoro-4-methoxy-phenyl)-(2-methylpyrazol-3-yl)methyl]-2-[[(3S,4S)-3-fluorotetrahydropyran-4-yl]amino] quinazoline-7-carboxamide;

N-((S)-(3-fluoro-4-methoxyphenyl)(1-methyl-1H-pyrazol-5-yl)methyl)-2-((3R,4S)-3-fluorotetrahydro-2H-pyran-4-ylamino)quinazoline-7-carboxamide;

N-[(S)-(3-fluoro-4-methoxy-phenyl)-(2-methylpyrazol-3-yl)methyl]-2-[(2-methylpyrazol-3-yl)amino] quinazoline-7-carboxamide;

N-[(S)-(4-chloro-3-fluoro-phenyl)-(2-methylpyrazol-3-yl)methyl]-2-(tetrahydropyran-4-ylamino)quinazoline-7-carboxamide;

N-[(S)-(3-chloro-4-cyano-phenyl)-(2-methylpyrazol-3-yl)methyl]-2-(tetrahydropyran-4-ylamino)quinazoline-7-carboxamide;

N-[(S)-[3-fluoro-4-(trifluoromethyl)phenyl]-(1-methylpyrazol-4-yl)methyl]-2-(tetrahydropyran-4-ylamino)quinazoline-7-carboxamide;

N-[(4-chloro-3-fluoro-phenyl)-(3-fluoropyrrolidin-3-yl)methyl]-2-[(2-methylpyrazol-3-yl)amino]quinazoline-7-carboxamide;

N-[[4-(difluoromethoxy)phenyl]-(1-methylpyrazol-4-yl)methyl]-2-(tetrahydropyran-4-ylamino)quinazoline-7-carboxamide;

N-((R)-(3-fluoro-4-(trifluoromethoxy)phenyl)((S)-piperidin-3-yl)methyl)-2-(tetrahydro-2H-pyran-4-ylamino)quinazoline-7-carboxamide;

N-((S)-(3-fluoro-4-(trifluoromethoxy)phenyl)((R)-morpholin-2-yl)methyl)-2-(tetrahydro-2H-pyran-4-ylamino)quinazoline-7-carboxamide;

5-fluoro-N-[(S)-(3-fluoro-4-methoxy-phenyl)-(3-methylimidazol-4-yl)methyl]-2-(tetrahydropyran-4-ylamino)quinazoline-7-carboxamide;

5-fluoro-N-[(S)-(3-fluoro-4-methoxy-phenyl)-oxazol-5-yl-methyl]-2-(tetrahydropyran-4-ylamino)quinazoline-7-carboxamide;

5-fluoro-N-[(S)-(3-fluoro-4-methoxy-phenyl)-(3-methyltriazol-4-yl)methyl]-2-(tetrahydropyran-4-ylamino)quinazoline-7-carboxamide;

5-fluoro-N-[(S)-(3-fluoro-4-methoxy-phenyl)-(1-methylimidazol-4-yl)methyl]-2-(tetrahydropyran-4-ylamino)quinazoline-7-carboxamide;

5-fluoro-N-[(S)-(3-fluoro-4-methoxy-phenyl)-(1H-imidazol-2-yl)methyl]-2-(tetrahydropyran-4-ylamino)quinazoline-7-carboxamide;

5-fluoro-N-[(S)-(3-fluoro-4-methoxy-phenyl)-(2-methyl-1H-imidazol-4-yl)methyl]-2-(tetrahydropyran-4-ylamino)quinazoline-7-carboxamide;

5-fluoro-N-[(S)-(3-fluoro-4-methoxy-phenyl)-(1-methylimidazol-2-yl)methyl]-2-(tetrahydropyran-4-ylamino)quinazoline-7-carboxamide;

5-fluoro-N-[(S)-(3-fluoro-4-methoxy-phenyl)-(3-methylimidazol-4-yl)methyl]-2-[(2-methylpyrazol-3-yl)amino]quinazoline-7-carboxamide; and, 5-fluoro-N-[(S)-(3-fluoro-4-methoxy-phenyl)-(1-methylimidazol-2-yl)methyl]-2-[(2-methylpyrazol-3-yl)amino]quinazoline-7-carboxamide;

or a stereoisomer, tautomer or a pharmaceutically acceptable salt thereof.

16. A pharmaceutical composition comprising a compound of claim 1 or a stereoisomer, tautomer or pharmaceutically acceptable salt thereof and at least one pharmaceutically acceptable carrier, excipient or diluent.

17. A method of inhibiting extracellular-signal regulated kinase activity in a patient in need thereof comprising the step of administering to said patient a compound of claim 1 or a stereoisomer, tautomer or pharmaceutically acceptable salt thereof.

18. A method of inhibiting extracellular-signal regulated kinase activity in a patient suffering from a hyperproliferative disorder comprising the step of administering to said patient a compound of claim 1 or a stereoisomer, tautomer or pharmaceutically acceptable salt thereof.

19. The method of claim 18 wherein said hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

20. The method of claim 18 wherein said hyperproliferative disorder is selected from the group consisting of melanoma, pancreatic cancer, thyroid cancer colorectal cancer, lung cancer, breast cancer and ovarian cancer.

21. The method of claim 18 wherein said hyperproliferative disorder is selected from the group consisting of acute myelogenous leukemia, chronic myelomonocytic leukemia, chronic myelogenous leukemia, multiple myeloma and myeloid leukemia.

* * * * *